(12) United States Patent
Jin et al.

(10) Patent No.: US 12,325,852 B2
(45) Date of Patent: Jun. 10, 2025

(54) CHLAMYDOMONAS MUTANT AND USE THEREOF

(71) Applicant: INDUSTRY-UNIVERSITY COOPERATION FOUNDATION HANYANG UNIVERSITY, Seoul (KR)

(72) Inventors: Eon Seon Jin, Seoul (KR); Kwang Ryul Baek, Goyang-si (KR); In Hwa Song, Seoul (KR)

(73) Assignee: Industry-University Cooperation Foundation Hanyang University, Seoul (KR)

( * ) Notice: Subject to any disclaimer, the term of this patent is extended or adjusted under 35 U.S.C. 154(b) by 844 days.

(21) Appl. No.: 17/421,965

(22) PCT Filed: Jan. 9, 2020

(86) PCT No.: PCT/KR2020/000394
§ 371 (c)(1),
(2) Date: Jul. 9, 2021

(87) PCT Pub. No.: WO2020/145685
PCT Pub. Date: Jul. 16, 2020

(65) Prior Publication Data
US 2022/0403320 A1    Dec. 22, 2022

(30) Foreign Application Priority Data
Jan. 9, 2019 (KR) .......................... 10-2019-0002969

(51) Int. Cl.
| | | |
|---|---|---|
| *C12N 1/12* | (2006.01) | |
| *A23K 10/16* | (2016.01) | |
| *A23L 33/115* | (2016.01) | |
| *C12N 9/22* | (2006.01) | |
| *C12N 15/11* | (2006.01) | |
| *C12N 15/90* | (2006.01) | |
| *C12P 7/64* | (2022.01) | |

(52) U.S. Cl.
CPC ................ *C12N 1/12* (2013.01); *A23K 10/16* (2016.05); *A23L 33/115* (2016.08); *C12N 9/22* (2013.01); *C12N 15/11* (2013.01); *C12N 15/902* (2013.01); *C12P 7/64* (2013.01); *A23V 2002/00* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| 10,709,152 B2 | 7/2020 | Jin et al. |
| 2013/0203133 A1 | 8/2013 | Goodenough et al. |
| 2019/0045812 A1 * | 2/2019 | Jin ........................ A23L 33/135 |

FOREIGN PATENT DOCUMENTS

WO    WO-2013096993 A1 *   7/2013   ............... A01H 5/00

OTHER PUBLICATIONS

Eisenhauer et al., "Lutein and Zeaxanthin—Food Sources, Bioavailability and Dietary Variety in Age-Related Macular Degeneration Protection", Nutrients, vol. 9(120), pp. 1-14. (Year: 2017).*
Magali Siaut et al., "Oil accumulation in the model green alga *Chlamydomonas reinhardtii*: characterization, variability between common laboratory strains and relationship with starch reserves", BMC Biotechnology, 2011, pp. 1-15, vol. 11, No. 7.
Kwangryul Baek et al., "DNA-free two-gene knockout in Chlamydomonas reinhardtii via CRISPR-Cas9 ribonucleoproteins", Scientific Reports, Jul. 28, 2016, pp. 1-7.
Yantao Li et al., "Chlamydomonas starchless mutant defective in ADP-glucose pyrophosphorylase hyper-accumulates triacylglycerol", Metabolic Engineering, 2010, pp. 387-391, vol. 12.
International Search Report for PCT/KR2020/000394 dated Apr. 17, 2020 (PCT/ISA/210).

* cited by examiner

*Primary Examiner* — Michelle F. Paguio Frising
*Assistant Examiner* — Grant C Currens
(74) *Attorney, Agent, or Firm* — Sughrue Mion, PLLC

(57) ABSTRACT

The present invention relates to a novel *Chlamydomonas* strain with an improved oil generation function, the strain of the present invention having useful mycological characteristics as a strain that provides a useful substance, such as a vegetable oil, in a microalga, as the strain has a fast cell growth speed and an excellent lipid generation function compared to conventional strains. In particular, the present invention can provide a vegetable oil with improved stability and a longer preservation period by containing, in a cell, a large amount of antioxidant pigments such as lutein and zeaxanthin, and can, thereby, be usefully used in industries such as food, medicine, cosmetics, etc., which utilize a vegetable oil.

14 Claims, 24 Drawing Sheets
Specification includes a Sequence Listing.

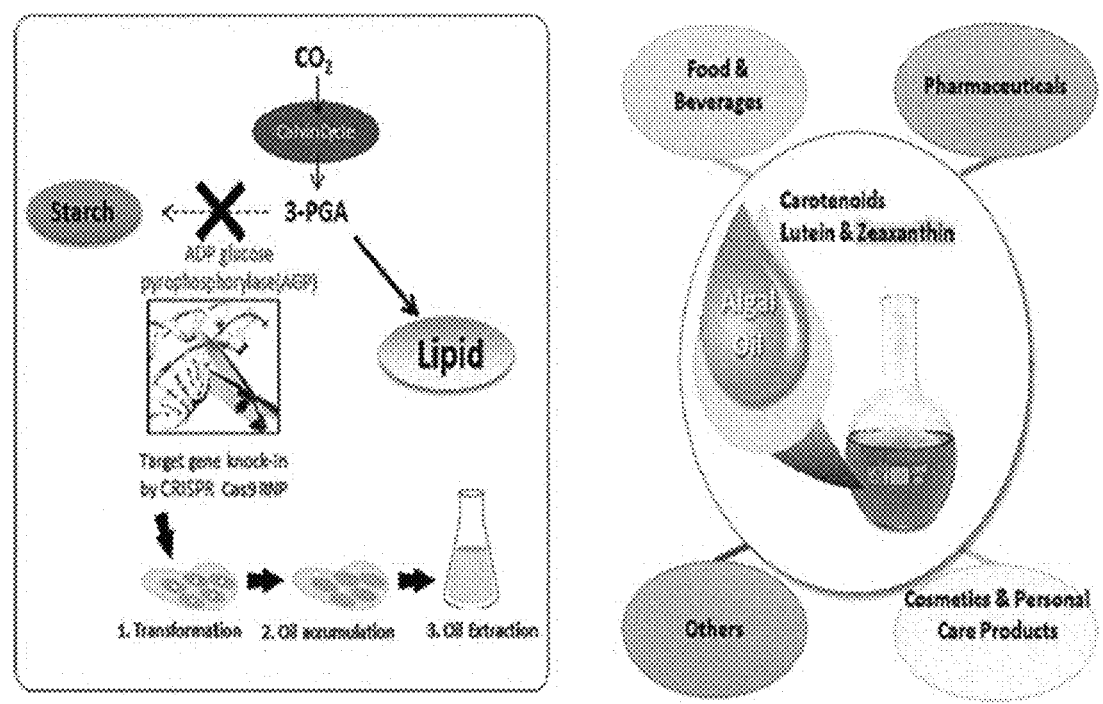
[FIG. 1]

FIG. 2A

Cre02.g095550.t1.2
Zeaxanthin epoxidase, chloroplast precursor (ABA1) (NPQ2) [PMID: 12671083] Previously annotated as ZEP > ZEP Mutant 1 ZEP gDNA sequence 5' UTR / CDS / 3' UTR / Target sequence
(Indel sequence)

GCGACGCACGGCTGGGCCAAATTCGCCAACGGCAGGAGACCAAATCGATCGAGGCGATCTTGCGAAGTTCTCG
GACAAATCGATCGCACCCATAGTGATTTAAGCATTACATTTGCCCAAGGCGTGAGAAGTGCGAGGCCCGAACGG
CTATGACGCCAATGCGCAGCTTACGACATTTAAAGCAAATTATTCATACATCATACAGCACGCTTATGTGAAGAAA
GCCAGGATTTTAGGCTCTCGCCCCGATCAAGACGATCTCCCCATTGCGAAGTTCTCGGTTTCTTTCCGGTTCGCCT
GCTCCGTATGATTTACCTTTGCGCTACAACAGCGACTTAAACGACCTACGTCGCCTTACTGTGTGCGCGTACGTGT
TTGTAGCTGTGAGATAGTTTTGTCCGCAGCGTACCCGCAAATAGAATGCTCGCGAGCACTTACACGCCCTGTGGC
GTTCGCCAGGTGGCAGGCCGCACGGTTGCAGTGCCCAGCAGCTTGGTCGCGCCAGTGGCAGTCGCTCGGTCG
CTGGGGTTGGCCGCCCTACGTCCCTGTATGTGAGCCTTCTGCGGCGCTTCCGGCCTGCCAGCAGCCTAGCGGGCG
TCGTCATGTTCAGACTGCTGCCACTCTCCGTGCCGACAACCCCAGCTCGGTCGCGCAGCTGGTGCATCAGAATG
GAAAGGGGATGAAGGTTATTATCGCCGGCGCGGGCATCGGCGGCCTGGTGCTAGCCGTTGCACTTCTGAAGCA
GGGCTTCCAGGTTCAGGTCTTTGAGCGCGACCTGACGGCCATCCGCGGCGAGGGCAAGTACCGTGGACCCATC
(GAAATTAATAAGACTCATTATATTCCGGCGAACGCACCTGGA)CAGGTGCGTTCGCCGGAACACCAACGCGCT
TGTTTTTGCTGTGCCGCGACCATGAACTAGGCCTTATCTTGAGGTGTTAGCATGTTTAGCCAGCGTTGGATCTGT
GTGGCGAGGTTGGGGTGAGAACCCTTCCTGTGTACCTGCTCGGGCGTACCTTGTGCCCCACCGCTGACTGGCTT
ACTTAATGACAAAACGCAGGTTCAAAGCAATGCGCTCGCTGCGCTGGAGGCTATCGATCCCGAGGTGGCCGCG
GAGGTGCTGCGCGAGGGCTGCATCACTGGCGACCGTATCAACGGGCTCTGCGACGGCCTGACTGGCGAGTGG
TGAGTAGGCAATCCAGCTGTGCATCCAGTCGCGCGGTTGCGGAGGTCGTCTCGGGAAACGCGACGTGGCGTCC
ACTCGCCCAAGGAGTGGTCTCCCGCAGCGTGGTCTCCCGCAGCTCGGGTGCAACACCCTGCCCCCTGCCGCGA
GCGCGCTGCGCTTGCTTATGTTGCGCAGCGGTGTGAGTTACAACAGCTTCTGTTGAAGAGCTGTCATACGAAGC
ACGGCGCGCTGTGGCGCTGCAGCCGTGCTGTGGAAACTCCAACACCTCCACCGCCAGCCTGCGCACGCACACG
CAATACACTCGCCTCGTGTGCCCCCTCCTCACACAACGGCATGTGACACTCAGTTTTAACTCTTATTTTGACAGCT
GAGAGCTACACGCTTGGGTGAATGGGGAGGTCCTTGATGTTTCGTTGCACTCCGTGGCTCCGGAGTCCGTGCG
GACCGTCACCCACAAATGGGAGCGCACGGCTTTCTTGTGCTGTCTGCCCCGTTAGCCACTAACTGCGAATGACC
TTGACAGTTTACTTTGCTATTTTTCCTTCCAGGTACGTCAAGTTCGACACGTTCCACCCGGCGGGTCAGCAAGGGC
CTGCCGGTGACCCGCGTCATCAGCCGCCTCACGCTGCAGCAGATCCTGGCCAAAGCCGTGGAGCGGTGAGCCG
TGCGCGCGGTGTGATGGCTTTAGCGTCAGTGCTAGCATGGGGGTTGGTGGGTGGTAATCGCGGCGCCCATGGC
CGGGTAGCAGCGGCCGAAAGCTGGCGCAGAGCGCGCGTTGGACAAGCGGTCCTGTTGCCGGTATGGGCACGA
GCAGGGCGCTGGTGCGGGCAAAGGGCAGAGTGGAGTTGCAGAGCAGCGCTGGCGTCGGCTGTGCGCTCTCC
AAATGGCCTCGTGGCATTCTGACGGGACACATCCTGGAAAATAGTAGCGCACCCAACTGCTGGTGGCTCCTCGT
ACAATCCCCCCAATTTACAATCGCTCGTTCTGGCTCGCAGCTACGGCGGCCCCGGCACCATCCAGAACGGCTGCA
ACGTGACCGAGTTCACGGAGCGCCGCAACGACACCACCGGCAACAACGAGGTGAGAGCGTGCTAAGAAGAG
CATGCACGTGGAGCGTGTAAAATTGTGTGGCCTGAAGCGGCAGTGCCTGCGGCATGGACTAGGTGGTTGCAGC
ATGCTGCGCGCGTGGGTTGCCGGTCAGGAAACCGCCGGACCGAGCCGCGCAGATTCAGTCAGGAGCGGATTA
GGAAGTTTGAAAAACAGGGTTCGGAGTGTGCAAGCGGGCTCAGGAGCTGTGGTGCCTTTCTACACCGGTCGC
CCTACCAGGCACCCACTGAAACTGTAAAACCGTTGCTGCGCCGGCGATGCCCTCTACTTCACTAGGTGACTGTGC
AGCTGGAGGACGGGCGCACGTTTGCGGCCGACGTGCTGGTGGGCGCCGACGGCATCTGGTCCAAGATCCGTA
AGCAGCTCATTGGCGAGACCAAGGCCAACTACAGCGGGTACACCTGCTACACCGGTGAGATTATTGACCTTCAA
GTTGGAAGGAGGGAGCGGGGGGAGCGGAATGGAAGGAAGCAGCGTGGACGGGGCGCACGGAGGGGAGG
GGACTGCGGGTCATAGCGCCGCCTTGCGGGGCGTGAGGAGTGTTGGGCGGATATTCAGTTTTCTTTGCCCAAG
ATCTTCCCACAATCCGCGTGTGTCTGACGCGGGATGTGGCCCCTGCTGCCATGGCTTCGCAGGCATCTCGGACTT
TACGCCGGCGGACATTGACATTGTGGGCTACCGCGTGTTCCTGGGCAACGGCCAGTACTTTGTCAGCAGCGACG
TGGGCAACGGCAAGATGCAGTGGTGAGCGGCGGCGGGCGGGCGAGCGAGGGCTGCGGGGTCTGGAGGGTG
TGTACCGGGCGGAAGGGAGGGGAAGGGAGGGGAAGGGAAGGCAGGATGCAGGCGAGGGCAGGATGTGAT

FIG. 2B

```
GGTGGGAAGAGGGCGTGGCGAGCAGCAACTGGAAAGGTGGTGGGTAAAAAAATGGTCCATGAATATGGCTC
GGTACAGTTCAAAGCATGGAAATGGAACCCGCCGTCTGCTGCACCATGGGCGTGAGCGGGGAGTACGCGACTC
CTGGACAGCCGTAACAATGCGGATGGCCTCAACAAGCCAGGAGCGGCACGAACCCAGCTCACGAGCGCACAG
CGTGCCAGGACGGCGGCCGGCAAGGATGAAATGTTTTTCCTAATATAAATGCGGACTCCTGACGCATTATATCCA
TTTTGCCACTGAGCCAAAGACACATATATACACGTGCGCCGCCGTCCTGCGCCACAGCCGCCTAGCGCTCCGGCC
GCGCCCGGTTCCCTCGGCGTCATGCGCTGGAGCCCCTCGCACCCTGCACCGCAAAGCCCATCAACACCACACT
CGTCCCCACACCGCGAGTCACCGCCACTGCACTCGCTGTCCCTCAACCCGTCACAATCTCGCCGACACGCGATAA
CGAACCCACGCAGGTACGGCTTCCACAAGGAGCCGTCTGGCGGCACCGACCCCGAGGGCAGCCGCAAGGCGC
GCCTGCTGCAGATCTTTGGCCACTGGAACGACAACGTGGTGGACCTGATCAAGGCCACGCCCGAGGAGGACGT
GCTGCGCCGCGACATCTTTGACAGGTACGGAAAAAGGGAGAGCGGGGTGGCTGGAGGGCGGGAAAGGGCG
AAGGGGCGGAGAAAGAAATGACTAGGGGATGGTGTTCATTTGTGGGATTGAGAGGGGTCCGCGGATCCCGGC
AGAGGGCGCCAGTGGCAAGGCGTGGGAGTCGCGGGGCGGACAATGCTGGGCCAGGGGCGCCTAGTCACCCC
GGGACACTGTCTCAGTATGCCGCCGTCCCGGCCGCGCCGCACAGGCCGCCCATCTTCACCTGGAGCAAGGGCC
GCGTGGCCCTGCTGGGCGACAGCCGCACGCCATGCAGCCCAACCTGGGCCAGGGCGGCTGCATGGCCATTG
AGGACGCCTACGAGCTGGCCATCGACCTCAGCCGCGCCGTGTCCGACAAGGCCGGAAACGCGGCGGCGGTGG
ACGTGGAGGGCGTGCTGCGCAGCTACCAGGACAGCCGCATTTTGCGCGTCAGCGCCATTCACGGCATGGCGGG
TGAGAGCTGCAACCAGCGTAGTCGGGCTGGGCTGCTGTGGGCAGGGTCGGGTTGGGTTGGGCGCACGTGGG
CGGCGAGTGTATGTGCAGTGTGACGTGCACACTATCATAATACTTTATGCTCACCGCACCGCGCCGCGCCGCACC
ACGCGCCACAGGCATGGCTGCCTTCATGGCCAGCACCTACAAGTGCTACCTGGGCGAGGGCTGGAGCAAGTGG
GTTGAGGGGCTGCGCATCCCGCACCCCGGCCGCGTGGTGGGCGGCTGGTGATGCTGCTCACCATGCCCAGCG
TGCTGGAGTGGGTGCTGGGCGGCAACACCGACCACGTGGCGCCGCACCGCACCAGCTACTGCTCGCTGGGCG
ACAAGCCCAAGGTGAGCGGCTGCCGGGCTGGGGGGGGTGGAGGGAGAGGAGGAGGATTGCGGGGA
GACGAGGGAGGGCAAGGCAGGCGCTGCCTTCGTGGATGCACCGCCCGTCGTTAGCAGGACCTCAGGAACTC
GTCCCCAAAACCACAACAGAACCCCCAATATCGCCTCTTCCTTCACTGCTTGTCACGCCTGGTCCGCCGACCGCA
GGCTTTCCCCGAGAGCCGCTTCCCCGAGTTCATGAACAACGACGCCTCCATCATCCGCTCCTCCCACGCCGACTG
GCTGCTGGTGGCGGAGCGCGACGCCGCCACGGCCGCCGCCGCCAACGTGAACGCCGCCACCGGCAGCAGCGC
CGCCGCGGCCGCCGCCGCCGACGTGAACAGCAGCTGCCAGTGCAAGGGCATCTACATGGCGGACTCGGCGGC
CCTGGTGGGCCGCTGCGGCGCCACCTCGCGCCCCGCGCTGGCCGTGGACGACGTGCACGTCGCCGAGAGTCA
CGCGCAGGTCTGGCGCGGCCTCGCCGGCCTCCCCCCTCCTCGTCGTCCGCCTCCACCGCCGCCGCCTCTGCGT
CCGCCGCCTCCTCTGCCGCCAGCGGCACCGCCAGCACCCTGGGCAGCTCGGAGGGCTACTGGCTCCGCGACCT
GGGCAGCGGCCGCGGCACCTGGGTCAACGGCAAGCGCCTGCCCGACGGCGCCACGGTGCAGCTGTGGCCCG
GCGACGCGGTGGAGTTCGGCCGGCACCCCAGCCACGAGGTGTTCAAGGTGAAGATGCAGCACGTGACGCTGC
GCAGCGACGAGCTCAGCGGCCAGGCCTACACCACGCTCATGGTGGGCAAGATCCGGAACAACGACTACGTCAT
GCCCGAGTCGCGGCCGGACGGCGGCAGCCAGCAGCCGGGCCGCCTGGTGACGGCTTAAGCGGCGCCGTGCG
TAAGGGCCGGCTTACGGGGCGGCAGTGTCGCTGTGGAGGGATGGTCTGGGGTGGGAGGAATGGGAGGAG
AGCGGCGGGAGCCCGAGGAGCGGAGCGCTGGAGGCTTGCGGAGCGGCAGCTTGGGAAGAGCTGCGGAGA
GAGGAAGGAGCGCAGGGCGCTTGGAGCACGCGCCAGATTACGATCACGGCAGCGCGAGGCGCGCGTCTGAC
TTCGAAGTGGTAAGGAAGATTTCATGTATGATTGCGTCGAGGGACACCGCAAGTTTTACGCGCGGCGGAGGGA
GCCTTGGGGCATACAACAGTACGAGCGGGCGTTGGTGAGAAGGTGGTCACTCCGTATGAGAAGATGGTTACTC
CGTACCTTCGTGAGAAGCTGCTGCGCACAAGTTACGAACCTATCTGTGTGGAGAGCCCGGTAGTATATCAGGGG
CGAGGGTCATGAACGCGAGTGGCGAGTCTGTGAGCGCCAATTTGTTATGCGGCATAATTTCGCATCGGGGTATT
ACGTCTACAAAATGTTGAGCTGGCTTAGCGCAGGAGGCAACACCTCAGGCAGAATGTACGAATGTGTGCAGAA
GGGCAGAGTCAAGGCAGAGGCGGAGAAGTTGTCAGGGCTGTGTGTGGTTTGGTCAGGGCGTGGCTAGATGG
ATATGAGACCCGCCGCCGTCTCCAGATTGTGGCGGAGGTGGAACTCTCGGCCCCCGCGCCAGTCCCCGCGGCC
AGCGCATCCCGCCATGCGGGTTGTTGGCTGGTGCATCGCGCGGGGTGTGCTATGAGTGTGGAAACACTATGTCG
CGTGTCGTGCTGAGGTCTGTTGAGAGGTTTCGTCGTTTGTGCATGTCCTGTCCCGGTTGGAGTTTGAGCGAGGT
GGTTCAAAGTTTTTGGATCGCGTGGGAGAGACTGAAACGGTTTGGTGAGAATGGTTGAGACAGAGGTTGGGC
TTGGAAACTGGAGGAGAGGAGCAGCGTAACTCGAGGACGATGCAGTAGATGCACCACAACAGTTGTGGTGGG
CGCCTGGAGTAACACGCGTGCCACCAACACGCAATTACAGAGATCCGTCATACAGGAGGGATCATATGCGATTTA
ATTTTGGTTTTGCATTTGTAAGACGTTTTCACA
```

FIG. 2C

Information on zeaxanthin epoxidase (ZEP) gene of Chlamydomonas wild-type and ZEP genes in ZEP mutants 1, 2, and 3

Cre02.g095550.t1.2
Zeaxanthin epoxidase, chloroplast precursor (ABA1) (NPQ2) [PMID 12671083]. Previously annotated as ZEP >ZEP Mutant 2 ZEP gDNA sequence     5' UTR / CDS / 3' UTR / Target sequence
                   44bp Insertion                       (Indel sequence)

```
GCGACGCACGGCTGGGCCAAATTCGCCAACGGCAGGAGACCAAATCGATCGAGGCGATCTTGCGAAGTTCTCG
GACAAATCGATCGCACCCATAGTGATTTAAGCATTACATTTGCCCAAGGCGTGAGAAGTGCGAGGCCCGAACGG
CTATGACGCCAATGCGCAGCTTACGACATTTAAAGCAAATTATTCATACATCATACAGCACGCTTATGTGAAGAAA
GCCAGGATTTTAGGCTCTCGCCCCGATCAAGACGATCTCCCCATTGCGAAGTTCTCGGTTTCTTTCCGGTTCGCCT
GCTCCGTATGATTTACCTTTGCGCTACAACAGCGACTTAAACGACCTACGTCGCCTTACTGTGTGCGCGTACGTGT
TTGTAGCTGTGAGATAGTTTTGTCCGCAGCGTACCCGCAAATAGAATGCTCGCGAGCACTTACACGCCCTGTGGC
GTTCGCCAGGTGGCAGGCCGCACGGTTGCAGTGCCCAGCAGCTTGGTCGCGCCAGTGGCAGTCGCTCGGTCG
CTGGGGTTGGCGCCCTACGTCCCTGTATGTGAGCCTTCTGCGGGCGCTTCCGGCCTGCCAGCAGCCTAGCGGGCG
TCGTCATGTTCAGACTGCTGCCACTCTCCGTGCCGACAACCCCAGCTCGGTCGCGCAGCTGGTGCATCAGAATG
GAAAGGGGATGAAGGTTATTATCGCCGGCGCGGGCATCGGCGGCCTGGTGCTAGCCCGTTGCACTTCTGAAGCA
GGGCTTCCAGGTTCAGGTCTTTGAGCGCGACCTGACGGCCATCCGCGGCGAGGGCAAGTACCGTGGACCCATC
{TAGCTCTAAAACATCCAGGTGCGTTCGCCGGACTATAGTGAGTA]CAGGTGCGTTCGCCGGAACACCAACGCG
CTTGTTTTTGCTGTGCCGCGACCATGAACTAGGCCTTATCTTGAGGTGTTAGCATGTTTAGCCAGCGTTGGATCT
GTGTGGCGAGGTTGGGGTGAGAACCCTTCCTGTGTACCTGCTCGGGCGTACCTTGTGCCCCACCGCTGACTGGC
TTACTTAATGACAAAACGCAGGTTCAAAGCAATGCGCTCGCTGCGCTGGAGGCTATCGATCCCGAGGTGGCCGC
GGAGGTGCTGCGCGAGGGCTGCATCACTGGCGACCGTATCAACGGGCTCTGCGACGGCCTGACTGGCGAGTG
GTGAGTAGGCAATCCAGCTGTGCATCCAGTCGCGCGGTTGCGGAGGTCGTCTCGGGAAACGCGACGTGGCGTC
CACTCGCCCAAGGAGTGGTCTCCCGCAGCGTGGTCTCCCGCAGCTCGGGTGCAACACCCTGCCCCCTGCCGCG
AGCGCGCTGCGCTTGCTTATGTTGCGCAGCGGTGTGAGTTACAACAGCTTCTGTTGAAGAGCTGTCATACGAAG
CACGGCGCGCTGTGGCGCTGCAGCCGTGCTGTGGAAACTCCAACACCTCCACCGCCAGCCTGCGCACGCACAC
GCAATACACTCGCCTCGTGTGCCCCCTCCTCACACAACGGCATGTGACACTCAGTTTTAACTCTTATTTTGACAGC
TGAGAGCTACACGCTTGGGTGAATGGGGAGGTCCTTGATGTTTCGTTGCACTCCGTGGCTCCGGAGTCCGTGC
GGACCGTCACCCACAAATGGGAGCGCACGGCTTTCTTGTGCTGTCTGCCCCGTTAGCCACTAACTGCGAATGAC
CTTGACAGTTTACTTTGCTATTTTTCCTTCCAGGTACGTCAAGTTCGACACGTTCCACCCGGCGGTCAGCAAGGG
CCTGCCGGTGACCCGCGTCATCAGCCGCCTCACGCTGCAGCAGATCCTGGCCAAAGCCGTGGAGCGGTGAGCC
GTGCGCGCGGTGTGATGGCTTTAGCGTCAGTGCTAGCATGGGGGTTGGTGGGTGGTAATCGCGGCGCCCATGG
CCGGGTAGCAGCGGCCGAAAGCTGGCGCAGAGCGCGCGTTGGACAAGCGGTCCTGTTGCCGGTATGGGCACG
AGCAGGGCGCTGGTGCGGGCAAAGGGCAGAGTGGAGTTGCAGAGCAGCGCTGGCGTCGGCTGTGCGCTCTC
CAAATGGCCTCGTGGCATTCTGACGGGACACATCCTGGAAAATAGTAGCGCACCCAACTGCTGGTGGCTCCTCG
TACAATCCCCCCAATTTACAATCGCTCGTTCTGGCTCGCAGCTACGGCGGCCCCGGCACCATCCAGAACGGCTGC
AACGTGACCGAGTTCACGGAGCGCCGCAACGACACCACCGGCAACAACGAGGTGAGAGCGTGCTAAGAAGA
GCATGCACGTGGAGCGTGTAAAATTGTGTGGCCTGAAGCGGCAGTGCCTGCGGCATGGACTAGGTGGTTGCAG
CATGCTGCGCGCGTGGGTTGCCGGTCAGGAAACCGCCGGACCGAGCCGCGCAGATTCAGTCAGGAGCGGATT
AGGAAGTTTGAAAAACAGGGTTCGGAGTGTGCAAGCGGGCTCAGGAGCTGTGGTGCCTTTCTACACCGGTCG
CCCTACCAGGCACCCACTGAAACTGTAAAACCGTTGCTGCGCCGGCGATGCCCTCACTTCACTAGGTGACTGTG
CAGCTGGAGGACGGGCGCACGTTTGCGGCCGACGTGCTGGTGGGCGCCGACGGCATCTGGTCCAAGATCCGT
AAGCAGCTCATTGGCGAGACCAAGGCCAACTACAGCGGGTACACCTGCTACACCGGTGAGATTATTGACCTTCA
AGTTGGAAGGAGGGAGCGGGGGGAGCGGAATGGAAGGAAGCAGCGTGGACGGGGCGCACGGAGGGGAG
GGGACTGCGGGTCATAGCGCCGCCTTGCGGGGCGTGAGGAGTGTTGGGCGGATATTCAGTTTTCTTTGCCCAA
GATCTTCCACAATCCGCGTGTGTCTGACGCGGGATGTGGCCCCTGCTGCCATGGCTTCGCAGGCATCTCGGACT
TTACGCCGGCGGACATTGACATTGTGGGCTACCGCGTGTTCCTGGGCAACGGCCAGTACTTTGTCAGCAGCGAC
GTGGGCAACGGCAAGATGCAGTGGTGAGCGGCGGCGGGCGGGCGAGCGAGGGCTGCGGGTCTGGAGGGT
GTGTACCGGGCGGAAGGGAGGGGAAGGGAGGGGAAGGGAAGGCAGGATGCAGGCGAGGGCAGGATGTGA
```

FIG. 2D

```
TGGTGGGAAGAGGGCGTGGCGAGCAGCAACTGGAAAGGTGGTGGGTAAAAAAATGGTCCATGAATATGGCTC
GGTACAGTTCAAAGCATGGAAATGGAACCCGCCGTCTGCTGCACCATGGGCGTGAGCGGGGAGTACGCGACTC
CTGGACAGCCGTAACAATGCGGATGGCCTCAACAAGCCAGGAGCGGCACGAACCCAGCTCACGAGCGCACAG
CGTGCCAGGACGGCGGCCGGCAAGGATGAAATGTTTTTCCTAATATAAATGCGGACTCCTGACGCATTATATCCA
TTTTGCCACTGAGCCAAAGACACATATATACACGTGCGCCGCCGTCCTGCGCCACAGCCGCCTAGCGCTCCGGCC
GCGCCCGGTTCCCTCGGCGTCATGCGCTGGAGCCCCTCGCACCCTGCACCGCAAAGCCCATCAACACCACACT
CGTCCCCACACCGCGAGTCACCGCCACTGCACTCGCTGTCCCTCAACCCGTCACAATCTCGCCGACACGCGATAA
CGAACCCACGCAGGTACGGCTTCCACAAGGAGCCGTCTGGCGGCACCGACCCCGAGGGCAGCCGCAAGGCGC
GCCTGCTGCAGATCTTTGGCCACTGGAACGACAACGTGGTGGACCTGATCAAGGCCACGCCCGAGGAGGACGT
GCTGCGCCGCGACATCTTTGACAGGTACGGAAAAAGGGAGAGCGGGGTGGCTGGAGGGCGGGAAAGGGCG
AAGGGGCGGAGAAAGAAATGACTAGGGATGGTGTTCATTTGTGGGATTGAGAGGGGTCCGCGGATCCCGGC
AGAGGGCGCCAGTGGCAAGGCGTGGGAGTCGCGGGGCGGACAATGCTGGGCCAGGGGCGCCTAGTCACCCC
GGGACACTGTCTCAGTATGCCGCCGTCCCGGCCGCGCCGCACAGGCCGCCCATCTTCACCTGGAGCAAGGGCC
GCGTGGCCCTGCTGGGCGACAGCGCGCACGCCATGCAGCCCAACCTGGGCCAGGGCGGCTGCATGGCCATTG
AGGACGCCTACGAGCTGGCCATCGACCTCAGCCGCGCCGTGTCCGACAAGGCCGGAAACGCGGCGGCGGTGG
ACGTGGAGGGCGTGCTGCGCAGCTACCAGGACAGCCGCATTTTGCGCGTCAGCGCCATTCACGGCATGGCGGG
TGAGAGCTGCAACCAGCGTAGTCGGGCTGGGCTGCTGTGGGCAGGGTCGGGTTGGGTTGGGCGCACGTGGG
CGGCGAGTGTATGTGCAGTGTGACGTGCACACTATCATAATACTTTATGCTCACCGCACCGCGCCGCGCCGCACC
ACGCGCCACAGGCATGGCTGCCTTCATGGCCAGCACCTACAAGTGCTACCTGGGCGAGGGCTGGAGCAAGTGG
GTTGAGGGGCTGCGCATCCCGCACCCCGGCCGCGTGGTGGGGCGGCTGGTGATGCTGCTCACCATGCCCAGCG
TGCTGGAGTGGGTGCTGGGCGGCAACACCGACCACGTGGCGCCGCACCGCACCAGCTACTGCTCGCTGGGCG
ACAAGCCCAAGGTGAGCGGCTGCCGGGCTGGGGGGGGTGGAGGGAGAGGAGGAGGATTGCGGGGA
GACGAGGGAGGGCAAGGCAGGCGCTGCCTTCGTGGATGCACCGCCCCGTCGTTAGCAGGACCTCAGGAACTC
GTCCCCAAAACCACAACAGAACCCCCAATATCGCCTCTTCCTTCACTGCTTGTCACGCCTGGTCCGCCGACCGCA
GGCTTTCCCCGAGAGCCGCTTCCCCGAGTTCATGAACAACGACGCCTCCATCATCCGCTCCTCCCACGCCGACTG
GCTGCTGGTGGCGGAGCGCGACGCCGCCACGGCCGCCGCCGCCAACGTGAACGCCGCCACCGGCAGCAGCGC
CGCCGCGGCCGCCGCCGCCGACGTGAACAGCAGCTGCCAGTGCAAGGGCATCTACATGGCGGACTCGGCGGC
CCTGGTGGGCCGCTGCGGCGCCACCTCGCGCCCCGCGCTGGCCGTGGACGACGTGCACGTCGCCGAGAGTCA
CGCGCAGGTCTGGCGCGGCCTCGCCGGCCTCCCCCCTCCTCGTCGTCCGCCTCCACCGCCGCCGCCTCTGCGT
CCGCCGCCTCCTCTGCCGCCAGCGGCACCGCCAGCACCCTGGGCAGCTCGGAGGGCTACTGGCTCCGCGACCT
GGGCAGCGGCCGCGGCACCTGGGTCAACGGCAAGCGCCTGCCCGACGGCGCCACGGTGCAGCTGTGGCCCG
GCGACGCGGTGGAGTTCGGCCGGCACCCCAGCCACGAGGTGTTCAAGGTGAAGATGCAGCACGTGACGCTGC
GCAGCGACGAGCTCAGCGGCCAGGCCTACACCACGCTCATGGTGGGCAAGATCCGGAACAACGACTACGTCAT
GCCCGAGTCGCGGCCGGACGGCGGCAGCCAGCAGCCGGGCCGCCTGGTGACGGCTTAAGCGGCGCCGTGCG
TAAGGGCCGGCTTACGGGGCGGCAGTGTCGCTGTGGAGGGATGGTCTGGGGTGGGAGGAATGGGAGGAG
AGCGGCGGGAGCCCGAGGAGCGGAGCGCTGGAGGCTTGCGGAGCGGCAGCTTGGGAAGAGCTGCGGAGA
GAGGAAGGAGCGCAGGGCGCTTGGAGCACGCGCCAGATTACGATCACGGCAGCGCGAGGCGCGCGTCTGAC
TTCGAAGTGGTAAGGAAGATTTCATGTATGATTGCGTCGAGGGACACCGCAAGTTTTACGCGCGGCGGAGGGA
GCCTTGGGGCATACAACAGTACGAGCGGGCGTTGGTGAGAAGGTGGTCACTCCGTATGAGAAGATGGTTACTC
CGTACCTTCGTGAGAAGCTGCTGCGCACAAGTTACGAACCTATCTGTGTGGAGAGCCCGGTAGTATATCAGGGG
CGAGGGTCATGAACGCGAGTGGCGAGTCTGTGAGCGCCAATTTGTTATGCGGCATAATTTCGCATCGGGGTATT
ACGTCTACAAAATGTTGAGCTGGCTTAGCGCAGGAGGCAACACCTCAGGCAGAATGTACGAATGTGTGCAGAA
GGGCAGAGTCAAGGCAGAGGCGGAGAAGTTGTCAGGGCTGTGTGTGGTTTGGTCAGGGCGTGGCTAGATGG
ATATGAGACCCGCCGCCGTCTCCAGATTGTGGCGGAGGTGGAACTCTCGGCCCCCGCGCCAGTCCCCGCGGCC
AGCGCATCCCGCCATGCGGGTTGTTGGCTGGTGCATCGCGCGGGTGTGCTATGAGTGTGGAAACACTATGTCG
CGTGTCGTGCTGAGGTCTGTTGAGAGGTTTCGTCGTTTGTGCATGTCCTGTCCCGGTTGGAGTTTGAGCGAGGT
GGTTCAAAGTTTTTGGATCGCGTGGGAGAGACTGAAACGGTTTGGTGAGAATGGTTGAGACAGAGGTTGGGC
TTGGAAACTGGAGGAGAGGAGCAGCGTAACTCGAGGACGATGCAGTAGATGCACCACAACAGTTGTGGTGGG
CGCCTGGAGTAACACGCGTGCCACCAACACGCAATTACAGAGATCCGTCATACAGGAGGGATCATATGCGATTTA
ATTTTGGTTTTGCATTTGTAAGACGTTTTCACA
```

FIG. 2E

Information on zeaxanthin epoxidase (ZEP) gene of Chlamydomonas wild-type and ZEP genes in ZEP mutants 1, 2, and 3

CreO1.g052550.t1.2
Zeaxanthin epoxidase, chloroplast precursor (ABA1) (NPQ2) (PMID: 12871093). Previously annotated as ZEP >ZEP Mutant 3 ZEP gDNA sequence     5' UTR / CDS / 3' UTR / Target sequence
                1bp Insertion                                (Indel sequence)

```
GCGACGCACGGCTGGGCCAAATTCGCCAACGGCAGGAGACCAAATCGATCGAGGCGATCTTGCGAAGTTCTCG
GACAAATCGATCGCACCCATAGTGATTTAAGCATTACATTTGCCCAAGGCGTGAGAAGTGCGAGGCCCGAACGG
CTATGACGCCAATGCGCAGCTTACGACATTTAAAGCAAATTATTCATACATCATACAGCACGCTTATGTGAAGAAA
GCCAGGATTTTAGGCTCTCGCCCCGATCAAGACGATCTCCCCATTGCGAAGTTCTCGGTTTCTTTCCGGTTCGCCT
GCTCCGTATGATTTACCTTTGCGCTACAACAGCGACTTAAACGACCTACGTCGCCTTACTGTGTGCGCGTACGTGT
TTGTAGCTGTGAGATAGTTTTGTCCGCAGCGTACCCGCAAATAGAATGCTCGCGAGCACTTACACGCCCTGTGGC
GTTCGCCAGGTGGCAGGCCGCACGGTTGCAGTGCCCAGCAGCTTGGTCGCGCCAGTGGCAGTCGCTCGGTCG
CTGGGGTTGGCGCCCTACGTCCCTGTATGTGAGCCTTCTGCGGCGCTTCCGGCCTGCCAGCAGCCTAGCGGGGC
TCGTCATGTTCAGACTGCTGCCACTCTCCGTGCCGACAACCCCAGCTCGGTCGCGCAGCTGGTGCATCAGAATG
GAAAGGGGATGAAGGTTATTATCGCCGGCGCGGGCATCGGCGGCCTGGTGCTAGCCGTTGCACTTCTGAAGCA
GGGCTTCCAGGTTCAGGTCTTTGAGCGCGACCTGACGGCCATCCGCGGCGAGGGCAAGTACCGTGGACCCATC
(A)CAGGTGCGTTCGCCGGAACACCAACGCGCTTGTTTTTGCTGTGCCGCGACCATGAACTAGGCCTTATCTTGA
GGTGTTAGCATGTTTAGCCAGCGTTGGATCTGTGTGGCGAGGTTGGGGTGAGAACCCTTCCTGTGTACCTGCTC
GGGCGTACCTTGTGCCCCACCGCTGACTGGCTTACTTAATGACAAAACGCAGGTTCAAAGCAATGCGCTCGCTG
CGCTGGAGGCTATCGATCCCGAGGTGGCCGCGGAGGTGCTGCGCGAGGGCTGCATCACTGGCGACCGTATCAA
CGGGCTCTGCGACGGCCTGACTGGCGAGTGGTGAGTAGGCAATCCAGCTGTGCATCCAGTCGCGCGGTTGCGG
AGGTCGTCTCGGGAAACGCGACGTGGCGTCCACTCGCCCAAGGAGTGGTCTCCCGCAGCGTGGTCTCCCGCAG
CTCGGGTGCAACACCCTGCCCCCTGCCGCGAGCGCGCTGCGCTTGCTTATGTTGCGCAGCGGTGTGAGTTACAA
CAGCTTCTGTTGAAGAGCTGTCATACGAAGCACGGCGCGCTGTGGCGCTGCAGCCGTGCTGTGGAAACTCCAA
CACCTCCACCGCCAGCCTGCGCACGCACACGCAATACACTCGCCTCGTGTGCCCCCTCCTCACACAACGGCATGT
GACACTCAGTTTTAACTCTTATTTTGACAGCTGAGAGCTACACGCTTGGGTGAATGGGGAGGTCCTTGATGTTTC
GTTGCACTCCGTGGCTCCGGAGTCCGTGCGGACCGTCACCCACAAATGGGAGCGACGGCTTTCTTGTGCTGTC
TGCCCCGTTAGCCACTAACTGCGAATGACCTTGACAGTTTACTTTGCTATTTTTCCTTCCAGGTACGTCAAGTTCG
ACACGTTCCACCCGGCGGTCAGCAAGGGCCTGCCGGTGACCGCGTCATCAGCCGCCTCACGCTGCAGCAGAT
CCTGGCCAAAGCCGTGGAGCGGTGAGCCGTGCGCGCGGTGTGATGGCTTTAGCGTCAGTGCTAGCATGGGGG
TTGGTGGGTGGTAATCGCGGCGCCCATGGCCGGGTAGCAGCGGCCGAAAGCTGGCGCAGAGCGCGCGTTGGA
CAAGCGGTCCTGTTGCCGGTATGGGCACGAGCAGGGCGCTGGTGCGGGCAAAGGGCAGAGTGGAGTTGCAG
AGCAGCGCTGGCGTCGGCTGTGCGCTCTCCAAATGGCCTCGTGGCATTCTGACGGGACACATCCTGGAAAATAG
TAGCGCACCCAACTGCTGGTGGCTCCTCGTACAATCCCCCCAATTTACAATCGCTCGTTCTGGCTCGCAGCTACG
GCGGCCCCGGCACCATCCAGAACGGCTGCAACGTGACCGAGTTCACGGAGCGCCGCAACGACACCACCGGCA
ACAACGAGGTGAGAGCGTGCTAAGAAGAGCATGCACGTGGAGCGTGTAAAATTGTGTGGCCTGAAGCGGCAG
TGCCTGCGGCATGGACTAGGTGGTTGCAGCATGCTGCGCGCGTGGGTTGCCGGTCAGGAAACGCCGGACCG
AGCCGCGCAGATTCAGTCAGGAGCGGATTAGGAAGTTTGAAAAACAGGGTTCGGAGTGTGCAAGCGGGCTCA
GGAGCTGTGGTGCCTTTCTACACCGGTCGCCCTACCAGGCACCCACTGAAACTGTAAAACCGTTGCTGCGCCGG
CGATGCCCTCTACTTCACTAGGTGACTGTGCAGCTGGAGGACGGGCGCACGTTTGCGGCCGACGTGCTGGTGG
GCGCCGACGGCATCTGGTCCAAGATCCGTAAGCAGCTCATTGGCGAGACCAAGGCCAACTACAGCGGGTACAC
CTGCTACACCGGTGAGATTATTGACCTTCAAGTTGGAAGGAGGGAGCGGGGGAGCGGAATGGAAGGAAGC
AGCGTGGACGGGGCGCACGGAGGGGAGGGGACTGCGGGTCATAGCGCCGCCTTGCGGGGCGTGAGGAGTG
TTGGGCGGATATTCAGTTTTCTTTGCCCAAGATCTTCCCACAATCCGCGTGTGTCTGACGCGGGATGTGGCCCCT
GCTGCCATGGCTTCGCAGGCATCTCGGACTTTACGCCGGCGGACATTGACATTGTGGGCTACCGCGTGTTCCTG
GGCAACGGCCAGTACTTTGTCAGCAGCGACGTGGGCAACGGCAAGATGCAGTGGTGAGCGGCGGCGGGCGG
GCGAGCGAGGGCTGCGGGGTCTGGAGGGTGTGTACCGGGCGGAAGGGAGGGGAAGGGAGGGGAAGGGAA
GGCAGGATGCAGGCGAGGGCAGGATGTGAT
```

FIG. 2F

```
GGTGGGAAGAGGGCGTGGCGAGCAGCAACTGGAAAGGTGGTGGGTAAAAAAATGGTCCATGAATATGGCTC
GGTACAGTTCAAAGCATGGAAATGGAACCCGCCGTCTGCTGCACCATGGGCGTGAGCGGGGAGTACGCGACTC
CTGGACAGCCGTAACAATGCGGATGGCCTCAACAAGCCAGGAGCGGCACGAACCCAGCTCACGAGCGCACAG
CGTGCCAGGACGGCGGCCGGCAAGGATGAAATGTTTTTCCTAATATAAATGCGGACTCCTGACGCATTATATCCA
TTTTGCCACTGAGCCAAAGACACATATATACACGTGCGCCGCCGTCCTGCGCCACAGCCGCCTAGCGCTCCGGCC
GCGCCCGGTTCCCTCGGCGTCATGCGCTGGAGCCCCCTCGCACCCTGCACCGCAAAGCCCATCAACACCACACT
CGTCCCCACACCGCGAGTCACCGCCACTGCACTCGCTGTCCCTCAACCCGTCACAATCTCGCCGACACGCGATAA
CGAACCCACGCAGGTACGGCTTCCACAAGGAGCCGTCTGGCGGCACCGACCCCGAGGGCAGCCGCAAGGCGC
GCCTGCTGCAGATCTTTGGCCACTGGAACGACAACGTGGTGGACCTGATCAAGGCCACGCCCGAGGAGGACGT
GCTGCGCGCGACATCTTTGACAGGTACGGAAAAAGGGAGAGCGGGGTGGCTGGAGGGCGGGAAAGGGCG
AAGGGGCGGAGAAAGAAATGACTAGGGGATGGTGTTCATTTGTGGGATTGAGAGGGGTCCGCGGATCCCGGC
AGAGGGCGCCAGTGGCAAGGCGTGGGAGTCGCGGGGCGGACAATGCTGGGCCAGGGGCGCCTAGTCACCCC
GGGACACTGTCTCAGTATGCCGCCGTCCCGGCCGCGCCGCACAGGCCGCCCATCTTCACCTGGAGCAAGGGCC
GCGTGGCCCTGCTGGGCGACAGCGCGCACGCCATGCAGCCCAACCTGGGCCAGGGCGGCTGCATGGCCATTG
AGGACGCCTACGAGCTGGCCATCGACCTCAGCCGCGCCGTGTCCGACAAGGCCGGAAACGCGGCGGCGGTGG
ACGTGGAGGGCGTGCTGCGCAGCTACCAGGACAGCCGCATTTTGCGCGTCAGCGCCATTCACGGCATGGCGGG
TGAGAGCTGCAACCAGCGTAGTCGGGCTGGGCTGCTGTGGGCAGGGTCGGGTTGGGTTGGGCGCACGTGGG
CGGCGAGTGTATGTGCAGTGTGACGTGCACACTATCATAATACTTTATGCTCACCGCACCGCGCCGCGCCGCACC
ACGCGCCACAGGCATGGCTGCCTTCATGGCCAGCACCTACAAGTGCTACCTGGGCGAGGGCTGGAGCAAGTGG
GTTGAGGGGCTGCGCATCCCGCACCCCGGCCGCGTGGTGGGGCGGCTGGTGATGCTGCTCACCATGCCCAGCG
TGCTGGAGTGGGTGCTGGGCGGCAACACCGACCACGTGGCGCCGCACCGCACCAGCTACTGCTCGCTGGGCG
ACAAGCCCAAGGTGAGCGGCTGCCGGGCTGGGGGGGGGTGGAGGGAGAGGAGGAGGATTGCGGGGA
GACGAGGGAGGGCAAGGCAGGCGCTGCCTTCGTGGATGCACCGCCCCGTCGTTAGCAGGACCTCAGGAACTC
GTCCCCAAAACCACAACAGAACCCCCAATATCGCCTCTTCCTTCACTGCTTGTCACGCCTGGTCCGCCGACCGCA
GGCTTTCCCCGAGAGCCGCTTCCCCGAGTTCATGAACAACGACGCCTCCATCATCCGCTCCTCCCACGCCGACTG
GCTGCTGGTGGCGGAGCGCGACGCCGCCACGGCCGCCGCCGCCAACGTGAACGCCGCCACCGGCAGCAGCGC
CGCCGCGGCCGCCGCCGCCGACGTGAACAGCAGCTGCCAGTGCAAGGGCATCTACATGGCGGACTCGGCGGC
CCTGGTGGGCCGCTGCGGCGCCACCTCGCGCCCCGCGCTGGCCGTGGACGACGTGCACGTCGCCGAGAGTCA
CGCGCAGGTCTGGCGCGGCCTCGCCGGCCTCCCCCCCTCCTCGTCGTCCGCCTCCACCGCCGCCGCCTCTGCGT
CCGCCGCCTCCTCTGCCGCCAGCGGCACCGCCAGCACCCTGGGCAGCTCGGAGGGCTACTGGCTCCGCGACCT
GGGCAGCGGCCGCGGCACCTGGGTCAACGGCAAGCGCCTGCCCGACGGCGCCACGGTGCAGCTGTGGCCCG
GCGACGCGGTGGAGTTCGGCCGGCACCCCAGCCACGAGGTGTTCAAGGTGAAGATGCAGCACGTGACGCTGC
GCAGCGACGAGCTCAGCGGCCAGGCCTACACCACGCTCATGGTGGGCAAGATCCGGAACAACGACTACGTCAT
GCCCGAGTCGCGGCCGGACGGCGGCAGCCAGCAGCCGGGCCGCCTGGTGACGGCTTAAGCGGCGCCGTGCG
TAAGGGCCGGCTTACGGGGGCGGCAGTGTCGCTGTGGAGGGATGGTCTGGGGTGGGAGGAATGGGAGGAG
AGCGGCGGGAGCCCGAGGAGCGGAGCGCTGGAGGCTTGCGGAGCGGCAGCTTGGGAAGAGCTGCGGAGA
GAGGAAGGAGCGCAGGGCGCTTGGAGCACGCGCCAGATTACGATCACGGCAGCGCGAGGCGCGCGTCTGAC
TTCGAAGTGGTAAGGAAGATTTCATGTATGATTGCGTCGAGGGACACCGCAAGTTTTACGCGCGGCGGAGGGA
GCCTTGGGGCATACAACAGTACGAGCGGGCGTTGGTGAGAAGGTGGTCACTCCGTATGAGAAGATGGTTACTC
CGTACCTTCGTGAGAAGCTGCTGCGCACAAGTTACGAACCTATCTGTGTGGAGAGCCCGGTAGTATATCAGGGG
CGAGGGTCATGAACGCGAGTGGCGAGTCTGTGAGCGCCAATTTGTTATGCGGCATAATTTCGCATCGGGGTATT
ACGTCTACAAAATGTTGAGCTGGCTTAGCGCAGGAGGCAACACCTCAGGCAGAATGTACGAATGTGTGCAGAA
GGGCAGAGTCAAGGCAGAGGCGGAGAAGTTGTCAGGGCTGTGTGTGGTTTGGTCAGGGCGTGGCTAGATGG
ATATGAGACCCGCCGCCGTCTCCAGATTGTGGCGGAGGTGGAACTCTCGGCCCCCGCGCCAGTCCCCGCGGCC
AGCGCATCCCGCCATGCGGGTTGTTGGCTGGTGCATCGCGCGGGGTGTGCTATGAGTGTGGAAACACTATGTCG
CGTGTCGTGCTGAGGTCTGTTGAGAGGTTTCGTCGTTTGTGCATGTCCTGTCCCGGTTGGAGTTTGAGCGAGGT
GGTTCAAAGTTTTTGGATCGCGTGGGAGAGACTGAAACGGTTTGGTGAGAATGGTTGAGACAGAGGTTGGGC
TTGGAAACTGGAGGAGAGGAGCAGCGTAACTCGAGGACGATGCAGTAGATGCACCACAACAGTTGTGGTGGG
CGCCTGGAGTAACACGCGTGCCACCAACACGCAATTACAGAGATCCGTCATACAGGAGGGATCATATGCGATTTA
ATTTTGGTTTTGCATTTGTAAGACGTTTTCACA
```

FIG. 3A

| | total | mut | freq(%) | total | mut | freq(%) |
|---|---|---|---|---|---|---|
| RGEN1 | 4276 | 4 | 0.094 | 9541 | 0 | 0 |
| RGEN2 | 16734 | 6 | 0.036 | 19060 | 0 | 0 |
| RGEN3 | 16888 | 77 | 0.456 | 30992 | 0 | 0 |
| RGEN4 | 20274 | 9 | 0.044 | 17138 | 0 | 0 |
| RGEN5 | 15398 | 17 | 0.11 | 7867 | 0 | 0 |

FIG. 3B

[FIG. 4]
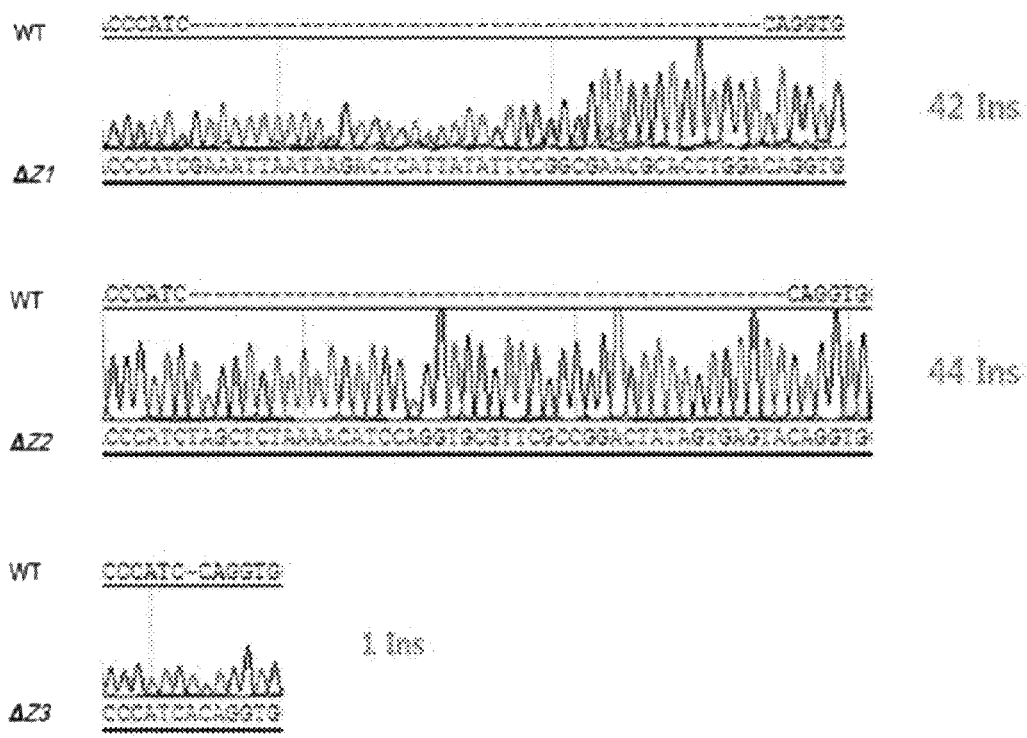

[FIG. 5]

SpCas9 Sequence
MGSSHHHHHHVPYDVPDYAELP▓▓▓▓▓GIRIPGEKPDKKYSIGLDIGTNSVGWAVITDEYKVPSKK
FKVLGNTDRHSIKKNLIGALLFDSGETAEATRLKRTARRRYTRRKNRICYLQEIFSNEMAKVDDSFFHRL
EESFLVEEDKKHERHPIFGNIVDEVAYHEKYPTIYHLRKKLVDSTDKADLRLIYLALAHMIKFRGHFLIEG
DLNPDNSDVDKLFIQLVQTYNQLFEENPINASGVDAKAILSARLSKSRRLENLIAQLPGEKKNGLFGNLIA
LSLGLTPNFKSNFDLAEDAKLQLSKDTYDDDLDNLLAQIGDQYADLFLAAKNLSDAILLSDILRVNTEIT
KAPLSASMIKRYDEHHQDLTLLKALVRQQLPEKYKEIFFDQSKNGYAGYIDGGASQEEFYKFIKPILEKM
DGTEELLVKLNREDLLRKQRTFDNGSIPHQIHLGELHAILRRQEDFYPPLKDNREKIEKILTFRIPYYVGPL
ARGNSRPAWMTRKSEETITPWNFEEVVDKGASAQSFIERMTNFDKNLPNEKVLPKHSLLYEYFTVYNE
LTKVKYVTEGMRKPAFLSGEQKKAIVDLLFETNRKVTVKQLKEDYFKKIECFDSVEISGVEDRFNASLG
TYHDLLKIIKDKDFLDNEENEDILEDIVLTLTLFEDREMIEERLKTVAHLFDDKVMKQLKRRRYTGWGRL
SRKLINGIRDKQSGKTILDFLKSDGFANRNFMQLIHDDSLTFKEDIQKAQVSGQGDSLHEHIANLAGSPAI
KKGILQTVKVVDELVKVMGRHKPENIVIEMARENQTTQKGQKNSRERMKRIEEGIKELGSQILKEHPVE
NTQLQNEKLYLYYLQNGRDMYVDQELDINRLSDYDVDHIVFQSFLKDDSIDNKVLTRSDKNRGKSDNVP
SEEVVKKMKNYWRQLLNAKLITQRKFDNLTKAERGGLSELDKAGFIKRQLVETRQITKHVAQILDSRMN
TKYDENDKLIREVKVITLKSKLVSDFRKDPQFYKVREINNYHHAHDAYLNAVVGTALIKKYPKLESEFVY
GDYKVYDVRKMIAKSEQEIGKATAKYFFYSNIMNFFKTEITLANGEIRKRPLIETNGETGEIVWDKGRDF
ATVRKVLSMPQVNIVKKTEVQTGGFSKESILPKRNSDKLIARKKDWDFKKYGGFDSPTVAYSVLVVAK
VEKGKSKKLKSVKELLGITIMERSSFEKNPIDFLEAKGYKEVKKDLIIKLPKYSLFELENGRKRMLASAGE
LQKGNELALPSKYVNFLYLASHYEKLKGSPEDNEQKQLFVEQHKHYLDEIIEQISEFSKRVILADANLDK
VLSAYNKHRDKPIREQAENIIHLFTLTNLGAPAAFKYFDTTIDRKRYTSTKEVLDATLIHQSITGLYETRI
DLSQLGGD*

6xHis
HA tag
▓▓▓▓▓▓▓▓
SpCas9

[FIG. 6a]
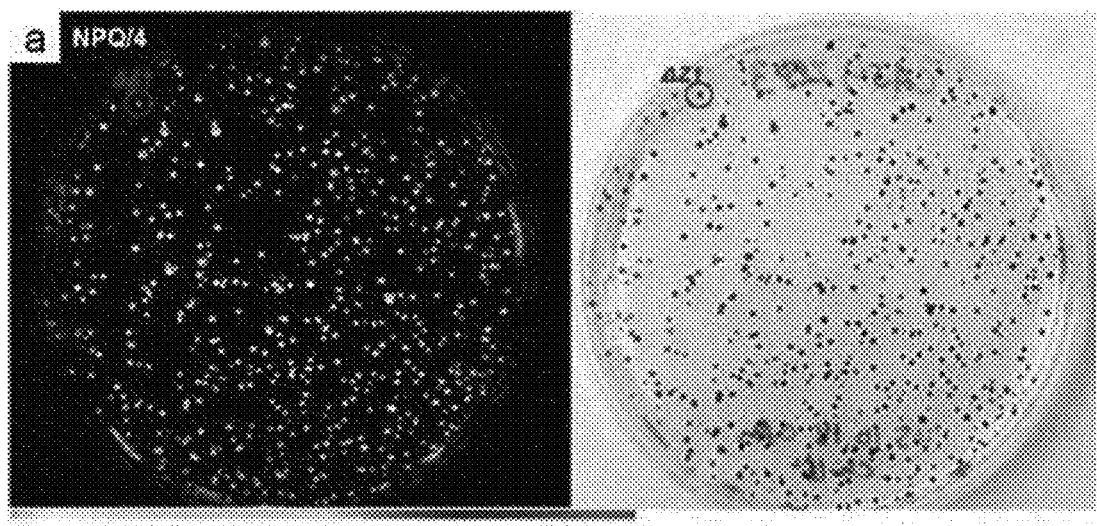
[FIG. 6b]
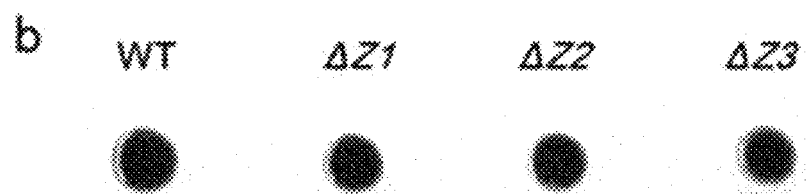

[FIG. 6c]

FIG. 7A

Cre03.g188250.t1.2
AGP-glucose pyrophosphorylase small subunit (GLGS); Catalytic subunit catalyzes the formation of the glucosyl nucleotide from ATP an...

>Wild type - AGP gDNA sequence    5' UTR / CDS / 3' UTR / Target sequence

```
CAGGGTTTGCTTTTGGGCACGACTTGCATTGTGTACTTGTTTGTGACCTGAGGTCGAGGACCTTCTT
CTAGGTAGTCAAAACAGAGGAAGACCGATCCTTAGCATGGCCCTGAAGATGCGGGTGAGCCAGCG
CCAGGCGCTGGGCTCGCAGACCTTCGTCTGCCCCACGGTGCGTGGCATGAACAGCGTTTTATGTC
GACTTGGGCCGGAGCGCAGCGGACTCAACCGACTCATCTCGCAGGCTCAGTGGTGCGCAAGGCC
GTGAGCTCCAAGGCCCGCGCCGTGTCGCGCCAGGCTCAGTAAATGGATCATGCATTCGCACATGC
ATTTGGGCGACGTCACTGCGACTTACCGGGTCGCCTTATCGCAGGTCGTTCGGGCTCAGGCTGTGT
CGACCCCCGTTGAGACCAAGGTCGCGAACGGGGTGGCCGCATCCTCTGCTGCGGGCACTGGGCA
GAACGACCCGCTGGCGACATCAGCAAGGTATGCTCGCGCTGGCCCATTTGATGCTTCCGGACTCG
TCGATGTGACCGTCCCGCCATCTCGTTGCCGATGCAGACGGTGCTGGGTATTATTCTGGGTGGTGGT
GCCGGCACCCGTCTGTATCCTCTGACCAAGAAGCGTGCCAAGCCGGCGGTGCCCCTGGGCGCCAA
CTATCGCCTGATCGATATTCCCGTTAGCAACTGCCTGAACAGCAATGTCACCAAGATTTACTGCCTCA
CCCAGTTCAACTCGGCGTCGCTGAACCGCCACCTGTCCCAGGCCTACGTGAGTACCTTGTGAATACT
GAAACTGCGGGCTCGGGCTCGGGCGACATAGCTGTCGGCCGACCGCAGAATGCGTCGCCATGCG
GACTCGGCGCAACACCTGTCGCGTGTCACTCCCGCTAGGGCACAGGAGCGAACCAGCCCTCCAGG
CGGCTTAATCCATCAGGGAGACTGTATGTTCAGATGGAAGGGACACAAGGGCGGGGCTGCGAAA
GCTTTCAAGTACACACGTGTGGCATCATATGCTCTACCAGCGCACAGCGCCACCGCACACCGTACCG
CGTCCACATCCACCTCTTGCCATCCCACCCCTCTCCCATCCTCCCACCCTCCCATCCTCCCACCCTCCC
ATCAACCCCATCAACCCCACCCCACCACCCTCCCCTCTCTCCGCTCCCCCTCTCGCACAGAACTCGTC
TGTGGGCGGCTACAACAGCCGCGGCTTCGTGGAGGTGCTGGCGGCCAGCCAGTCGTCCGCCAAC
AAGAGCTGGTTCCAGGGCACCGCCGACGCCGTGCGCCAGTACATGTGGCTGTTCGAGGAGGCGG
TGCGCGAGGGCGTGGAGGACTTCCTCATCCTGTCGGGTGAGTGGGCAGGAAGAGGGGTGGAGA
GGGGGAAAGTTGGGGGTGGGTGCACGGAATGGGTGGGAAGGGGGGGTTTCCTCCTGCGCAAG
GCAGCGAGGCGAGAAGGTTGAGGCCGCCGTAACTGGGGGTGGTGGAGTGGGCGGGTGAGGCG
CATGTTGAATGGGGCATGGAAGACTGGTGGGTGGGTGAGTGGAGAGGCGAAGTTTCGGAGGGT
GCCGGAAAGGGCATGGCCGGTGCAGGGTGCCACTGGGCACGGTGGCCTGCCGTCAAGCGGGCGT
GTTGGGCAGCGGGACTGCGCGCTGCAGCAGCCGGCACAGATACGGAGCGCACGGCAGGACGAC
ACGCGGGGCAGCCGGCGGGCTGGTCGGTCGGTGTGCTGGGGGCAGCAGCGACGCGCTGGTACA
CGGAGGGCTACGAGTGCTGCACAGCCAGCCTCGGCACACAACAGCCACCAGTACGGCATGTAGCA
CCACGCGTCTGGCTTACCAGTATCAGCGCAGTAGCGGACCAATGGGGGCGGCACGGAACGCGTGT
GTGCGGATGGGCTGCGGCACCGCCAACCGGACGACTCCCAAACATCACATCCTCCCCCCTCCTCCA
GGCGACCACCTGTACCGCATGGACTACCGCGACTTTGTCCGCAAGCACCGCAACTCGGGCGCCGC
CATCACCATCGCCGCGCTGCCCTGCGCGGGAGAAGGAGGCCAGCGCCCTTCGGCCTGATGAAGATCG
ACGAGGAGGGCCGCGTGATCGAGTTCGCGGAGAAGCCCAAGGGCGAGGCGCTGACCAAGATGC
GCGTGGACACCGGCATCCTGGGCGTCGACCCCGCCACGTGAGTGTGTGCGCGCTGGTGTTGGTTG
ACATGGTGGTATGGTGGTGGTGTGTGGGTGGGTGTTGGGTGGTGGGTGGGAATTGGAGGTGCTA
TCATGGTGGGTATGTTGGGGAGTTCGGAGGATGCGGTCTGTGGGGATATGGTTCCAGGGCTAATG
GGTCTGGGATGGGTCAAGGTGGAGGGGTGCGCGGTGTGCGTGTGGCGTGGAGAGCGGCAGTTG
GGTGCGGCACCGCAGCGGCGGCAACGCAGCAGCATAGGCGGCGAGGACGGCGGCGGCGCTCCA
GCGGGCAGCGAGCCACGGCGGCGGCAGCTCAGACCAGCACCGCCAGGGCCCAGCAGCGCAGTG
CAGCCAGCAACAGCGCTGGTGCTACTGCTGGTGCTACTGCTGGGAATGCGGCTGTTGTGGGCGTC
GAGCAGTAGTGACCATCACCGGCACTGCGCTGCGGCAGCCGGCCTGCCATCCAGCATGGCGCCGC
GGGGCTGGGTGCGCAAGCGAAAGGCAGCAGTGGTGGACAGAGCTGTTGAGGCACGGCGCCTGA
CTGCCCGGTGGTGACGATGTGCGGATGCTCGCGCCCAGCAGAAGGGACCAGGACCCGGCTGGTG
GCCGCCGCCGCCGCCGCAGCAGCAGTCGCCACGTAGCACGCAGCGGCTACAGCAGCAACCGGCG
CCCACACCCGCACCACAACCCCAGCCACCGCACCAGCCAAACACACGCACCCTTCCCTCTCTCCCCC
```

FIG. 7B

```
TCTCCTCACACGGCCCGCACTGACCTGTCCCTCCCCGTCTCCCTCTGCTCCCCCTCCGCCACCTCAGC
GCCGCCGCCAAGCCCTACATCGCCTCCATGGGCATCTACGTCATGTCCGCCAAGGCGCTGCGCGAG
CTGCTGTTGAACCGCATGCCGGGCGCCAACGACTTCGGAAACGAGGTCATCCCCGGCGCCAAGGA
CGCCGGCTTCAAGGTGCAGGCCTTCGCCTTTGACGGCTACTGGGAGGACATCGGTACCGTGGAGG
CCTTCTACAACGCCAACCTGGCGCTGACCGATCCCGAGAAGGCGCAGTTCTCGTTCTACGACAAGG
ACGCGCCGATCTACACCATGTCGCGCTTCCTGCCGCCCTCCAAGGTGATGGACTGCGACGTGAACA
TGTCCATCATCGGCGACGGCTGCGTGATCAAGGCCGGCTCCAAGATCCACAACTCCATCATCGGCAT
CCGCTCGCTGATCGGCTCCGACTGCATCATCGACAGCGCGATGATGATGGGCTCGGACTACTACGA
GACCCTGGAGGAGTGCGAGTACGTGCCCGGCTGCCTGCCTATGGGCGTGGGCGATGGCTCCATCA
TCCGTCGCGCCATTGTGGACAAGAACGCGCGCATTGGTCCCAAGTGCCAGATCATCAACAAGGACG
GCGTCAAGGAGGCCAACCGCGAGGACCAGGGCTTCGTGATCAAGGACGGCATTGTCGTCGTGATC
AAGGACTGCACATCCCCGCCGGCACCATCATCTAAACGTGATGGCTCGGGCCGGGAAGAGGCGG
CGCGGCGCAGAGCCGGCCGGCGCGGCGGCAGCCGGCGGCGCGCGGCGTGTGGCGGAGACGTT
GGTGATGGAGAGCAGACGGAGGTGGCGGGACCTCAGGCACATTTCGGCAGCTGCCGCAGCGAG
GAGCAGGGAGAGCGAGCGTGTGTGGGTGCACACGCTAGCGCGCACTCACGACCTGCAGCAGCAG
CAGCCGTGGCGGAGATGGCGGGAGCTGCTCGGGTACTGTTGAAGCGAGGCGGGCCCTTGGCTGC
GTTTTTGGGTTGGAATGTTGCGCAGTGACGGGACTCTATAGAGTAGGGGGGATTGAGTGTCCTTG
GTTCGGGTGAACGCCATGGACCGGTGCGGCACGGCGTGGCGTGGCACTGCGTTGCTGCGGAAGC
GCAAGCTGCGGCCTTCCCGCAACGGTGCAGCAGCCGCATCGGACGCAACACCCCAGGAGCGGCA
GTAGCTGCCAGTCGCGTGCGGCTGTTTTGAGGGAGAGCGCTTTTTCGGGAGCGTGAACGGTCGG
ACCAAGCACCGGCGGTGGCAGCGGCAGGCCTTCGGCCCCCCGGCCCTTAAAGCTGCCGGCGCCA
AGGCACGCCGCGAGGCGTGTGTGTTCCCGAGGTGCAGCCGGGCGGTGGCGGCTGCAGGGTGGG
TGCAGCCAGCTGGCGTGCCATCCAGCACGGCGGCGGTTGTTGCGGCTCGGCGGTGGGGAAGGT
GGAGCACTGAGCGGGCGTGGGTCGGGACGCTTCGCGGCTCACGCGGCGGTTGGCCGTTGCGGC
TGCCTTCCGTGGGATGCCGTAGGAGGGGCGGGTCCTTACTCGCTCGCGTCCCACCTGGGGGTTG
TAGTTTCTTAATTTAGCGTGTACCATGCTCAACATTGTTTGACTCCCCCAGACCCTGCGAACCTGCAT
CTGCGGAGGTAGAGAGGGCTCTTGGGTGTGTGCAGATTTTTGGTTGTTTGGTTTGGGTGATGGTG
CAACAGTTTTGCGCGTGGCGAGTGTGTGCGTTCTCAGATGAGGAGAATTGTTTGTGCTATGCAGAG
TTGAGGCGAGAGGAAGACTTTTGGGCACGACTGCACCGTGCATCCATGGAGCACAGCTGCATAGA
AGCACGTGGGCAACGCACGGCTTGCACCGTCCGATGCATCGTCCCCTCCCCCAGAGATTTGGACCG
AGAGAAGAAATCCAGCACATGTAAACTCGTATGAGG
GCA
```

[FIG. 8a]
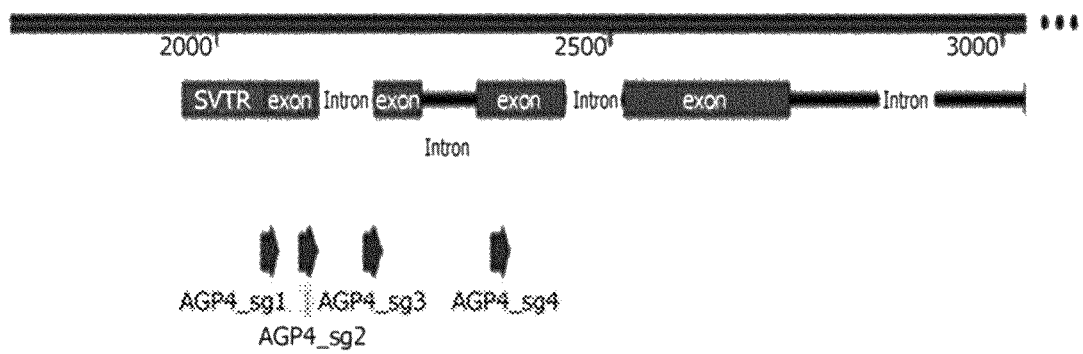
[FIG. 8b]
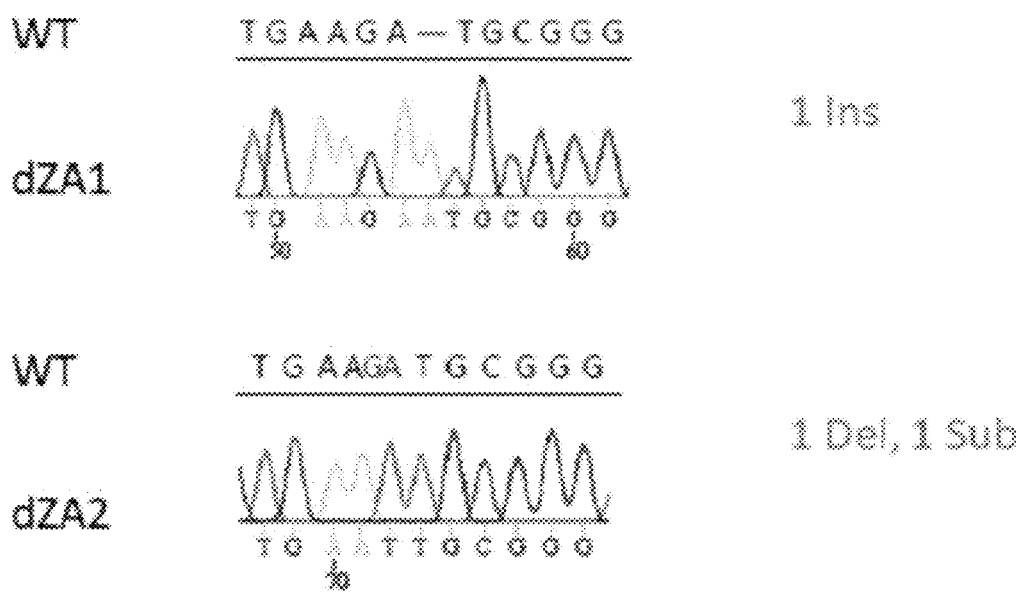

FIG. 9A

Cre03.g188250.t1.2
AGP-glucose pyrophosphorylase small subunit (GLGS). Catalytic subunit catalyzes the formation of the
glucosyl nucleotide from ATP an...

5' UTR / CDS / 3' UTR / Target sequence
(Indel sequence)

>Double ZEP/AGP mutant 1 (dZA1) - AGP gDNA sequence    1bp Insertion

CAGGGTTTGCTTTTGGGCACGACTTGCATTGTGTACTTGTTTGTGACCTGAGGTCGAGGACCTTCTTCTAGG
TAGTCAAAACAGAGGAAGACCGATCCTTAGCATGGCCCTGAAGA(A)TGCGGGTGAGCCAGCGCCAGGCG
CTGGGCTCGCAGACCTTCGTCTGCCCCACGGTGCGTGGCATGAACAGCGTTTTATGTCGACTTGGGCCGG
AGCGCAGCGGACTCAACCGACTCATCTCGCAGGCTCAGTGGTGCGCAAGGCCGTGAGCTCCAAGGCCCGC
GCCGTGTCGCGCCAGGCTCAGGTAAATGGATCATGCATTCGCACATGCATTTGGGCGACGTCACTGCACTT
ACCGGGTCGCCTTATCGCAGGTCGTTCGGGCTCAGGCTGTGTCGACCCCGTTGAGACCAAGGTCGCGAAC
GGGGTGGCCGCATCCTCTGCTGCGGGCACTGGGCAGAACGACCCGGCTGGCGACATCAGCAAGGTATGCT
CGCGCTGGCCCATTTGATGCTTCCGGACTCGTCGATGTGACCGTCCCGCCATCTCGTTGCCGATGCAGACGG
TGCTGGGTATTATTCTGGGTGGTGGTGCCGGCACCCGTCTGTATCCTCTGACCAAGAAGCGTGCCAAGCCG
GCGGTGCCCCTGGGCGCCAACTATCGCCTGATCGATATTCCCGTTAGCAACTGCCTGAACAGCAATGTCACC
AAGATTTACTGCCTCACCCAGTTCAACTCGGCGTCGCTGAACCGCCACCTGTCCCAGGCCTACGTGAGTACC
TTGTGAATACTGAAACTGCGGGCTCGGGCTCGGGCGACATAGCTGTCGGCCGACCGCAGAATGCGTCGCC
ATGCGGACTCGGCGCAACACCTGTCGCGTGTCACTCCCGCTAGGGCACAGGAGCGAACCAGCCCTCCAGG
CGGCTTAATCCATCAGGGAGACTGTATGTTCAGATGGAAGGGACACAAGGGCGGGGCTGCGAAAGCTTTC
AAGTACACACGTGTGGCATCATATGCTCTACCAGCGCACAGCGCCACCGCACACCGTACCGCGTCCACATCC
ACCTCTTGCCATCCCACCCCTCTCCCATCCTCCCACCCTCCCATCCTCCCACCCTCCCATCAACCCCATCAACCC
CACCCCACCACCCTCCCCTCTCTCCGCTCCCCCTCTCGCACAGAACTCGTCTGTGGGCGGCTACAACAGCCG
CGGCTTCGTGGAGGTGCTGGCGGCCAGCCAGTCGTCCGCCAACAAGAGCTGGTTCCAGGGCACCGCCGA
CGCCGTGCGCCAGTACATGTGGCTGTTCGAGGAGGCGGTGCGCGAGGGCGTGGAGGACTTCCTCATCCTG
TCGGGTGAGTGGGCAGGAAGAGGGGTGGAGAGGGGGAAAGTTGGGGGTGGGTGCACGGAATGGGTGG
GAAGGGGGGGTTTCCTCCTGCGCAAGGCAGCGAGGCGAGAAGGTTGAGGCCGCCGTAACTGGGGGTGG
TGGAGTGGGCGGGTGAGGCGCATGTTGAATGGGGCATGGAAGACTGGTGGGTGGGTGAGTGGAGAGGC
GAAGTTTCGGAGGGTGCCGGAAAGGGCATGGCGGTGCAGGGTGCCACTGGGCACGGTGGCCTGCCGTCA
AGCGGGCGTGTTGGGCAGCGGGACTGCGCGCTGCAGCAGCCGGCACAGATACGGAGCGCACGGCAGGA
CGACACGCGGGGCAGCCGGCGGGCTGGTCGGTCGGTGTGCTGGGGGCAGCAGCGACGCGCTGGTACAC
GGAGGGCTACGAGTGCTGCACAGCCAGCCTCGGCACACAACAGCCACCAGTACGGCATGTAGCACCACGC
GTCTGGCTTACCAGTATCAGCGCAGTAGCGGACCAATGGGGGCGGCACGGAACGCGTGTGTGCGGATGGG
CTGCGGCACCGCCAACCGGACGACTCCCAAACATCACATCCTCCCCCCTCCTCCAGGCGACCACCTGTACCG
CATGGACTACCGCGACTTTGTCCGCAAGCACCGCAACTCGGGCGCCGCCATCACCATCGCCGCGCTGCCCT
GCGCGGAGAAGGAGGCCAGCGCCTTCGGCCTGATGAAGATCGACGAGGAGGGCCGCGTGATCGAGTTCG
CGGAGAAGCCCAAGGGCGAGGCGCTGACCAAGATGCGCGTGGACACCGGCATCCTGGGCGTCGACCCCG
CCACGTGAGTGTGTGCGCGCTGGTGTTGGTTGACATGGTGGTATGGTGGTGGTGTGTGGGTGGGTGTTGG
GTGGTGGGTGGGAATTGGAGGTGCTATCATGGTGGGTATGTTGGGGAGTTCGGAGGATGCGGTCTGTGGG
GATATGGTTCCAGGGCTAATGGGTCTGGGATGGGTCAAGGTGGAGGGGTGCGCGGTGTGCGTGTGGCGT
GGAGAGCGGCAGTTGGGTGCGGCACCGCAGCGGCGGCAACGCAGCAGCATAGGCGGCGAGGACGGCG
GCGGCGCTCCAGCGGGCAGCGAGCCACGGCGGCGGCAGCTCAGACCAGCACCGCCAGGGCCCAGCAGC
GCAGTGCAGCCAGCAACAGCGCTGGTGCTACTGCTGGTGCTACTGCTGGGAATGCGGCTGTTGTGGGCGT
CGAGCAGTAGTGACCATCACCGGCACTGCGCTGCGGCAGCCGGCCTGCCATCCAGCATGGCGCCGCGGGG
CTGGGTGCGCAAGCGAAAGGCAGCAGTGGTGGACAGAGCTGTTGAGGCACGGCGCCTGACTGCCCGGTG
GTGACGATGTGCGGATGCTCGCGCCCAGCAGAAGGGACCAGGACCCGGCTGGTGGCCGCCGCCGCCGCC
GCAGCAGCAGTCGCCACGTAGCACGCAGCGGCTACAGCAGCAACCGGCGCCCACACCCGCACCACAACCC
CAGCCACCGCACCAGCCAAACACACGCACCCTTCCCTCTCTCCCCCTCTCCTCACACGGCCCGCACTGACCT
GTCCCTCCCCGTCTCCCTCTGCTCCCCCTCCGCCACCTCAGCGCCGCCGCCAAGCCCTACATCGCCTCCATGG
GCATCTACGTCATGTCCGCCAAGGCGCTGCGCGAGCTGCTGTTGAACCGCATGCCGGGCGCCAACGACTTC
GGAAACGAGGTCATCCCCGGCGCCAAGGACGCCGGCTTCAAGGTGCAGGCCTTCGCCTTTGACGGCTACT
GGGAGGACATCGGTACCGTGGAGGCCTTCTACAACGCCAACCTGGCGCTGACCGATCCCGAGAAGGGCGCA

FIG. 9B

```
GTTCTCGTTCTACGACAAGGACGCGCCGATCTACACCATGTCGCGCTTCCTGCCGCCCTCCAAGGTGATGGA
CTGCGACGTGAACATGTCCATCATCGGCGACGGCTGCGTGATCAAGGCCGGCTCCAAGATCCACAACTCCAT
CATCGGCATCCGCTCGCTGATCGGCTCCGACTGCATCATCGACAGCGCGATGATGATGGGCTCGGACTACTA
CGAGACCCTGGAGGAGTGCGAGTACGTGCCCGGCTGCCTGCCTATGGGCGTGGGCGATGGCTCCATCATCC
GTCGCGCCATTGTGGACAAGAACGCGCGCATTGGTCCCAAGTGCCAGATCATCAACAAGGACGGCGTCAA
GGAGGCCAACCGCGAGGACCAGGGCTTCGTGATCAAGGACGGCATTGTCGTCGTGATCAAGGACTCGCAC
ATCCCCGCCGGCACCATCATCTAAACGTGATGGCTCGGGCCGGGAAGAGGCGGCGCGGCGCAGAGCCGG
CCGGCGCGGCGGCAGCCGGCGGCGCGCGGCGTGTGGCGGAGACGTTGGTGATGGAGAGCAGACGGAG
GTGGCGGGACCTCAGGCACATTTCGGCAGCTGCCGCAGCGAGGAGCAGGGAGAGCGAGCGTGTGTGGG
TGCACACGCTAGCGCGCACTCACGACCTGCAGCAGCAGCAGCCGTGGCGGAGATGGCGGGAGCTGCTCG
GGTACTGTTGAAGCGAGGCGGGCCCTTGGCTGCGTTTTTGGGTTGGAATGTTGCGCAGTGACGGGACTCT
ATAGAGTAGGGGGGATTGAGTGTCCTTGGTTCGGGTGAACGCCATGGACCGGTGCGGCACGGCGTGGCG
TGGCACTGCGTTGCTGCGGAAGCGCAAGCTGCGGCCTTCCCGCAACGGTGCAGCAGCCGCATCGGACGCA
ACACCCCAGGAGCGGCAGTAGCTGCCAGTCGCGTGCGGCTGTTTTGAGGGAGAGCGCTTTTTCGGGAGC
GTGAACGGTCGGACCAAGCACCGGCGGTGGCAGCGGCAGGCCTTCGGCCCCCCGGCCCTTAAAGCTGCC
GGCGCCAAGGCACGCCGCGAGGCGTGTGTGTTCCCGAGGTGCAGCCGGGCGGTGGCGGCTGCAGGGTG
GGTGCGAGCCAGCTGGCGTGCCATCCAGCACGGCGGCGGTTGTTGCGGCTCGGCGGTGGGGAAGGTGG
AGCACTGAGCGGGCGTGGGTCGGGACGCTTCGCGGCTCACGCGGCGGTTGGCCGTTGCGGCTGCCTTCC
GTGGGATGCCGTAGGAGGGGCGGGTCCTTACTCGCTCGCGTCCCACCTGGGGGGTTGTAGTTTCTTAATTT
AGCGTGTACCATGCTCAACATTGTTTGACTCCCCCAGACCCTGCGAACCTGCATCTGCGGAGGTAGAGAGG
GCTCTTGGGTGTGTGCAGATTTTTGGTTGTTTGGTTTGGGTGATGGTGCAACAGTTTTGCGCGTGGCGAGT
GTGTGCGTTCTCAGATGAGGAGAATTGTTTGTGCTATGCAGAGTTGAGGCGAGAGGAAGACTTTTGGGCA
CGACTGCACCGTGCATCCATGGAGCACAGCTGCATAGAAGCACGTGGGCAACGCACGGCTTGCACCGTCC
GATGCATCGTCCCCTCCCCCAGAGATTTGGACCGAGAGAAGAAATCCAGCACATGTAAACTCGTATGAGG
GCA
```

FIG. 9C

Cre03.g188250.t1.2
ADP-glucose pyrophosphorylase small subunit (GLGS). Catalytic subunit catalyzes the formation of
the glucosyl nucleotide from ATP an...

5' UTR / CDS / 3' UTR / Target sequence
(Indel sequence)
1bp Deletion and 1bp Substitution >Double ZEP/AGP mutant 2 (dZA2) - AGP gDNA sequence

```
CAGGGTTTGCTTTTGGGCACGACTTGCATTGTGTACTTGTTTGTGACCTGAGGTCGAGGACCTTCTTCTAGGT
AGTCAAAACAGAGGAAGACCGATCCTTAGCATGGCCCTGAA-TTGCGGGTGAGCCAGCGCCAGGCGCTG
GGCTCGCAGACCTTCGTCTGCCCCACGGTGCGTGGCATGAACAGCGTTTTATGTCGACTTGGGCCGGAGCG
CAGCGGACTCAACCGACTCATCTCGCAGGCTCAGTGGTGCGCAAGGCCGTGAGCTCCAAGGCCCGCGCCGT
GTCGCGCCAGGCTCAGGTAAATGGATCATGCATTCGCACATGCATTTGGGCGACGTCACTGCGACTTACCGG
GTCGCCTTATCGCAGGTCGTTCGGGCTCAGGCTGTGTCGACCCCGTTGAGACCAAGGTCGCGAACGGGGT
GGCCGCATCCTCTGCTGCGGGCACTGGGCAGAACGACCGGCTGGCGACATCAGCAAGGTATGCTCGCGCT
GGCCCATTTGATGCTTCCGGACTCGTCGATGTGACCGTCCCGCCATCTCGTTGCCGATGCAGACGGTGCTGGG
TATTATTCTGGGTGGTGGTGCCGGCACCCGTCTGTATCCTCTGACCAAGAAGCGTGCCAAGCCGGCGGTGCC
CCTGGGCGCCAACTATCGCCTGATCGATATTCCCGTTAGCAACTGCCTGAACAGCAATGTCACCAAGATTTACT
GCCTCACCCAGTTCAACTCGGCGTCGCTGAACCGCCACCTGTCCCAGGCCTACGTGAGTACCTTGTGAATACT
GAAACTGCGGGCTCGGGCTCGGGCGACATAGCTGTCGGCCGACCGCAGAATGCGTCGCCATGCGGACTCGG
CGCAACACCTGTCGCGTGTCACTCCCGCTAGGGCACAGGAGCGAACCAGCCCTCCAGGCGGCTTAATCCATC
AGGGAGACTGTATGTTCAGATGGAAGGGACACAAGGGCGGGGCTGCGAAAGCTTTCAAGTACACACGTGT
GGCATCATATGCTCTACCAGCGCACAGCGCCACCGCACACCGTACCGCGTCCACATCCACCTCTTGCCATCCCA
CCCCTCTCCCATCCTCCCACCCTCCCATCCTCCCACCCTCCCATCAACCCCATCAACCCCACCCCACCACCCTCCC
CTCTCTCCGCTCCCCCTCTCGCACAGAACTCGTCTGTGGGCGGCTACAACAGCCGCGGCTTCGTGGAGGTGC
TGGCGGCCAGCCAGTCGTCCGCCAACAAGAGCTGGTTCCAGGGCACCGCTCGACGCCGTGCGCCAGTACATG
TGGCTGTTCGAGGAGGCGGTGCGCGAGGGCGTGGAGGACTTCCTCATCCTGTCGGGTGAGTGGGCAGGAA
GAGGGGTGGAGAGGGGGAAAGTTGGGGGTGGGTGCACGGAATGGGTGGGAAGGGGGGGTTTCCTCCTG
CGCAAGGCAGCGAGGCGAGAAGGTTGAGGCCGCCGTAACTGGGGGTGGTGGAGTGGGCGGGTGAGGCG
CATGTTGAATGGGGCATGGAAGACTGGTGGGTGGGTGAGTGGAGAGGCGAAGTTTCGGAGGGTGCCGGA
AAGGGCATGGCGGTGCAGGGTGCCACTGGGCACGGTGGCCTGCCGTCAAGCGGGCGTGTTGGGCAGCGG
GACTGCGCGCTGCAGCAGCCGGCACAGATACGGAGCGCACGGCAGGACGACACGCGGGCAGCCGGCGG
GCTGGTCGGTCGGTGTGCTGGGGGCAGCAGCGACGCGCTGGTACACGGAGGGCTACGAGTGCTGCACAGC
CAGCCTCGGCACACAACAGCCACCAGTACGGCATGTAGCACCACGCGTCTGGCTTACCAGTATCAGCGCAGT
AGCGGACCAATGGGGGCGGCACGGAACGCGTGTGTGCGGATGGGCTGCGGCACCGCCAACCGGACGACTC
CCAAACATCACATCCTCCCCCCTCCTCCAGGCGACCACCTGTACCGCATGGACTACCGCGACTTTGTCCGCAA
GCACCGCAACTCGGGCGCCGCCATCACCATCGCCGCGCTGCCCTGCGCGGAGAAGGAGGCCAGCGCCTTCG
GCCTGATGAAGATCGACGAGGAGGGCCGCGTGATCGAGTTCGCGGAGAAGCCCAAGGGGCGAGGCGCTGA
CCAAGATGCGCGTGGACACCGGCATCCTGGGCGTCGACCCCGCCACGTGAGTGTGTGCGCGCTGGTGTTGG
TTGACATGGTGGTATGGTGGTGGTGTGTGGGTGGGTGTTGGGTGGTGGGTGGGAATTGGAGGTGCTATCAT
GGTGGGTATGTTGGGGAGTTCGGAGGATGCGGTCTGTGGGATATGGTTCCAGGGCTAATGGGTCTGGGAT
GGGTCAAGGTGGAGGGGTGCGCGGTGTGCGTGTGGCGTGGAGAGCGGCAGTTGGGTGCGGCACCGCAGC
GGCGGCAACGCAGCAGCATAGGCGGCGAGGACGGCGGCGGCGCTCCAGCGGGCAGCGAGCCACGGCGG
CGGCAGCTCAGACCAGCACCGCCAGGGCCCAGCAGCGCAGTGCAGCCAGCAACAGCGCTGGTGCTACTGC
TGGTGCTACTGCTGGGAATGCGGCTGTTGTGGGCGTCGAGCAGTAGTGACCATCACCGGCACTGCGCTGCG
GCAGCCGGCCTGCCATCCAGCATGGCGCCGCGGGCTGGGTGCGCAAGCGAAAGGCAGCAGTGGTGGAC
AGAGCTGTTGAGGCACGGCGCCTGACTGCCCGGTGGTGACGATGTGCGGATGCTCGCGCCCAGCAGAAGG
GACCAGGACCCGGCTGGTGGCCGCCGCCGCCGCCGCAGCAGCAGTCGCCACGTAGCACGCAGCGGCTACA
GCAGCAACCGGCGCCCACACCCGCACCACAACCCCAGCCACCGCACCAGCCAAACACACGCACCCTTCCCTC
TCTCCCCCTCTCCTCACACGGCCCGCACTGACCTGTCCCTCCCCGTCTCCCTCTGCTCCCCTCCGCCACCTCAG
CGCCGCCGCCAAGCCCTACATCGCCTCCATGGGCATCTACGTCATGTCCGCCAAGGCGCTGCGCGAGCTGCT
GTTGAACCGCATGCCGGGCGCCAACGACTTCGGAAACGAGGTCATCCCCGGCGCCAAGGACGCCGGCTTCA
```

FIG. 9D

```
AGGTGCAGGCCTTCGCCTTTGACGGCTACTGGGAGGACATCGGTACCGTGGAGGCCTTCTACAACGCCAAC
CTGGCGCTGACCGATCCCGAGAAGGCGCAGTTCTCGTTCTACGACAAGGACGCGCCGATCTACACCATGTCG
CGCTTCCTGCCGCCCTCCAAGGTGATGGACTGCGACGTGAACATGTCCATCATCGGCGACGGCTGCGTGATC
AAGGCCGGCTCCAAGATCCACAACTCCATCATCGGCATCCGCTCGCTGATCGGCTCCGACTGCATCATCGACA
GCGCGATGATGATGGGCTCGGACTACTACGAGACCCTGGAGGAGTGCGAGTACGTGCCCGGCTGCCTGCCT
ATGGGCGTGGGCGATGGCTCCATCATCCGTCGCGCCATTGTGGACAAGAACGCGCGCATTGGTCCCAAGTGC
CAGATCATCAACAAGGACGGCGTCAAGGAGGCCAACCGCGAGGACCAGGGCTTCGTGATCAAGGACGGCA
TTGTCGTCGTGATCAAGGACTCGCACATCCCCGCCGGCACCATCATCTAAACGTGATGGCTCGGGCCGGGAA
GAGGCGGCGCGGCGCAGAGCCGGCCGGCGCGGCGGCAGCCGGCGGCGCGCGGCGTGTGGCGGAGACGT
TGGTGATGGAGAGCAGACGGAGGTGGCGGGACCTCAGGCACATTTCGGCAGCTGCCGCAGCGAGGAGCA
GGGAGAGCGAGCGTGTGTGGGTGCACACGCTAGCGCGCACTCACGACCTGCAGCAGCAGCAGCCGTGGCG
GAGATGGCGGGAGCTGCTCGGGTACTGTTGAAGCGAGGCGGGCCCTTGGCTGCGTTTTTGGGTTGGAATG
TTGCGCAGTGACGGGACTCTATAGAGTAGGGGGGATTGAGTGTCCTTGGTTCGGGTGAACGCCATGGACCG
GTGCGGCACGGCGTGGCGTGGCACTGCGTTGCTGCGGAAGCGCAAGCTGCGGCCTTCCCGCAACGGTGCA
GCAGCCGCATCGGACGCAACACCCCAGGAGCGGCAGTAGCTGCCAGTCGCGTGCGGCTGTTTTGAGGGAG
AGCGCTTTTTCGGGAGCGTGAACGGTCGGACCAAGCACCGGCGGTGGCAGCGGCAGGCCTTCGGCCCCCC
GGCCCTTAAAGCTGCCGGCGCCAAGGCACGCCGCGAGGCGTGTGTGTTCCCGAGGTGCAGCCGGGCGGTG
GCGGCTGCAGGGTGGGTGCGAGCCAGCTGGCGTGCCATCCAGCACGGCGGCGGTTGTTGCGGCTCGGCGG
TGGGGAAGGTGGAGCACTGAGCGGGCGTGGGTCGGGACGCTTCGCGGCTCACGCGGCGGTTGGCCGTTG
CGGCTGCCTTCCGTGGGATGCCGTAGGAGGGCGGGTCCTTACTCGCTCGCGTCCCACCTGGGGGTTGTA
GTTTCTTAATTTAGCGTGTACCATGCTCAACATTGTTTGACTCCCCCAGACCCTGCGAACCTGCATCTGCGGAG
GTAGAGAGGGCTCTTGGGTGTGTGCAGATTTTTGGTTGTTTGGTTTGGGTGATGGTGCAACAGTTTTGCGCG
TGGCGAGTGTGTGCGTTCTCAGATGAGGAGAATTGTTTGTGCTATGCAGAGTTGAGGCGAGAGGAAGACTT
TTGGGCACGACTGCACCGTGCATCCATGGAGCACAGCTGCATAGAAGCACGTGGGCAACGCACGGCTTGCA
CCGTCCGATGCATCGTCCCCTCCCCCAGAGATTTGGACCGAGAGAAGAAATCCAGCACATGTAAACTCGTATG
AGGGCA
```

[FIG. 10]
a. Media   b. Starch staining
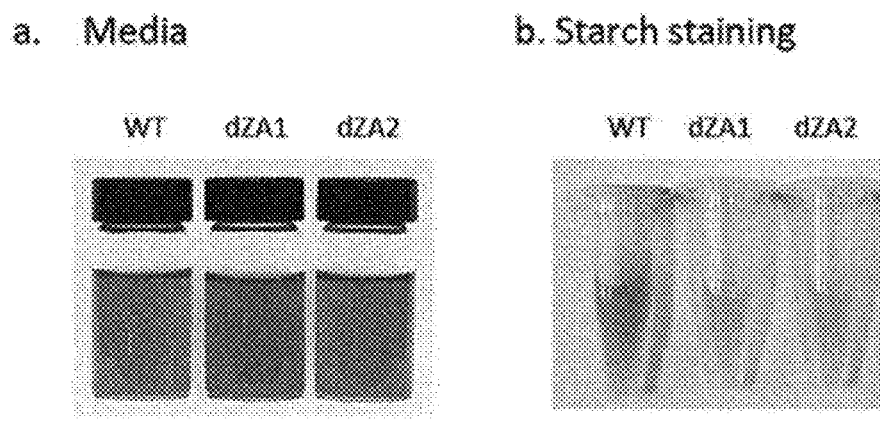
[FIG. 11]
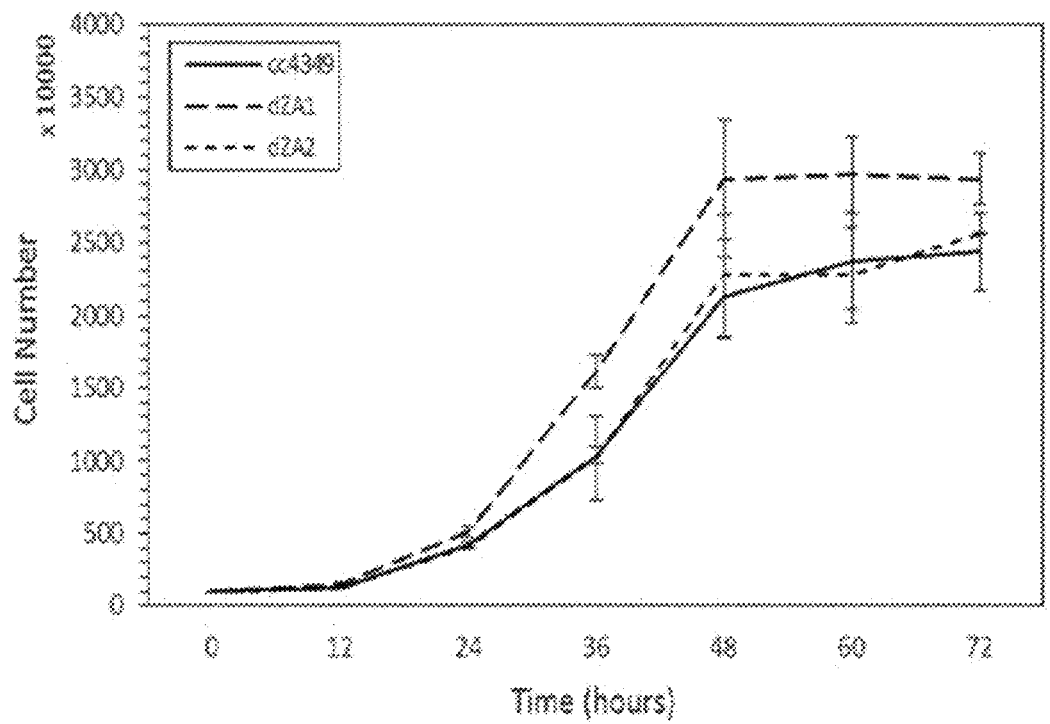

[FIG. 12a]
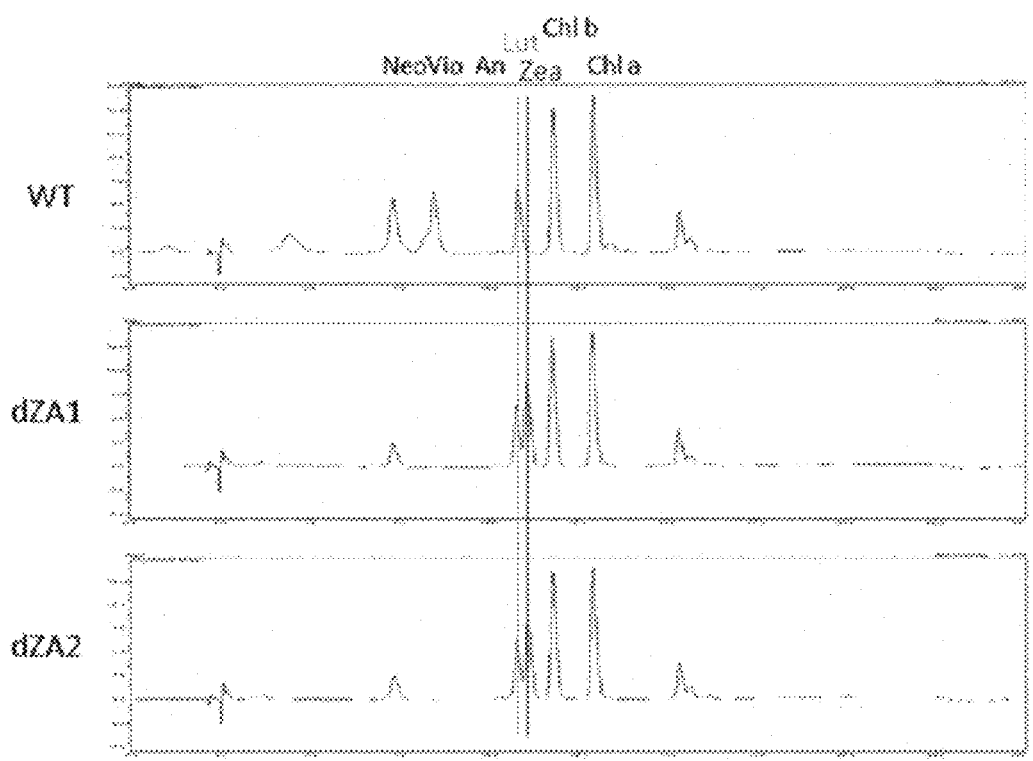
[FIG. 12b]
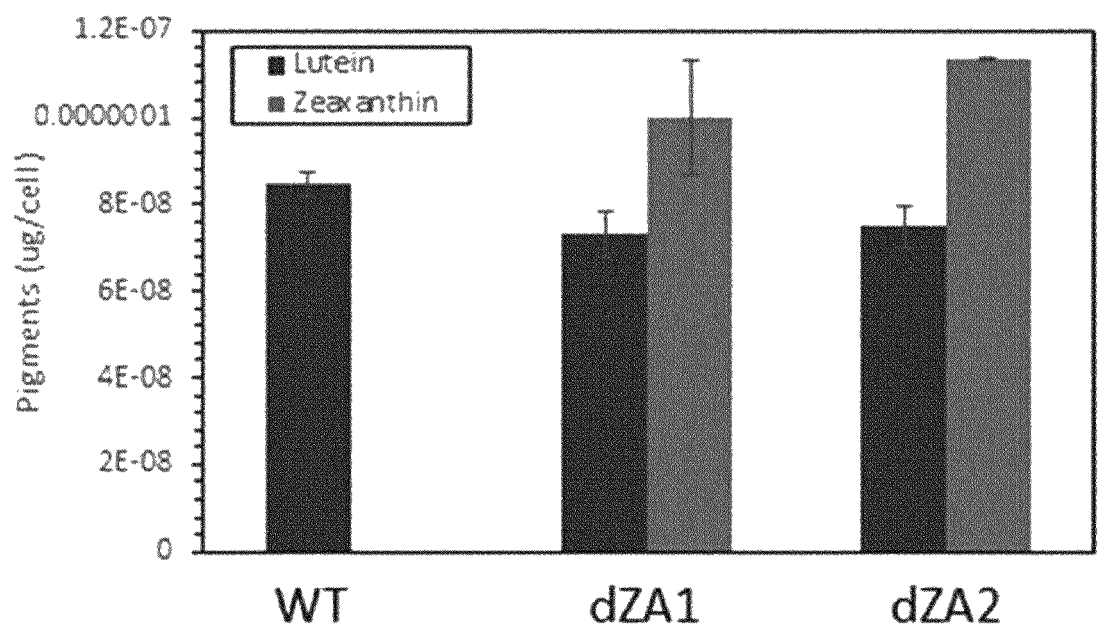

[FIG. 12c]
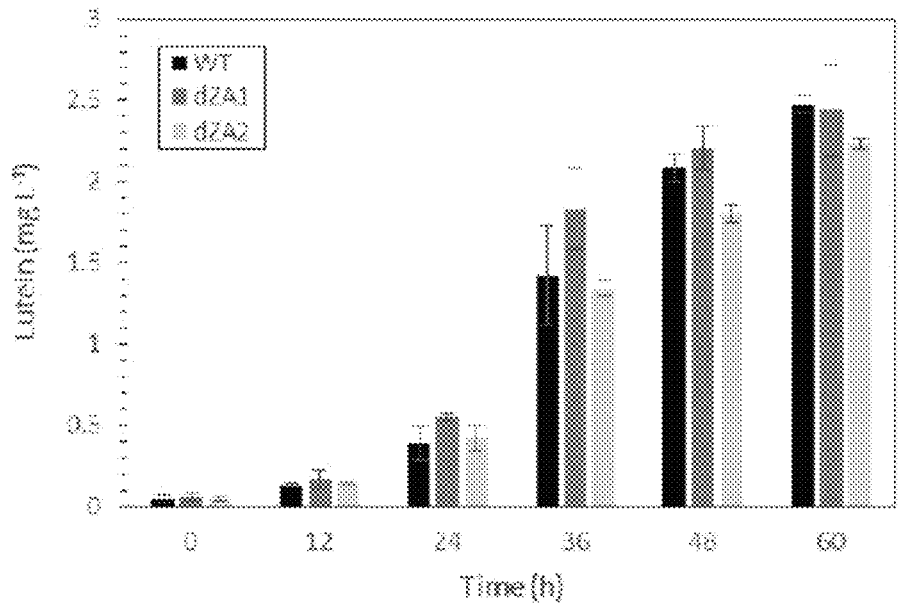
[FIG. 12d]
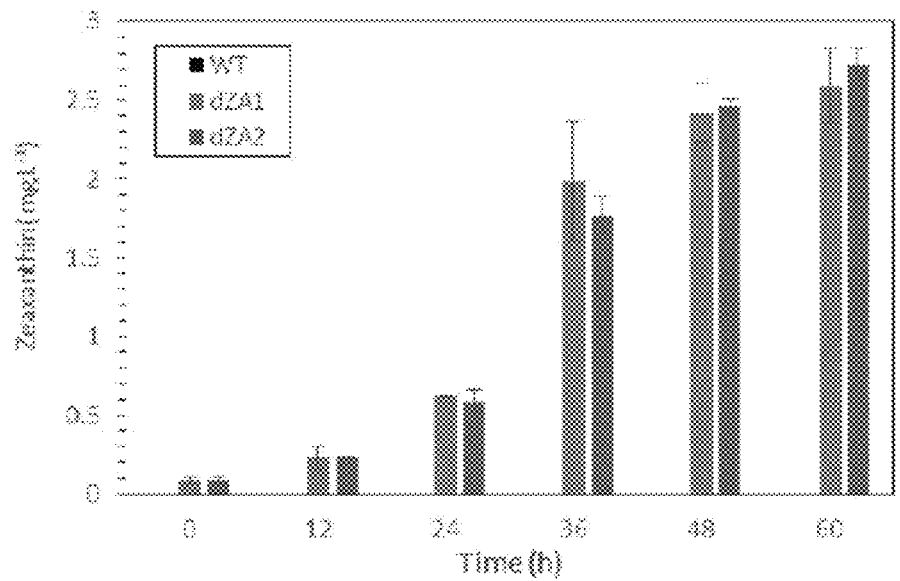

[FIG. 13a]
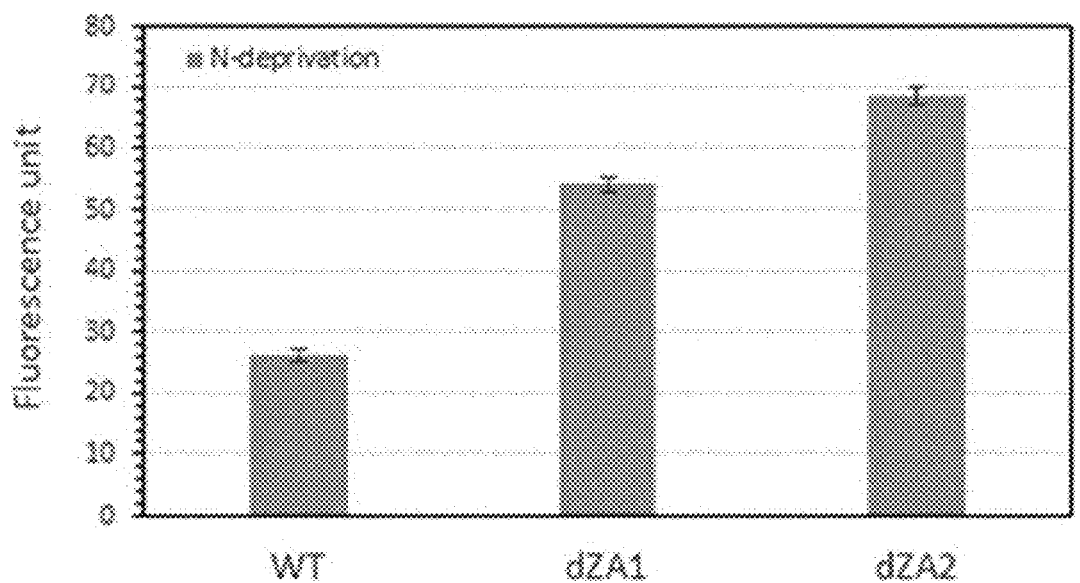
[FIG. 13b]
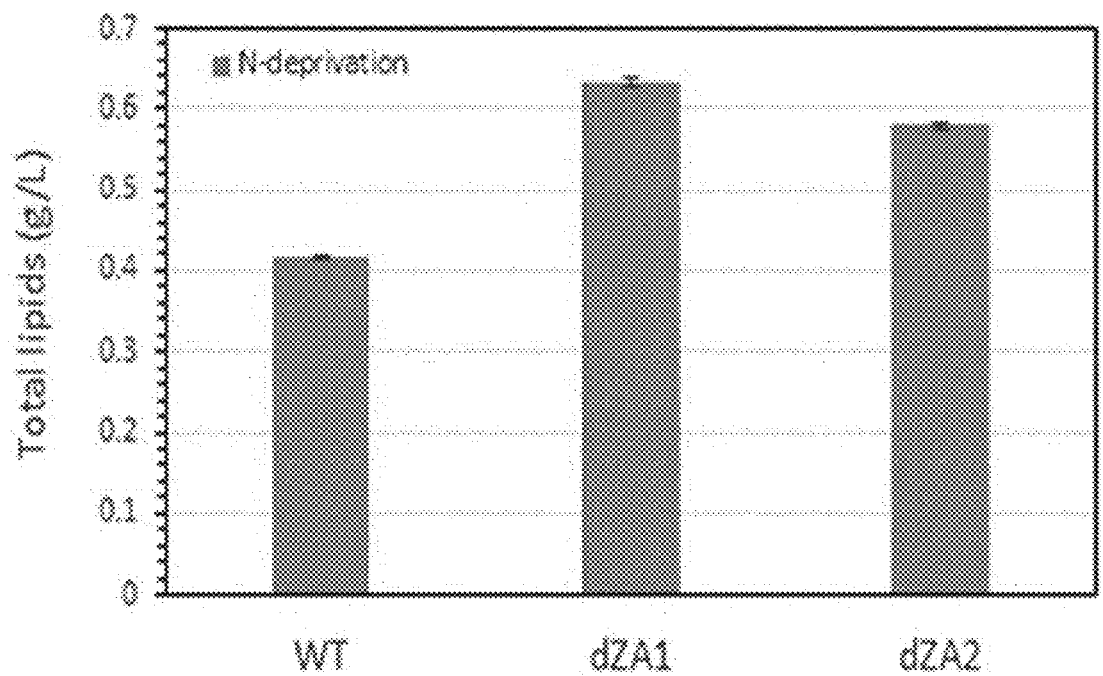

CHLAMYDOMONAS MUTANT AND USE THEREOF

CROSS REFERENCE TO RELATED APPLICATIONS

This application is a national stage of International Application no. PCT/KR2020/000394 filed Jan. 9, 2020, claiming priority based on Korean Patent Application No. 10-2019-0002969 filed Jan. 9, 2019.

SEQUENCE LISTING

The content of the electronically submitted sequence listing, file name: Substitute_Sequence_Listing_As-_Filed.txt; size: 72,254 bytes; and date of creation: Feb. 28, 2022, filed herewith, is incorporated herein by reference in its entirety.

TECHNICAL FIELD

The present invention relates to microalgae having vegetable oil production ability with improved antioxidant pigment content and use thereof, more particularly, to a composition including the microalgae described above and a method for production of vegetable oil using the microalgae.

BACKGROUND ART

As essential fatty acids, linoleic acid (omega-6) and α-linoleic acid (omega-3) must be consumed through food. These essential fatty acids are responsible for growth in the human body and have an important role in regeneration and reproduction of the skin, in maintaining red blood cell structure, and in formation and maintenance of cell membrane structures in the retina of the eye and the central nervous system. These essential fatty acids may be consumed through animal and vegetable oils.

Animal oil includes animal fat as a raw material, has a high saturated fat content, and is contained in a lot of meat fat, butter, cheese, mayonnaise, cream, cocoa, processed oil, ramen, etc. Saturated fat forms a part of the human subcutaneous fat layer, and an appropriate amount of subcutaneous fat is essential. However, since the fat is usually combined with cholesterol, a level of low-density cholesterol bad for the body is increased while increases the risk of cardiovascular disease or stroke. Among animal oils, fish oil has a high content of unsaturated fatty acids and is rich in omega-3 including DHA and EPA, but has problems in storage and acidification. Further, large fish species such as tuna and salmon, which are used as main raw materials for omega-3, may contain toxins such as high concentrations of mercury, dioxin, polyvinyl chloride, etc. due to environmental contamination, hence causing a problem in stability of fish oil. Further, there is a problem in supply due to depletion of fish stocks. Therefore, it is necessary to discover stable and new supply methods of unsaturated fatty acids.

Other sources of unsaturated fatty acids include vegetable oils such as soybean oil, canola oil, corn oil, safflower oil, and the like. However, vegetable oils have a high content of polyunsaturated fatty acid, whereby vegetable oils are easily oxidized during manufacture or storage. As a result, free radicals are generated. When oxidized fat enters the body, it causes inflammation and cell changes, and oxidizes and scatters cholesterol in the arteries, causing vascular disease.

In order to solve this problem, a method of artificially forming hardened oil in a solid state by adding hydrogen to vegetable oil in a liquid state was sought. However, typical hardened oil such as margarine encounters a problem in that transfats known to be harmful to the body are produced during processing. In addition, commonly consumed edible oils (such as soybean oil, corn oil and sunflower seed oil) contain a large amount of omega-6 fatty acids, which may collapse a ratio of omega1-3 and omega-6 levels in the body due to excessive intake through diet, thereby causing health problems such as persistent inflammation. Further, vegetable oil obtained from higher plants is not free from GMO as well as pesticide contamination problems of raw materials due to commercial mass production of crops.

In another attempt, microalgae have attracted attention as an alternative source of vegetable oil. Vegetable oil extracted from microalgae has an excellent fatty acid profile that is not found in other oils. Specifically, the amount of monounsaturated fat was 13 g higher than that of olive oil which is 9.9 g per tablespoon, and a saturated fat content of microalgae was about 4% which is significantly lower compared with olive oil (14%), canola oil (7%) and coconut oil (87%). Therefore, like fish oil, the oil extracted from microalgae contains abundant EPA and DHA consisting of omega-3 fatty acids, so that this oil has high potential to be used as a desirable substitute for fish oil and a source of omega-3 fatty acids.

However, microalgae oil may also have a problem that the oil is easily acidified due to high content of unsaturated fatty acids, and studies and attempts have been made to overcome such shortcomings. For example, since olive oil contains antioxidants such as vitamin E, it has been reported that the shelf-life of olive oil is longer than other vegetable oils. In the case of microalgae, if the problem of acidification can be solved, the microalgae may be used in the form of oil in a variety of food, cosmetic and pharmaceutical applications. Therefore, there is a need for approaches in new aspects to improve characteristics such as shelf life of vegetable oil obtained from microalgae.

DISCLOSURE

Technical Problem

An object of the present invention is to provide a novel strain with improved lipid production ability, a composition using the same, and a method for production of a vegetable oil using the same, whereby functionally superior vegetable oil, especially, a vegetable oil with high unsaturated fatty acid content can be stably and efficiently supplied on an industrial scale.

Technical Solution

In order to achieve the above objects, the present inventors have developed a novel *Chlamydomonas* strain that produces vegetable oil with improved antioxidant pigment content using genetic scissors without introducing external DNA, and have discovered a method for production of vegetable oil using the above strain, thereby completing the present invention. In particular, a mutant strain of the present invention has a xanthophyll-based pigment, that is, zeaxanthin production ability, which in turn exhibits distinguishable properties from wild-type strains. Further, the mutant strain of the present invention has superior lipid production ability and faster cell growth rate, as compared to the wild-type strains. Therefore, the strain of the present invention supplying vegetable oil is very advantageous in the industrial field.

In this respect, the present invention may provide a *Chlamydomonas reinhardtii* mutant strain, including: a ZEP gene mutant in which adenine A, a base sequence represented by SEQ ID NO: 3 or a base sequence represented by SEQ ID NO: 5 is inserted between the 816th base and the 817th base in the ZEP gene sequence of *Chlamydomonas reinhardtii* represented by SEQ ID NO: 1; and an AGP gene mutant in which adenine A is inserted between the $116^{th}$ base and the $117^{th}$ base in the AGP gene sequence of *Chlamydomonas reinhardtii* represented by SEQ ID NO: 2, otherwise, the 115th base is deleted while the 116th base is substituted by thymine T.

The above mutant strain may be characterized by having improved lipid production ability and zeaxanthin and lutein production ability, as compared to wild-type strains.

Further, the present invention may provide a culture of the mutant strain.

Further, the present invention may provide a cosmetic composition including at least one selected from the group consisting of the mutant strain and cultures thereof.

Further, the present invention may provide a composition for food or food additives including at least one selected from the group consisting of the mutant strain and cultures thereof.

Further, the present invention may provide a composition for feed or feed additives including at least one selected from the group consisting of the mutant strain and cultures thereof.

Further, the present invention may provide a method for production of vegetable oil, which includes culturing the mutant strain.

Further, in an aspect that the vegetable oil contains a large amount of unsaturated fatty acids, the present invention may provide a method for producing unsaturated fatty acids, which includes culturing the mutant strain.

Further, the present invention may provide a method for production of raw materials for food or feed, which includes culturing the mutant strain.

Further, the present invention may provide use of the above mutant strain for producing food, feed, food raw materials or feed raw materials.

Further, the present invention may provide a method for preparation of a *Chlamydomonas reinhardtii* mutant strain with improved oil production ability, which includes a ZEP gene mutant and an AGP gene mutant, comprising: mutation of ZEP genes while targeting the 800th to 820th bases in the ZEP gene sequence of *Chlamydomonas reinhardtii* represented by SEQ ID NO: 1; and mutation of AGP genes while targeting the 100th to 120th bases in the AGP gene sequence of *Chlamydomonas reinhardtii* represented by SEQ ID NO: 2.

The gene mutation may be performed by transformation of *Chlamydomonas reinhardtii* cells with preassemble complex that include polynucleotides expressing a single guide RNA (sgRNA) containing a sequence of target gene, as well as Cas protein.

The gene mutant may include the ZEP gene mutant and the AGP gene mutant, in particular: a ZEP gene mutant in which adenine A, a base sequence represented by SEQ ID NO: 3 or a base sequence represented by SEQ ID NO: 5 is inserted between the 816th base and the 817th base in the ZEP gene sequence of *Chlamydomonas reinhardtii* represented by SEQ ID NO: 1; and an AGP gene mutant in which adenine A is inserted between the 116th base and the 117 th base in the AGP gene sequence of *Chlamydomonas reinhardtii* represented by SEQ ID NO: 2, otherwise, the 115th base is deleted while the 116th base is substituted by thymine T.

Advantageous Effects

According to the present invention, a mutation location, at which ZEP gene and AGP gene may be simultaneously knocked out without introduction of external DNA in microalgae *Chlamydomonas Reinhardtii*, could be identified, thereby developing a new mutant strain including simultaneous knockout. As a result of confirming cell characteristics of the mutant strain having mutation of the above site, an amount of zeaxanthin as an industrially useful pigment was markedly increased and, at the same time, a lipid production ability was improved. Further, a cell growth rate was faster compared to wild-type *Chlamydomonas reinhardtii* strains, therefore, it is advantageous to provide an industrially useful material using microalgae. In particular, the novel microalgae of the present invention are free from the risk of GMO because no external genes are introduced. Further, since vegetable oil extracted from the microalgae of the present invention has higher content of xanthophyll-based pigments such as lutein and zeaxanthin having antioxidant activity, oil preservation and stability are excellent, whereby the vegetable oil can be effectively used in food, medicine and cosmetics.

DESCRIPTION OF DRAWINGS

FIG. 1 illustrates overall technique in regard to a method for preparation of ZEP and AGP gene-edited *Chlamydomonas* mutant stains according to an embodiment of the present invention.

FIGS. 2A, 2B, 2C, 2D, 2E and 2F illustrate ZEP gene information of *Chlamydomonas reinhardtii* mutantΔZ1 (FIGS. 2A and 2B) [SEQ ID NO: 4]; ZEP gene information of *Chlamydomonas reinhardtii* mutant ΔZ2 (FIGS. 2C and 2D) [SEQ ID NO: 6]; and ZEP gene information of *Chlamydomonas reinhardtii* mutant ΔZ3 (FIGS. 2E and 2F) [SEQ ID NO: 7].

FIGS. 3A and 3B illustrate ZEP gene mutants induced by DNA-free RGEN-RNP [3a: frequencies of RGEN-transfected cells and wild type mutants (insertion and deletion; Indel) for each sgRNA were measured by targeted deep sequencing. Indel frequency was measured to about 0.46%. 3b: according to targeted deep sequencing of representative mutant DNA sequence (RGEN3) obtained from the most efficient third sgRNA, which was observed in the targeted deep sequencing analysis of FIG. 3A, different Indel patterns were identified in the target sequence and results thereof are shown. This appeared at 3 nt upstream of PAM sequence]. In FIG. 3B, the sequence of Control is SEQ ID NO: 18, the sequence of 2 ins (ZEP-RGENE3 2 insert) is SEQ ID NO: 19, the sequence of 1 del (ZEP-RGENE3 1 delete) is SEQ ID NO: 20, the sequence of 4 del (ZEP-RGENE3 4 delete) is SEQ ID NO: 21, the sequence of 6 ins (ZEP-RGENE3 6 insert) is SEQ ID NO: 22, and the sequence of 1 ins (ZEP-RGENE3 1 insert) is SEQ ID NO: 23.

FIG. 4 illustrates a result of confirming a change in target DN sequence at the actual ZEP gene position in three ZEP mutants generated by DNA-free RGENRNPs through Sanger sequencing [a: wild type, b: ZEP mutant 1(ΔZ1), c: ZEP mutant 2 (ΔZ2), d: ZEP mutant 3 (ΔZ3), 42 Ins (SEQ ID NO: 3), 44 Ins(SEQ ID NO: 5)].

FIG. 5 illustrates a Cas9 protein sequence (SEQ ID NO: 16) used in one embodiment of the present invention.

FIGS. 6A, 6B and 6C are photographs showing morphological features of *Chlamydomonas reinhardtii* cw15 wild-type microalgae, *Chlamydomonas reinhardtii* ΔZ1, ΔZ2 and ΔZ3 [6a: results of measurement of chlorophyll (Chl) fluorescence for hundreds of colonies in order to study ZEP gene knockout, 6b: a photograph showing culturing colonies on solid TAP medium containing agar, 6c: a photograph showing a state when adjusted to the same concentration ($OD_{750}$=1) after liquid-culturing in HS medium].

FIGS. 7A and 7B illustrate sequence information of AGP (ADP glucose pyrophosphorylase) gene (SEQ ID NO: 9) of wild-type *Chlamydomonas reinhardtii* cw15.

FIG. 8A is a table showing positions and features of four (4) sgRNAs to target AGP (ADP glucose pyrophosphorylase) of *Chlamydomonas reinhardtii*; and FIG. 8B illustrates a result of confirming a change in target DNA sequence of the actual AGP gene position in each of two AGP mutants generated by DNA-free RGENRNP. In FIG. 8A, sgRNA sequences of AGP4_sg1, AGP4_sg2, AGP4_sg3, and AGP4_sg4 are shown in SEQ ID NO: 24, SEQ ID NO: 25, SEQ ID NO: 26, and SEQ ID NO: 27, respectively. In FIG. 8B, the WT sequence TGAAGA(-)TGCGG is base sequence at positions 111-122 of SEQ ID NO: 2, the sequence of dZA1 1 Ins is base sequence at positions 111-123 of SEQ ID NO: 8, and the sequence of dZA2 1Del, 1Sub is base sequence at positions 111-121 of SEQ ID NO: 9.

FIGS. 9A, 9B, 9C and 9D illustrate sequence information on each AGP gene of *Chlamydomonas reinhardtii* mutants dZA1 [SEQ ID NO: 8](FIGS. 9A and 9B) and dZA2 [SEQ ID NO: 9](FIGS. 9C and 9D), wherein red-colored sequences refer to sequences inserted, deleted or substituted in the mutant strain.

FIG. 10 illustrates a result of confirming morphological features of the wild-type *Chlamydomonas reinhardtii* cw15, mutants dZA1 and dZA2, wherein: a is a comparison of color phenotypes when cultured in liquid medium (TAP) and adjusted to the same concentration; and b is discoloration by starch when reacted with Lugol's solution at the same concentration after 3 days of nitrogen depletion.

FIG. 11 illustrates results of confirming growth characteristics of the wild-type *Chlamydomonas reinhardtii* cw15, mutants dZA1 and dZA2 according to one embodiment of the present invention: graphs showing growth curves (number of cells per volume, cells/ml) over time.

FIGS. 12A, 12B, 12C and 12D illustrate results of pigment analysis for the wild-type *Chlamydomonas reinhardtii* cw15, *Chlamydomonas reinhardtii* mutants dZA1 and dZA2, respectively, according to one embodiment of the invention, in particular: FIG. 12A is HPLC analysis graphs showing the profile of pigments of each strain (neo: neoxanthin, vio: violaxanthin, an: antheraxanthin, lut: lutein, zea: zeaxanthin, chl a: Chlorophyll a, chl b: Chlorophyll b); FIG. 12B is a graph confirming the contents of pigments (lutein and zeaxanthin) of each strain; FIG. 12C is an analysis graph confirming lutein content over time (weight per volume, mg/L); and FIG. 12D is a graph confirming zeaxanthin content over time (weight per volume, mg/L).

FIGS. 13A and 13B illustrate comparison of lipid-producing properties of the wild-type *Chlamydomonas reinhardtii* cw15, and mutants dZA1 and dZA2 according to one embodiment of the invention, in particular: FIG. 13A shows a result of TAG lipid content analysis using Nile red solution; and FIG. 13B shows a result of total lipid content analysis by organic solvent extraction (g/L).

DETAILED DESCRIPTION OF PREFERRED EMBODIMENTS OF INVENTION

The present invention can be variously modified and may have different forms, and specific embodiments and explanation described below are only for understanding the present invention and are not intended to limit the same to specific disclosed forms. It should be understood that the scope of the present invention includes all modifications, equivalents or substitutions included in the spirit and scope of the present invention.

Herein after, the present invention will be described in detail by means of examples.

The present invention relates to a *Chlamydomonas reinhardtii* mutant strain.

*Chlamydomonas reinhardtii* of the present invention is unicellular green algae (Chlorophyta) as eukaryotes that are distributed in various environments such as fresh water and the ocean, and has a cell division time ("doubling time") of 6-8 hours. Further, this is one of the most widely used microalgae model systems and can be produced in a bioreactor.

The mutant strain of the present invention may be produced by double-knocking out the ZEP (Zeaxanthin epoxidase) gene and the AGP (ADP glucose pyrophosphorylase) gene using RGENERNPs and CRISPR gene scissors technology rather than general mutagenesis. In this aspect, the mutant strain of the present invention may include mutants at specific positions of the Zeaxanthin epoxidase (ZEP) gene and the ADP glucose pyrophosphorylase (AGP) gene. Using the CRISPR gene scissors technology may possibly knock-out the gene at a desired gene position, whereby the mutant strain of the present invention may be identified through mutation sites of the ZEP (Zeaxanthin epoxidase) gene and the AGP (ADP glucose pyrophosphorylase) gene. Further, mutant strains may be produced from wild-type *Chlamydomonas reinhardtii* microalgae.

In the present invention, "variation (or mutation)" indicates that a base sequence is changed by insertion, deletion, or substitution of bases in the original sequence. Specifically, "insertion mutation" occurs when some bases are inserted between the original base sequences. The number of bases to be inserted may differ depending on the mutation, and thus is not limited. The term "deletion mutation" refers to a mutation in which the base is absent from the original sequence, and "substitution mutation" means that the original base is replaced with another one without changing the length of the original base sequence.

A mutant strain of the invention may include insertion mutation wherein some bases are inserted between the 816th base and the 817th base in the ZEP gene sequence of *Chlamydomonas reinhardtii* represented by SEQ ID NO: 1, and the ZEP gene can be knocked out by the same.

According to one embodiment, the present invention may include a ZEP gene mutant in which adenine A, a base sequence represented by SEQ ID NO: 3 or a base sequence represented by SEQ ID NO: 5 is inserted between the 816th base and the 817th base in the ZEP gene sequence of *Chlamydomonas reinhardtii* cw15 (SEQ ID NO: 1), wherein the ZEP gene was confirmed to be effectively knocked out in each mutant strain. Therefore, the mutant strain of the present invention may include a ZEP gene mutant in which adenine A, a base sequence represented by SEQ ID NO: 3 or a base sequence represented by SEQ ID NO: 5 is inserted between the 816th base and the 817th base in the ZEP gene sequence (SEQ ID NO: 1).

Further, the mutant strain of the present invention may include mutation in which some bases are inserted, deleted and/or substituted between the 116th base and the 117th base in the AGP gene sequence of *Chlamydomonas reinhardtii* represented by SEQ ID NO: 2, whereby the AGP gene can be knocked out by the above mutation.

According to one embodiment, the present invention may prepare a mutant strain including an AGP gene mutant in which adenine A is inserted between the 116th base and the 117th base in the AGP gene sequence of *Chlamydomonas reinhardtii* cw15 (SEQ ID NO: 2), otherwise, the 115th base is deleted while the 116th base is substituted by thymine T, wherein the AGP gene is confirmed to be effectively knocked out in each mutant strain.

In one embodiment of the present invention, four (4) target sites are selected from the AGP gene sequence of SEQ ID NO: 2 to design sgRNA, which in turn is used to correct the gene through Cas9. As a result, when other target sites were used, knockout of the AGP gene did not occur. On the other hand, when targeting 20 to 30 consecutive bases from the 100th base in the sequence of SEQ ID NO: 2, the AGP gene was effectively knocked out only if mutation preferably occurs between the 115th and 117th bases. Therefore, the present invention has a highly significant technical feature in that an AGP gene knockout mutant can be obtained when mutation occurs between the 115th base and the 117th base in the AGP gene sequence of SEQ ID NO:2.

According to one embodiment of the present invention, the mutant strain may include a gene mutant in which adenine A is inserted between the 116th base and the 117th base in the AGP gene sequence (SEQ ID NO: 2); otherwise, the 115th base is deleted while the 116th base is substituted with thymine (T). As a specific example, the mutant strain of the present invention may include the mutated AGP gene of SEQ ID NO: 8 or SEQ ID NO: 9.

Preferably, the mutant strain of the present invention may include ZEP and AGP gene mutants simultaneously. More particularly, the mutant strain of the present invention may be a *Chlamydomonas reinhardtii* mutant strain including: a ZEP gene mutant in which adenine A, a base sequence represented by SEQ ID NO: 3 or a base sequence represented by SEQ ID NO: 5 is inserted between the 816th base and the 817th base in the ZEP gene sequence of *Chlamydomonas reinhardtii* represented by SEQ ID NO: 1; and an AGP gene mutant in which adenine A is inserted between the 116th base and the 117th base in the AGP gene sequence of *Chlamydomonas reinhardtii* represented by SEQ ID NO: 2, otherwise, the 115th base is deleted while the 116th base is substituted by thymine T.

For a more specific example, the mutant strain of the present invention may include a mutated ZEP gene represented by SEQ ID NO: 4, SEQ ID NO: 6 or SEQ ID NO: 7; and a mutated AGP gene represented by SEQ ID NO: 8 or SEQ ID NO: 9.

In a specific embodiment of the present invention, a double ZEP/AGP gene knockout mutant including the ZEP gene mutant of SEQ ID NO: 7 and the AGP gene mutant represented by SEQ ID NO: 8 is designated as dZA1 (double ZEP/AGP mutant 1), while a double ZEP/AGP gene knockout mutant including the ZEP gene mutant of SEQ ID NO: 7 and the AGP gene mutant represented by SEQ ID NO: 9 is designated as dZA2 (double ZEP/AGP mutant 2).

The present inventors have also deposited *Chlamydomonas reinhardtii* double ZEP/AGP mutant 1 (dZA1) among the above selected mutant strains at the Korea Research Institute of Bioscience and Biotechnology Biological Resource Center (KCTC) on Oct. 15, 2018, and was given accession number KCTC 13659BP.

It was confirmed that both of the above mutant strains have improved lipid production ability as well as production of lutein and zeaxanthin because of effective double ZEP/AGP gene knockout. In particular, a vegetable oil derived from the mutant strain of the present invention has higher contents of xanthophyll-based pigments with antioxidant properties such as lutein and zeaxanthin than oils derived from wild-type strains so as to provide oils having high functionality and improved storage stability, thereby being more industrially useful. Further, the mutant strain having double knockout of the present invention may have faster growth rate compared to wild-type strains, and may be used very effectively in order to produce or provide microalgae-derived materials on an industrial scale.

The mutant strain of the present invention is viable even in dim light and can be cultured under specific light conditions ranging from 10 to 2,000 μmol photons/$m^2$s. In complete darkness with less than the dim light condition, the mutant strain cannot conduct photosynthesis. On the other hand, cells may be damaged by light stress under a condition of too strong light. When the mutant strain of the present invention is cultured under the above specific conditions, there is an advantage of having a high content of zeaxanthin in the mutant strain while achieving excellent growth rate.

The mutant strain of the present invention may be grown appropriately in a growth environment (brightness condition, temperature condition, medium, etc.) capable of culturing normal *Chlamydomonas reinhardtii* algae. Further, the mutant strain may have excellent lipid-producing ability even at low luminosity, and is industrially useful as a vegetable oil-producing microorganism due to fast cell growth rate. Further, the mutant strain may have a relatively lower density in colony even under high luminosity, as compared to other algae, which makes it possible to achieve excellent efficiency of pigment production by photosynthesis in single cells. Specifically, wild-type *Chlamydomonas reinhardtii* produces very little zeaxanthin, whereas the mutant strain of the present invention can produce zeaxanthin unlike the wild-type strain and has an increased lipid production ability of 10 to 20% or more and a fast growth rate increased by 20% or more. Therefore, this mutant strain is very suitable as a vegetable oil producing strain.

The mutant strain of the present invention may be cultured according to the culture conditions for general *Chlamydomonas reinhardtii*, and specifically, a culture medium in which algae can be cultured under dim light conditions may be used. In order to cultivate a specific microorganism, a material for specific purposes including nutritional substances required for a culture subject, that is, a microorganism to be cultured, may further be added and mixed with the culture medium. The medium may also be referred to as a culture or a culture solution, which is a concept including all of natural medium, synthetic medium or selective medium. The *Chlamydomonas reinhardtii* mutant strain may be cultured according to a conventional culture method. For example, the mutant strain may be cultured with a photosynthetic medium, that is, HS medium or TAP medium, and may further include a carbon source. In one embodiment, in environments establishing desired culture solution of Table 1 or Table 2 in the examples of the present invention, it was confirmed that the mutant strain of the present invention has excellent production ability of vegetable oil with enhanced antioxidant pigment content.

A pH range of the culture medium is not particularly limited as long as *Chlamydomonas reinhardtii* is viable and growable in the above range, for example, pH 6 or higher, specifically pH 6 to pH 9, and an optimum growth rate may be achieved in the range of pH 7.0 or higher to pH 8.0 or lower.

The mutant strain of the present invention may be produced by directly introducing the mutant strain into a target sequence in a ZEP gene and an AGP gene through RGENRNP using CRISPR gene scissors technology.

The *Chlamydomonas reinhardtii* mutant strain of the present invention may accumulate xanthine as a xanthophyll-based pigment as well as lipids in high contents in cells, whereby the pigment derived from the mutant strain of the present invention or a lipid including the pigment may be effectively used as raw materials of food, feed, medicines, etc.

In such aspects as described above, the present invention may provide a culture of the *Chlamydomonas reinhardtii* mutant strain.

Further, the present invention may provide a composition including at least one selected from the group consisting of a *Chlamydomonas reinhardtii* mutant strain and cultures thereof. The composition may be a cosmetic composition, a food composition, a composition for food additives, a feed composition, a composition for feed additives, a pharmaceutical composition, a food raw material composition, a feed raw material composition or a pharmaceutical raw material composition.

In the present invention, the "culture (product)" refers to a medium in which a specific microorganism has been cultured, that is, a medium after cultivation, wherein the culture includes all of the *Chlamydomonas reinhardtii* mutant strain or a residue remaining after culturing the mutant strain and then removing the mutant. The culture of the present invention may include all of the concentrate, dried product and extract of the culture medium, which are obtained after culturing followed by concentration, drying and extraction of the culture medium. Further, the culture may include by-products of the above process, and a formulation thereof is not limited and may be, for example, liquid or solid.

The medium is a liquid or solid material containing nutrients required for a culturing subject, that is, microorganisms to be cultured, in order to cultivate a specific microorganism, and may also include a material for special purposes which is further added and mixed. The medium is also called a culture or a culture solution and may include both natural and synthetic media. Further, the medium is a concept including both of a complete medium or a selective medium. pH range of the medium may be a range within which the *Chlamydomonas reinhardtii* mutant strain can be grown, for example, pH 6 or higher, preferably pH 6 to pH 9.

Further, the present invention relates to a composition including at least one selected from the group consisting of the *Chlamydomonas reinhardtii* mutant strain, a culture of the same, and a dried product or extract thereof.

The mutant strain of the present invention has a characteristic of generating xanthophyll-based pigments and lipids containing zeaxanthin and accumulating the same in the body. In this aspect, the composition may be a vegetable oil composition.

According to one embodiment of the present invention, as a result of measuring a content of zeaxanthin in total pigments per cell of the *Chlamydomonas reinhardtii* wild-type algae, it was confirmed that the *Chlamydomonas reinhardtii* mutant strain has a remarkably higher zeaxanthin content in the pigment as compared to the wild-type, and further shows excellent lipid production ability (FIG. 12B, FIG. 13A and FIG. 13B).

The composition may be used as a raw material for food or feed, and may be used as a preparation for oral administration or parenteral administration. For example, the composition of the present invention may be used as a formulation for oral administration or injection administration. Accordingly, the composition of the present invention may be a composition for oral administration since the composition or an extract-containing composition may be supplied orally while being contained in food, medicines or feed.

For the composition for oral administration, this composition may be included in oral formulations formulated by conventional methods known in the art, such as powder, granules, tablets, pills, lozenges (sugar-coated tablets), capsules, liquid, gel, syrup, slurries, suspensions, etc. for example, oral preparations may be produced in the form of tablets or lozenges by blending active ingredients with a solid excipient and then grinding the same, followed by addition of a suitable adjuvant thereto and then processing the same into a granular mixture. Examples of such suitable excipients may include: sugars such as lactose, dextrose, sucrose, sorbitol, mannitol, xylitol, erythritol and maltitol, etc.; starches such as corn starch, wheat starch, rice starch and potato starch, etc.; celluloses such as cellulose, methylcellulose, sodium carboxymethyl cellulose and hydroxypropylmethyl cellulose, etc.; and fillers such as gelatin, polyvinylpyrrolidone, etc. Further, if necessary, cross-linked polyvinylpyrrolidone, agar, alginic acid or sodium alginate, etc. may be added as a disintegrant.

The composition may be used for promoting health of humans and animals. Specifically, since the mutant strain of the present invention has vegetable oil production ability with improved antioxidant pigment content, thereby providing oil with less acidification, higher functionality and superior antioxidant activity to conventional vegetable oils derived from microalgae. Therefore, the mutant strain of the present invention may be effectively used as a raw material for food, health functional food, feed, medicines, etc.

Further, the composition may be added to the food or feed in order to achieve a special purpose and, in this aspect, may include a food composition, food additive composition, feed composition or feed additive composition. In the case of using the composition in food or feed, zeaxanthin and other pigments and lipids produced by the *Chlamydomonas reinhardtii* mutant strain and accumulated in cells may maintain or enhance health.

In the present invention, "use of additives" may include any configuration of additives added to the food or feed in addition to the main raw material. Specifically, the additive may include active materials having functionality in food or feed or food additives added for coloring, preservation, etc. in processed food products, which are defined by Korea Food and Drug Administration. Herein, the food may be a health functional food. More particularly, the food may be a health functional food for eye health.

The composition for food or food additives or the composition for feed or feed additives may further include other active ingredients in a range that does not impair the activity of the *Chlamydomonas reinhardtii* mutant strain of the present invention, a culture solution of the mutant strain, dried products and extracts thereof. Further, additional components such as a support or carrier may be further included.

The composition for feed according to the present invention may be produced in the form of fermented feed, blended feed, pellets and silage. The fermented feed may include the

*Chlamydomonas reinhardtii* mutant strain of the present invention, dried cells of the mutant strain, a culture of the mutant strain and extracts thereof, and may be prepared by adding various microorganisms or enzymes thereto. The blended feed may be prepared by mixing various types of general feeds, the mutant strain of the present invention, dried cells of the mutant strain, a culture of the algae and extracts thereof. Feed in the form of pellets may be prepared by formulating the fermented feed or blended feed in a pellet machine. Silage may be prepared by mixing cultivar feed with the *Chlamydomonas reinhardtii* mutant strain, dried cells of the mutant strain, a culture of the mutant strain and/or extracts thereof, however, use of the composition of the present invention is not limited thereto.

The composition may be mixed with a carrier and a fragrance commonly used in the food or pharmaceutical field, so as to produce tablets, troches, capsules, elixirs, syrups, powders, suspension or granules, etc., which may be administered. As the carrier, an excipient, a solubilizer, a dispersant, a stabilizer, a suspending agent, etc. may be used. The administration method may include oral or parenteral administration or local application methods, however, oral administration is preferably used. Further, a dosing amount, that is, a dosage, may be appropriately determined based on absorption of the active ingredients in the body, rates of inactivation and excretion, age, sex, and conditions of recipients. pH of the composition may be easily changed depending on the manufacturing conditions, such as a drug and food to which the composition is applied.

The composition may include 0.001 to 99.99% by weight ("wt. %"), preferably, 0.1 to 99 wt. % of any one selected from the group consisting of a *Chlamydomonas reinhardtii* mutant strain, a culture of the mutant strain, dried products of the mutant strain or culture, and extracts of the mutant strain or culture based on a total weight of the composition, and the contents of the active ingredients may be appropriately adjusted according the methods and purposes of using the composition.

The *Chlamydomonas reinhardtii* mutant strain may be included in the composition as it is or in dried form, and the culture of the algae may be included in the composition in a concentrated or dried form. In this case, the dried material refers to a dried form of the algae or culture thereof, and may be in the form of powder prepared by lyophilization.

Further, the extract may be obtained from the *Chlamydomonas reinhardtii* mutant strain of the present invention, a culture solution or a dried product thereof through extraction, and may include an extract obtained using a solvent, etc., or a product obtained by crushing the *Chlamydomonas reinhardtii* mutant strain of the present invention. More particularly, the extract may be obtained by extracting and isolating a pigment accumulated in the cells of the *Chlamydomonas reinhardtii* mutant strain of the present invention according to any mechanical or chemical method.

The extraction process may be conducted by a conventional method, for example, by adding an extraction solvent, homogenizing the same, and crushing the cells to extract the desired pigment. After extraction, the crushed algae material is removed by centrifugation, and the extraction solvent may be removed by distillation under reduced pressure. Further, the extraction process may further include a conventional purification process. The pigment is insoluble in water and may be more easily extracted from the algae of the present invention.

The *Chlamydomonas reinhardtii* mutant strain of the present invention has excellent xanthophyll, in particular, zeaxanthin production ability at a low light intensity (that is, luminosity), therefore, the composition including the above mutant strain and by-products thereof may exhibit improvement in physical activity, maintaining of body functionality, and effects of preventing degradation of body functionality. Specifically, the xanthophyll pigment is known to have macular degeneration inhibitory effects, antioxidant effects, anti-cancer effects, etc. Further, since the microalgae-derived vegetable oil is an effective source of unsaturated fatty acids, the composition of the present invention may be used as a raw material included in foods, health functional foods, medicines or feeds for purposes of maintaining body health, specifically, maintaining the body health with participation of xanthophylls pigments and unsaturated fatty acids, preventing deterioration therefore or improving the same.

Further, another object of the present invention is to provide a method for production of vegetable oil using the *Chlamydomonas reinhardtii* mutant strain of the present invention. The production method may include culturing the *Chlamydomonas reinhardtii* mutant strain of the present invention.

Further, another object of the present invention is to provide a method for production of a raw material for medicines, food or feed, which includes culturing the *Chlamydomonas reinhardtii* mutant strain of the present invention.

Using the mutant strain of the present invention may obtain a high growth rate so that a subject material can be quickly recovered. Further, because of high zeaxanthin production ability and lipid production ability, a storage period may become longer. Further, the mutant strain of the present invention is effectively useable in providing vegetable oil with excellent antioxidant activity. Therefore, the mutant strain of the present invention may attain great advantages in consideration of the above effects.

Further, the production method may further include isolating the *Chlamydomonas reinhardtii* mutant strain of the present invention from the culture after the culturing step. The isolated algae may be subjected to further processing steps including drying.

The production method may further include separating lipid from the culture of the *Chlamydomonas reinhardtii* mutant strain of the present invention. The separation of lipid may be conducted using known methods for separating metabolites from microalgae. The present invention is characterized by excellent ability to produce lipid and antioxidant xanthophyll-based pigment from the *Chlamydomonas reinhardtii* mutant strain of the present invention, therefore, it is not limited to the above known methods. For example, an enzyme method, an ultrasonic extraction method and a mechanical extraction method may also be used but are not limited thereto.

The culturing may be implemented in a medium at pH 6.0 to 8.0. Further, the culturing may be conducted under dim light conditions, specifically, a luminosity condition in the range of 10 to 2,000 μmol photons/$m^2$s. In the case of the *Chlamydomonas reinhardtii* mutant strain of the present invention, the pigment production ability is excellent even at a low light intensity so as to increase a content of zeaxanthin in the body so that excellent zeaxanthin accumulation can be achieved even without applying high luminosity, thereby being effectively useable on an industrial scale.

In addition to the culturing step, the production method may further include a concentrating process of increasing a content of algae after culturing, and a drying process to dry the algae by further reducing moisture of the algae after the concentration process. However, the concentrating process or the drying process is not necessarily required and may be generally conducted using any concentration and drying method as well as an apparatus commonly used in the art, to which the present invention pertains.

The production method may further include a process of purifying the material separated from the culture, which may be implemented by a conventional purification method.

The vegetable oil obtained after the above processes may be used as a raw material for food, health functional food, cosmetics or pharmaceuticals.

The vegetable oil production method of the present invention may be performed by adopting other methods within the range not impairing the effects of the present invention. Description in regard to the mutant strain and the composition may also be employed in the production method of the present invention.

Further, the present invention provides a method for preparation of a *Chlamydomonas reinhardtii* mutant strain with improved oil production ability, which includes a ZEP gene mutation and an AGP gene mutation, in particular: mutation of ZEP genes while targeting the 800th to 820th bases in the ZEP gene sequence of *Chlamydomonas reinhardtii* represented by SEQ ID NO: 1; and mutation of AGP genes while targeting the 100th to 120th bases in the AGP gene sequence of *Chlamydomonas reinhardtii* represented by SEQ ID NO: 2.

Further, the present invention may provide use of the above mutant strain in order to produce a food, feed, food raw material or feed raw material.

Further, the present invention may provide use of the above mutant strain in order to produce cosmetics, pigments, oil or raw materials thereof.

Description in regard to the mutant strain and the composition may also be employed in the production method and use of the present invention.

The gene mutation may be performed by transformation of *Chlamydomonas reinhardtii* cells with the preassembled complex that include polynucleotides expressing a single guide RNA (sgRNA) containing a sequence of target gene, as well as Cas protein.

More particularly, the gene mutant may include the ZEP gene mutant and the AGP gene mutant, in particular: a ZEP gene mutant in which adenine A, a base sequence represented by SEQ ID NO: 3 or a base sequence represented by SEQ ID NO: 5 is inserted between the 816th base and the 817th base in the ZEP gene sequence of *Chlamydomonas reinhardtii* represented by SEQ ID NO: 1; and the AGP gene mutant in which adenine A is inserted between the 116th base and the 117th base in the AGP gene sequence of *Chlamydomonas reinhardtii* represented by SEQ ID NO: 2, otherwise, the 115th base is deleted while the 116th base is substituted by thymine T.

According to the method for preparation of the mutant strain of the present invention, the microalgae are free from the risk of GMO because the microalgae contain no external genes, and the vegetable oil extracted from the microalgae of the present invention has a high content of xanthophyll-based pigments such as lutein and zeaxanthin having antioxidant activity, thereby having excellent oil preservation and stability. Therefore, the present invention may be effectively used in industrial applications such as food, medicine and cosmetics.

Hereinafter, the present invention will be described in more detail by means of examples, and the following examples are merely illustrative of the present invention, and the contents of the present invention are not interpreted to be limited by the following examples.

Example 1—Culture of Strain

In one embodiment of the present invention, *Chlamydomonas* algae were cultured under the following medium and culture conditions unless otherwise specified.

1-1) Independent Nutrition Culture

In the case where autotrophic culture is performed using only photosynthesis without supply of an external carbon source, the culturing was conducted by supplying 5% $CO_2$ in HS medium as a minimal medium. After the medium having the composition shown in Table 1 was autoclaved for sterilization under a high pressure, cells in a vigorous growth stage were prepared to a concentration of $10^6$ cells/mL in the culture medium to start growth. As a culture vessel, a glass column as shown in FIG. 11 was used, and air was supplied from the bottom (bubbles). Then, light at a luminosity of 200 uE was provided from both sides using a fluorescent lamp.

TABLE 1

| Components of HS media | Concentration in culture solution (mM or μM) |
|---|---|
| Buffer and major components (mM) | |
| $NH_4Cl$ | 9.345 |
| $MgSO_4 \cdot 7H_2O$ | 0.08 |
| $CaCl_2 \cdot 2H_2O$ | 0.07 |
| $K_2HPO_4$ | 8.265 |
| $KH_2PO_4$ | 5.29 |
| Minor component (μM) | |
| $ZnSO_4 \cdot 7H_2O$ | 765 |
| $H_2BO_2$ | 922 |
| $MnCl_2 \cdot 4H_2O$ | 511 |
| $CoCl_2 \cdot 6H_2O$ | 7 |
| $CuSO_4 \cdot 5H_2O$ | 126 |
| $(NH4) Mo_7O_{14} \cdot 4H_2O$ | 18 |
| $FeSO_4 \cdot 7H_2O$ | 18 |
| EDTA disodium salt | 134 |
| Miscellaneous | |
| Carbon source | 5% CO bubble, 80 cc/min |
| pH in culture solution | 7.0 |
| Luminosity | 200 uE |

2) Culture of Mixed Nutrition

In the case of the mixed nutrient culture (Mixotrophic culture) in which photosynthesis and a carbon source are supplied at the same time to culture, acetic acid was added to the TAP medium and cultured. After preparing the medium having the composition shown in Table 2, autoclaving/sterilization at a high pressure were performed in an autoclave, and cells in an active growth stage were prepared to a concentration of $10^6$ cells/mL in the culture medium to start growth. As a culture vessel, a glass flask or bottle as shown in FIG. 12 was used to culture in a large volume while stirring using a magnetic bar. A fluorescent lamp was used to provide light at a luminosity of 70 uE.

TABLE 2

| Components of TAP media | Concentration in culture solution (mM or μM) |
|---|---|
| Buffer and major components (mM) | |
| $NH_4Cl$ | 7.5 |
| $CaCl_2 \cdot 2H_2O$ | 0.675 |
| $MgSO_4 \cdot 7H_2O$ | 0.8 |
| $K_2HPO_4$ | 0.62 |
| $KH_2PO_4$ | 0.41 |

TABLE 2-continued

| Components of TAP media | Concentration in culture solution (mM or μM) |
|---|---|
| Minor component (μM) | |
| EDTA•2H₂O | 135 |
| FeSO₄•7H₂O | 18 |
| ZnSO₄•7H₂O | 75 |
| H₃BO₃ | 185 |
| MnCl₂•4H₂O | 26 |
| CuCl₂•2H₂O | 6.5 |
| Na₂MoO₄•2H₂O | 5.5 |
| CoCl₂•6H₂O | 6.5 |
| Miscellaneous | |
| Carbon source | Glacial acetic acid, 1 ml/L |
| Tris | 2.42 g/L |
| pH in culture solution | 7.2 |
| Luminosity | 70 uE |

Example 2—Use of CRISPR Gene Scissors Technology (CRISPR-Cas9 RNP) for Preparation of ZEP Gene Knockout *Chlamydomonas* Mutant Strain In order to target *Chlamydomonas reinhardtii* ZEP gene (phytozome: Cre02.g082550 or NCBI: AY211267.1) [phytozome.jgi.doe.gov/pz/portal.html #!gene?searc h=1& detail=1&method=4614&searchText=transcriptid: 30785220; pre sent at position 1244277-1250969 in chromosome 2], five (5) sgRNAs inducing microhomology-driven frame shift mutation were designed by Cas-Designer (www.rgenome.net), followed by synthesis through in vitro transcription. Target sequences of the five sgRNAs designed and prepared to target the ZEP gene according to Cas-designer (www.rgenome.net/cas-designer/) are shown in Table 3 below.

homology-mediated end joining (MMEJ) pathway. "#of target-off site" means the number of mismatched sequences throughout the whole genome. When the remaining sgRNA sequence (Gttttagagctagaaatagcaagttaaaataaggctagtccgttat-caacttgaaaaag tggcaccgagtcggtgc, SEQ ID NO: 15) is linked to the target sequence, the entire sgRNA is represented.

In the case of Cas9 protein, a recombinant Cas9 protein was expressed using *E. coli* and prepared after purification. The wild-type *Chlamydomonas* reinharddtii cw15 mt (CC-4349) used in the experiment was obtained from *Chlamydomonas* Resource Center (www.chlamycollection.org) [www.chlamycollection.org/product/cc-4349-cw15-mt-goodenough-330a/].

The *chlamydomonas* cells were placed in a 50 ml flask at 25° C. using TAP medium of Table 2, followed by emitting light at a luminosity of 70 uE using a fluorescent lamp and culturing the same while shaking at 90 rpm. A concentration of the cells was measured using a spectrophotometer, wherein the cells under active culturing in a level of 0.3 to 0.5 at $OD_{750}$ were used.

To prepare an RNP complex, 100 μg of Cas9 protein (FIG. 5, SEQ ID NO: 16) was mixed with 70 μg of sgRNA (SEQ ID ID NO: 17, the front 20 bp is a portion that binds to the target sequence of DNA; and the rest of the sequence is a sequence to form a complex with Cas9 protein wherein the front 20 bp depends on the target sequence in Table 3) in nuclease-free water, and incubated at room temperature for 10 minutes. The bound RNP complex was transformed along with $50 \times 10^4$ wild-type *Chlamydomonas reinhardtii* cw15 mt (CC-4349) cells through electroshock in a 4 mm electroporation cuvette by BIORAD GENE PULSER XCELL™ Electroporation System (Voltage 600V, Capacity 50 μF). After incubation for 12 hours in dark conditions, gDNA was extracted and analyzed by targeted deep sequencing, some were diluted to 2000 cells and plated on a TAP agar plate to obtain a single colony.

TABLE 3

| #RGEN | Target (5' to 3') | Position | Cleavage Position | Direction | GC Contents (w/o PAM) | Out-of-frame Score | Mismatch 0 | Mismatch 1 | Mismatch 2 |
|---|---|---|---|---|---|---|---|---|---|
| RGEN1 | CACCAGCTGCGCGACCGAGCTGG | 638 | 9.732573433 | — | 75 | 84.3 | 1 | 0 | 0 |
| RGEN2 | GCCGTTGCACTTCTGAAGCAGGG | 724 | 13.98509426 | + | 55 | 75.3 | 1 | 0 | 0 |
| RGEN3 | TCCGGCGAACGCACCTGGATGGG | 911 | 17.31696624 | — | 65 | 75.4 | 1 | 0 | 0 |
| RGEN4 | TGGTGGGCGCCGACGGCATCTGG | 2569 | 33.97632617 | + | 75 | 88.2 | 1 | 0 | 0 |
| RGEN5 | CCATGGCTTCGCAGGCATCTCGG | 2868 | 37.26435774 | + | 60 | 71.2 | 1 | 0 | 0 |

In TABLE 3, the #RGEN Target (5' to 3') sequences are RGEN1(SEQ ID NO: 10), RGEN2(SEQ ID NO: 11), RGEN3(SEQ ID NO: 12) RGEN4(SEQ ID NO: 13), RGEN5(SEQ ID NO: 14)].

Figure 3B:
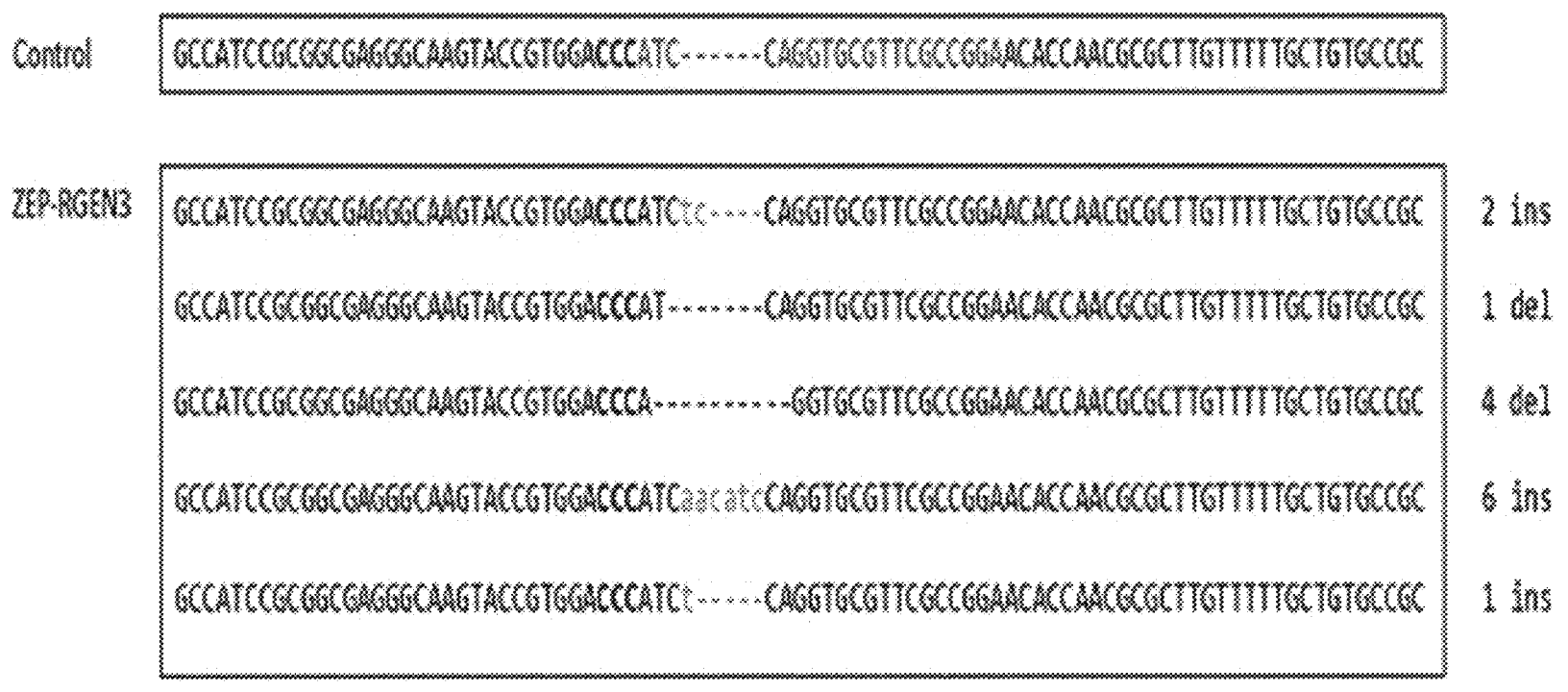

Five (5) sgRNAs were carefully designed within half of a coding sequence region of the ZEP gene, which differs from any other target sites by 3 nucleotides (nt) among the whole genome and has an out-of-frame score higher than 66. "CDS (coding sequence) position" refers to a relative position of a cleavage point in RNA transcript. "+" of direction is the same direction as the target sequence, that is, indicating that the same sequence is a sequence of RGEN. Similarly, "−" of direction is the reverse direction to the target sequence, that is, indicating that the sequence is a sequence coupled to the target sequence so as to be complementary to each other (reverse complement). "Out-of-frame score" means a possibility of frame shift-induced deletion occurring when a broken double-stranded DNA is repaired through a micro- FIGS. 3A and 3B illustrate a result of confirming mutation of the ZEP gene induced by RGEN-RNPs according to targeted deep sequencing. A single colony induced by the third sgRNA (0.456%), which has the highest transformation efficiency, was isolated to identify mutation of the target gene. FIG. 3B illustrates a result of target deep sequencing, wherein, when all cells were collected after transformation experiments using RNP and then gDNA was extracted and analyzed, all mutations occurring in the DNA strand of the target site were analyzed to identify pattern and frequency thereof. However, FIG. 3B shows the patterns of mutations actually identified at the target site through targeted deep sequencing. Since a large-scale change such as insertion of 42 bp or more is hardly found on the basis of the principle of targeted deep sequencing, there may be a difference between the found mutation and that of the actually obtained single colony [Control—SEQ ID NO: 18, ZEP-RGEN3 (2ins—SEQ ID NO: 19, 1del-SEQ ID NO: 20, 4del—SEQ ID NO: 21, 6ins—SEQ ID NO: 22, 1ins—SEQ ID NO: 23)].

After the ZEP gene-specific knockout mutant was generated using DNA-free RGENRNP, all cells in a Petri dish were subjected to Ch1 fluorescence measurement, and several putative ZEP knockout cell-lines were selected.

In FIG. 6A, red circles indicate putative ZEP knockout mutants grown on TAP agar medium under dim light (50 µmol photons/m$^2$s) conditions. NPQ/4 images were measured with Imaging PAM (Walz). Single cell colonies of wild-type (WT) and ΔZEP mutants were grown on minimal agar medium under dim light (50 µmol photons/m$^2$s) conditions (FIGS. 6A and 6B). Three mutants (ΔZ1, ΔZ2, ΔZ3) with increased macular pigment contents were selected from the identified colonies, and a change in target DNA sequences at the actual ZEP gene positions in three ZEP mutants generated by RGEN RNPs was determined through Sanger sequencing (FIGS. 2A, 2B, 2C, 2D, 2E and 2F).

As shown in FIG. 6B, it was confirmed that the colonies of the wild-type Chlamydomonas reinhardtii cw15, and mutants ΔZ1, ΔZ2 and ΔZ3 were grown in similar forms and sizes in TAP agar plates. Further, in the case of cells liquid-cultured in HS medium through photosynthesis, it was confirmed that the wild-type Chlamydomonas reinhardtii algae have green color while the mutantsΔZ1, ΔZ2 and ΔZ3 exhibit a color similar to yellowish-green (FIG. 6C).

Among the starting mutant strains, mutant strain Z1 was named Chlamydomonas reinhardtii ZEP mutant 1 (ΔZ1), which was deposited at the Korea Research Institute of Bioscience and Biotechnology Biological Resource Center (KCTC) at 181, Ipsin-gil, Jeongeup-si, Jeollabuk-do 56212, Republic of Korea on Mar. 22, 2014 in accord with the provisions of the Budapest Treaty for the Deposit of Microorganisms, and given accession number KCTC 13230BP.

Thereafter, the mutant strain Z1 was used for double gene correction.

Example 3—Preparation of AGP (ADP Glucose Pyrophosphorylase) Gene Knockout Chlamydomonas Mutant Strain Using CRISPR Gene Scissors Technique (CRISPR-Cas9 RNP) in Chlamydomonas To target the AGP gene, four (4) sgRNAs inducing microhomology-driven frame shift mutation were prepared by Cas-Designer (www.rgenome.net). The four sgRNAs prepared to target the AGP gene are shown in Table 4 below (see Table 3 for the meaning of each item).

In order to prepare an RNP complex, 100 µg of Cas9 protein (FIG. 5, SEQ ID NO: 16) was mixed with 70 µg of sgRNA (e.g.: SEQ ID NO: 28, the front 20 bp is a portion that binds to the target sequence of DNA; and the rest of the sequence is a sequence to form a complex with Cas9 protein wherein the front 20 bp depends on the target sequence in Table 3) in nuclease-free water, and incubated at room temperature for 10 minutes. The bound RNPs complex was transformed along with 50×10$^4$ Chlamydomonas reinhardtii cells in a 4 mm electroporation cuvette by Biorad Gene Pulser Xcell™ Electroporation System (Voltage 600V, Capacity 50 µF). After incubation for 12 hours in dark conditions, gDNA was extracted and analyzed by deep sequencing. Further, some were diluted to 2000 cells and plated on a TAP agar plate to obtain a single colony.

FIGS. 7A and 7B illustrate gene information and target sequence of AGP of the wild-type Chlamydomonas reinhardtii algae. FIG. 8b illustrates a result of confirming a change in target DNA sequences at the actual AGP gene positions in two mutant stains. FIGS. 9A, 9B, 9C and 9D illustrate changes in target DNA sequences at AGP gene positions in the mutants dZA1 and dZA2 selected through the gene correction which was confirmed through Sanger sequencing.

Example 4—Assessment of Cellular Characteristics of Mutant Strains of ZEP/AGP Double Gene Knockouts As described above, cellular characteristics of the mutants (dZA1 and dZA2) of two ZEP/AGP double knockouts separated in single colonies were assessed.

FIG. 10A is a photograph showing comparison of colors between the wild-type Chlamydomonas strain and the ZEP/AGP double knockout mutants of the present invention generated by CRISPR-Cas9 RNP at the same concentration.

Further, a starch discoloration reaction using Lugol's solution in a nitrogen-depleted environment of cells was compared to confirm whether AGP knockout was well performed. Cells were cultured in a nitrogen-rich medium and a nitrogen-depleted medium, respectively, to obtain healthy cells. 1 µl of Lugol's solution was added to 1 ml of cell culture solution at $OD_{750}=1$, cells were uniformly mixed for 30 seconds, and then, colors responding to the Lugol's solution were compared according to nitrogen conditions.

Under nitrogen depletion conditions, the cells are stressful to allow accumulation of starch and lipids in the cells. In the

TABLE 4

| AGP4 sgRNA | RGEN Target (5' to 3') | Position | Cleavage Position (%) | Direction | GC Contents (%, w/o PAM) | Out of frame Score | Mismatches 0 | 1 | 2 |
|---|---|---|---|---|---|---|---|---|---|
| AGP4_sg1 | TAGCATGGCCCTGAAGATGCGGG SEQ ID NO: 24 | 100 | 4.6 | + | 55 | 48.9 | 1 | 0 | 0 |
| AGP4_sg2 | CAGACCTTCGTCTGCCCCCACGG SEQ ID NO: 25 | 149 | 12.9 | + | 65 | 68.9 | 1 | 0 | 0 |
| AGP4_sg3 | GACTCATCTCGCAGGCTCAGTGG SEQ ID NO: 26 | 229 | 20.1 | + | 60 | 70.1 | 1 | 0 | 0 |
| AGP4_sg4 | GTCGACCCCCGTTGAGACCAAGG SEQ ID NO: 27 | 393 | 41.6 | + | 65 | 45.7 | 1 | 0 | 0 | case of wild-type strains, it could be seen that intercellular starch is stained with Lugol's solution in the nitrogen depletion conditions and becomes purple. However, the ZEP/AGP double knockout mutants inhibited starch synthesis due to knockout of the AGP gene, thereby not causing discoloration due to Lugol's solution even in a nitrogen-depleted environment. Therefore, as shown in FIG. 10B, it could be confirmed that AGP knockout was desirably performed in the ZEP/AGP double knockout mutant of the present invention.

In order to compare the cell growth rates between the wild-type *Chlamydomonas reinhardtii* cw15 algae and ZEP/AGP double knockout mutants, culture experiments were conducted at a luminosity of 50 µmol photons/m$^2$ in TAP medium as a mixed nutrient medium. The initial inoculation cell number was 1×10$^6$ cells/ml, and the cell number was measured at 12 hour intervals for 72 hours in order to draw a growth curve.

As shown in FIG. 11, it could be seen that the ZEP/AGP double knockout mutants rapidly increased the number of cells per volume compared to the wild-type. In particular, it could be seen that the dZA1 mutant showed a rapid growth rate of 20% compared to the wild-type algae.

Example 5—Assessment of Lipid and Pigment Content of ZEP/AGP Double Gene Knockout Mutants In order to compare a difference in pigment contents between the mutant strain of the present invention and the wile-type strain, the cell pigment profile of each strain was analyzed using HPLC.

The separated single colonies were cultured in TAP medium for 3 days under 70 µmol photons/m$^2$s conditions. Specific culture conditions applied herein were substantially the same as the culture conditions of Example 1. The harvested algae were analyzed by extracting the pigment using 90% acetone and centrifuging the supernatant again through a nylon filter and injecting the same into an HPLC. Specifically, in order to separate the pigment, a total flow rate of the solvent was set to 1.2 mL per minute, and Tris with pH 8.0 and acetonitrile were uniformly reduced from 14% and 84%, respectively, to 0% at a time period of 0 to 15 minutes. Further, methanol and ethyl acetate started at 2% and were increased up to 68% and 32%, respectively, until 15 minutes. Thereafter, a ratio of the solvent was maintained for 3 minutes (from 15 minutes to 18 minutes), and then, returned to the original ratio of each solvent at the beginning for 1 minute (from 18 minutes to 19 minutes), followed by conducting post-run while maintaining the same for the remaining 6 minutes. A pump used herein was a Shimadzu LC-20A Prominence, and the column was a Waters Spherisorb TMS5 (DS1 4.6×250 mm, 5 µm Cartridge Column, USA) wherein a temperature of the column was maintained at 40° C. Further, a photodiode array detector (SPD-M20A, Shimadzu) was used to analyze the data, and carotenoid pigments including zeaxanthin were detected at 445 nm while detecting chlorophyll a at 670 nm. Further, a concentration of each pigment was determined from the detected results, using standard curves for quantification of carotenoids and chlorophylls a and b, which were purchased from DHL (Agern Alle, Horsholm, Denmark).

FIG. 12A is a graph showing results of analyzing the pigment profile of the wild-type (WT) strain and mutants dZA1 and dZA2 (ZEP/AGP double knockout mutants generated by CRISPR-Cas9 RNP), while FIG. 12B is a graph showing comparison of the contents of lutein and zeaxanthin per cell. In the wild-type strain, zeaxanthin is almost nonexistent. However, with regard to the mutant strain of the present invention, it could be confirmed that the content of zeaxanthin in the cell was significantly increased. Further, the contents of lutein and zeaxanthin per volume were measured over time, and the results thereof are shown in FIGS. 12C and 12D, respectively. In the case of the wild-type strain, it was also confirmed that no zeaxanthin was produced at all, and the zeaxanthin content increased over time only in each mutant strain. Therefore, it could be seen that the mutant strains of the present invention have different mycological characteristics and pigment production abilities as compared to the wild-type strains.

Further, in order to confirm the lipid production ability of the ZEP/AGP double gene knockout mutants, lipid contents of the wild-type and mutant strains of the present invention were analyzed in a nitrogen-depleted environment. The lipid contents of the wild-type strains and mutants dZA1 and dZA2 were measured using a Nile-Red staining solution that can determine TAG (Triacylglycerol) (FIG. 13A), respectively. Further, a content of total cell lipids extracted using an organic solvent extraction method was measured (FIG. 13B).

As shown in FIGS. 13A and 13B, it could be seen that the mutants dZA1 and dZA2 of the present invention have lipid production abilities improved by about 10 to 20% or more compared to the wild type strains. When combined with the result shown in FIG. 12, it could be understood that contents of the antioxidant pigments such as lutein and zeaxanthin are also high, thereby achieving excellent properties.

ACCESSION NUMBER

Depository name: Korea Research Institute of Bioscience and Biotechnology
Accession number: KCTC13659BP
Date of accession: 20181015

The invention claimed is:

1. A *Chlamydomonas reinhardtii* mutant strain, comprising:
   a ZEP gene mutant in which adenine (A), a base sequence of SEQ ID NO: 3 or a base sequence of SEQ ID NO: 5 is inserted between an 816th base and an 817th base in a *Chlamydomonas reinhardtii* ZEP gene sequence of SEQ ID NO: 1; and
   an AGP gene mutant in which adenine (A) is inserted between a 116th base and a 117th base in a *Chlamydomonas reinhardtii* AGP gene sequence of SEQ ID NO: 2, otherwise, a 115th base is deleted while the 116th base is substituted by thymine (T).

2. The mutant strain according to claim 1, wherein the mutant strain a mutated ZEP gene of SEQ ID NO: 4, SEQ ID NO: 6 or SEQ ID NO: 7; and a mutated AGP gene of SEQ ID NO: 8 or SEQ ID NO: 9.

3. The mutant strain according to claim 1, wherein the mutant strain is characterized by having improved ability to produce lipids, zeaxanthin, and lutein, as compared to wild-type strains.

4. The mutant strain according to claim 1, wherein the mutant strain has a mutated ZEP gene of SEQ ID NO: 4; and a mutated AGP gene of SEQ ID NO: 8 or SEQ ID NO: 9.

5. A culture of the mutant strain according to claim 1.

6. A cosmetic composition comprising one or more selected from the group consisting of the mutant strain according to claim 1 and a culture thereof.

7. A composition for food or food additives comprising one or more selected from the group consisting of the mutant strain according to claim 1 and a culture thereof.

8. A composition for feed or feed additives comprising one or more selected from the group consisting of the mutant strain according to claim 1 and a culture thereof.

9. A method for production of vegetable oil comprising culturing the mutant strain according to claim 1 and separating lipid from the mutant strain and/or the culture of the mutant strain.

10. A method for production of a raw material of food comprising culturing the mutant strain according to claim 1 and isolating the cultured mutant strain and/or cultures thereof.

11. A method for production of a raw material of feed comprising culturing the mutant strain according to claim 1 and isolating the cultured mutant strain and/or cultures thereof.

12. A method for preparation of *Chlamydomonas reinhardtii* mutant strain having a ZEP gene mutation, an AGP gene mutation, and an improved oil production ability, said method comprising:
   mutating a ZEP gene by targeting 800th to 820th bases in the ZEP gene sequence of *Chlamydomonas reinhardtii*, wherein a wild-type ZEP gene sequence is a sequence of SEQ ID NO: 1; and
   mutating an AGP gene by targeting 100th to 120th bases in the AGP gene sequence of *Chlamydomonas reinhardtii*, wherein a wild-type AGP gene sequence is a sequence of SEQ ID NO: 2.

13. The method for preparation of a *Chlamydomonas reinhardtii* mutant according to claim 12, wherein the mutation of ZEP gene and the mutation of AGP gene are performed by transformation of *Chlamydomonas reinhardtii* cells with a preassembled complex that include polynucleotides expressing a single guide RNA (sgRNA) containing a sequence of a target gene and a Cas protein.

14. The method for preparation of *Chlamydomonas reinhardtii* mutant according to claim 12, wherein the ZEP gene mutant and the AGP gene mutant include:
   a ZEP gene mutant in which adenine (A) a base sequence of SEQ ID NO: 3 or a base sequence of SEQ ID NO: 5 is inserted between an 816th base and an 817th base in the ZEP gene sequence of *Chlamydomonas reinhardtii* of SEQ ID NO: 1; and
   an AGP gene mutant in which adenine A is inserted between a 116th base and a 117th base in the AGP gene sequence of *Chlamydomonas reinhardtii* of SEQ ID NO: 2, otherwise, a 115th base is deleted while the 116th base is substituted by thymine (T).

* * * * *

SEQUENCE LISTING

```
<160> NUMBER OF SEQ ID NOS: 28

<210> SEQ ID NO 1
<211> LENGTH: 6693
<212> TYPE: DNA
<213> ORGANISM: Chlamydomonas reinhardtii

<400> SEQUENCE: 1
gcgacgcacg gctgggccaa attcgccaac ggcaggagac caaatcgatc gaggcgatct      60
tgcgaagttc tcggacaaat cgatcgcacc catagtgatt taagcattac atttgcccaa     120
```

```
ggcgtgagaa gtgcgaggcc cgaacggcta tgacgccaat gcgcagctta cgacatttaa    180
agcaaattat tcatacatca tacagcacgc ttatgtgaag aaagccagga ttttaggctc    240 tcgcccgat  caagacgatc tccccattgc gaagttctcg gtttctttcc ggttcgcctg    300
ctccgtatga tttacctttg cgctacaaca gcgacttaaa cgacctacgt cgccttactg    360
tgtgcgcgta cgtgtttgta gctgtgagat agttttgtcc gcagcgtacc cgcaaataga    420
atgctcgcga gcacttacac gccctgtggc gttcgcagg  tggcaggccg cacgttgca    480 gtgcccagca gcttggtcgc gccagtggca gtcgctcggt cgctggggtt ggcgccctac    540
gtccctgtat gtgagccttc tgcggcgctt ccggcctgcc agcagcctag cgggcgtcgt    600
catgttcaga ctgctgccac tctccgtgcc gacaacccca gctcggtcgc gcagctggtg    660
catcagaatg gaaggggat  gaaggttatt atcgccggcg cgggcatcgg cggcctggtg    720
ctagccgttg cacttctgaa gcagggcttc caggttcagg tctttgagcg cgacctgacg    780
gccatccgcg gcgagggcaa gtaccgtgga cccatccagg tgcgttcgcc ggaacaccaa    840
cgcgcttgtt tttgctgtgc cgcgaccatg aactaggcct tatcttgagg tgttagcatg    900
tttagccagc gttggatctg tgtggcgagg ttggggtgag aacccttcct gtgtacctgc    960
tcgggcgtac cttgtgcccc accgctgact ggcttactta atgacaaaac gcaggttcaa   1020
agcaatgcgc tcgctgcgct ggaggctatc gatcccgagg tggccgcgga ggtgctgcgc   1080
gagggctgca tcactggcga ccgtatcaac gggctctgcg acggcctgac tggcgagtgg   1140
tgagtaggca atccagctgt gcatccagtc gcgcggttgc ggaggtcgtc tcgggaaacg   1200
cgacgtggcg tccactcgcc caaggagtgg tctcccgcag cgtggtctcc cgcagctcgg   1260
gtgcaacacc ctgcccccctg ccgcgagcgc gctgcgcttg cttatgttgc gcagcggtgt   1320
gagttacaac agcttctgtt gaagagctgt catacgaagc acggcgcgct gtggcgctgc   1380
agccgtgctg tggaaactcc aacacctcca ccgccagcct gcgcacgcac acgcaataca   1440
ctcgcctcgt gtgccccctc ctcacacaac ggcatgtgac actcagtttt aactcttatt   1500
ttgacagctg agagctacac gcttgggtga atggggaggt ccttgatgtt tcgttgcact   1560
ccgtggctcc ggagtccgtg cggaccgtca cccacaaatg ggagcgcacg gctttcttgt   1620
gctgtctgcc ccgttagcca ctaactgcga atgaccttga cagtttactt tgctattttt   1680
ccttccaggt acgtcaagtt cgacacgttc cacccggcgg tcagcaaggg cctgccggtg   1740
acccgcgtca tcagccgcct cacgctgcag cagatcctgg ccaaagccgt ggagcggtga   1800
gccgtgcgcg cggtgtgatg gctttagcgt cagtgctagc atgggggttg gtgggtggta   1860
atcgcggcgc ccatggccgg gtagcagcgg ccgaaagctg gcgcagagcg cgcgttggac   1920
aagcggtcct gttgccggta tgggcacgag cagggcgctg gtgcgggcaa agggcagagt   1980
ggagttgcag agcagcgctg gcgtcggctg tgcgctctcc aaatggcctc gtggcattct   2040
gacgggacac atcctggaaa atagtagcgc acccaactgc tggtggctcc tcgtacaatc   2100 ccccccaattt acaatcgctc gttctggctc gcagctacgg cggccccggc accatccaga   2160
acggctgcaa cgtgaccgag ttcacggagc gccgcaacga caccaccggc aacaacgagg   2220
tgagagcgtg ctaagaagag catgcacgtg gagcgtgtaa aattgtgtgg cctgaagcgg   2280
cagtgcctgc ggcatggact aggtggttgc agcatgctgc gcgcgtgggt tgccggtcag   2340
gaaaccgccg gaccgagccg cgcagattca gtcaggagcg gattaggaag tttgaaaaac   2400
agggttcgga gtgtgcaagc gggctcagga gctgtggtgc ctttctacac cggtcgccct   2460
```

```
accaggcacc cactgaaact gtaaaaccgt tgctgcgccg gcgatgccct ctacttcact   2520
aggtgactgt gcagctggag gacgggcgca cgtttgcggc cgacgtgctg gtgggcgccg   2580
acggcatctg gtccaagatc cgtaagcagc tcattggcga gaccaaggcc aactacagcg   2640
ggtacacctg ctacaccggt gagattattg accttcaagt tggaaggagg gagcgggggg   2700
agcggaatgg aaggaagcag cgtggacggg gcgcacggag gggaggggac tgcgggtcat   2760
agcgccgcct tgcggggcgt gaggagtgtt gggcggatat tcagttttct ttgcccaaga   2820
tcttcccaca atccgcgtgt gtctgacgcg ggatgtggcc cctgctgcca tggcttcgca   2880
ggcatctcgg actttacgcc ggcggacatt gacattgtgg gctaccgcgt gttcctgggc   2940 aacgccagt actttgtcag cagcgacgtg ggcaacggca agatgcagtg gtgagcggcg   3000
gcgggcgggc gagcgagggc tgcgggtct ggagggtgtg taccgggcgg aagggagggg   3060
aagggagggg aagggaaggc aggatgcagg cgagggcagg atgtgatggt gggaagaggg   3120
cgtggcgagc agcaactgga aggtggtgg gtaaaaaaat ggtccatgaa tatggctcgg   3180
tacagttcaa agcatggaaa tggaacccgc cgtctgctgc accatgggcg tgagcgggga   3240
gtacgcgact cctggacagc cgtaacaatg cggatggcct caacaagcca ggagcggcac   3300
gaacccagct cacgagcgca cagcgtgcca ggacggcggc cggcaaggat gaaatgtttt   3360
tcctaatata aatgcggact cctgacgcat tatatccatt ttgccactga ccaaagaca   3420 catatataca cgtgcgccgc cgtcctgcgc cacagccgcc tagcgctccg gccgcgcccg   3480
gttccctcgg cgtcatgcgc tggagccccc tcgcaccctg caccgcaaag cccatcaaca   3540
ccacactcgt ccccacaccg cgagtcaccg ccactgcact cgctgtccct caacccgtca   3600
caatctcgcc gacacgcgat aacgaaccca cgcaggtacg gcttccacaa ggagccgtct   3660
ggcggcaccg accccgaggg cagccgcaag gcgcgcctgc tgcagatctt tggccactgg   3720
aacgacaacg tggtggacct gatcaaggcc acgcccgagg aggacgtgct gcgccgcgac   3780
atctttgaca ggtacggaaa aagggagagc ggggtggctg gagggcggga aagggcgaag   3840
gggcggagaa agaaatgact aggggatggt gttcatttgt gggattgaga ggggtccgcg   3900
gatcccggca gagggcgcca gtggcaaggc gtgggagtcg cggggcggac aatgctgggc   3960
caggggcgcc tagtcacccc gggacactgt ctcagtatgc cgccgtcccg gccgcgccgc   4020
acaggccgcc catcttcacc tggagcaagg gccgcgtggc cctgctgggc gacagcgcgc   4080
acgccatgca gcccaacctg ggccagggcg gctgcatggc cattgaggac gcctacgagc   4140
tggccatcga cctcagccgc gccgtgtccg acaaggccgg aaacgcggcg gcggtggacg   4200
tggagggcgt gctgcgcagc taccaggaca gccgcatttt gccgtcagc gccattcacg   4260 gcatggcggt tgagagctgc aaccagcgta gtcgggctgg gctgctgtgg gcagggtcgg   4320
gttgggttgg gcgcacgtgg gcggcgagtg tatgtgcagt gtgacgtgca cactatcata   4380
atactttatg ctcaccgcac cgcgccgcgc cgcaccacgc gccacaggca tggctgcctt   4440 catgccagc acctacaagt gctacctggg cgagggctga agcaagtggg ttgagggggct   4500 gcgcatcccg caccccggcc gcgtggtggg gcggctggtg atgctgctca ccatgcccag   4560
cgtgctggag tgggtgctgg gcggcaacac cgaccacgtg gcgccgcacc gcaccagcta   4620
ctgctcgctg ggcgacaagc ccaaggtgag cggctgccgg gctggggggg ggtggaggga   4680
gaggaggagg attgcgggga gacgagggag ggcaaggcag gcgctgcctt cgtggatgca   4740
ccgccccgtc gttagcagga cctcaggaac tcgtccccaa aaccacaaca gaaccccaa   4800 tatcgcctct tccttcactg cttgtcacgc ctggtccgcc gaccgcaggc tttccccgag   4860
```

-continued

```
agccgcttcc ccgagttcat gaacaacgac gcctccatca tccgctcctc ccacgccgac      4920
tggctgctgg tggcggagcg cgacgccgcc acggccgccg ccgccaacgt gaacgccgcc      4980
accggcagca gcgccgccgc ggccgccgcc gccgacgtga acagcagctg ccagtgcaag      5040
ggcatctaca tggcggactc ggcggccctg gtgggccgct gcggcgccac ctcgcgcccc      5100
gcgctggccg tggacgacgt gcacgtcgcc gagagtcacg cgcaggtctg gcgcggcctc      5160
gccggcctcc ccccctcctc gtcgtccgcc tccaccgccg ccgcctctgc gtccgccgcc      5220
tcctctgccg ccagcggcac cgccagcacc ctgggcagct cggagggcta ctggctccgc      5280
gacctgggca gcgccgcgg cacctgggtc aacggcaagc gcctgcccga cggcgccacg      5340
gtgcagctgt ggcccggcga cgcggtggag ttcgccggc accccagcca cgaggtgttc      5400
aaggtgaaga tgcagcacgt gacgctgcgc agcgacgagc tcagcggcca ggcctacacc      5460
acgctcatgg tgggcaagat ccggaacaac gactacgtca tgcccgagtc gcggccggac      5520
ggcggcagcc agcagccggg ccgcctggtg acggcttaag cggcgccgtg cgtaagggcc      5580
ggcttacggg ggcggcagtg tcgctgtgga gggatggtct ggggtgggag aatgggagg      5640 agagcggcgg gagcccgagg agcggagcgc tggaggcttg cggagcggca gcttgggaag      5700
agctgcggag agaggaagga gcgcagggcg cttggagcac gcgccagatt acgatcacgg      5760
cagcgcgagg cgcgcgtctg acttcgaagt ggtaaggaag atttcatgta tgattgcgtc      5820
gagggacacc gcaagttta cgcgcggcgg agggagcctt ggggcataca acagtacgag      5880
cgggcgttgg tgagaaggtg gtcactccgt atgagaagat ggttactccg taccttcgtg      5940
agaagctgct gcgcacaagt tacgaaccta tctgtgtgga gagcccggta gtatatcagg      6000
ggcgagggtc atgaacgcga gtggcgagtc tgtgagcgcc aatttgttat gcggcataat      6060
ttcgcatcgg ggtattacgt ctacaaaatg ttgagctggc ttagcgcagg aggcaacacc      6120
tcaggcagaa tgtacgaatg tgtgcagaag ggcagagtca aggcagaggc ggagaagttg      6180
tcagggctgt gtgtggtttg gtcagggcgt ggctagatgg atatgagacc cgccgccgtc      6240
tccagattgt ggcggaggtg gaactctcgg cccccgcgcc agtccccgcg gccagcgcat      6300
cccgccatgc gggttgttgg ctggtgcatc gcgcggggtg tgctatgagt gtggaaacac      6360
tatgtcgcgt gtcgtgctga ggtctgttga gaggtttcgt cgtttgtgca tgtcctgtcc      6420
cggttggagt ttgagcgagg tggttcaaag ttttggatc gcgtgggaga gactgaaacg      6480
gtttggtgag aatggttgag acagaggttg ggcttggaaa ctggaggaga ggagcagcgt      6540
aactcgagga cgatgcagta gatgcaccac aacagttgtg gtgggcgcct ggagtaacac      6600
gcgtgccacc aacacgcaat tacagagatc cgtcatacag gagggatcat atgcgattta      6660
attttggttt tgcatttgta agacgttttc aca                                  6693
```

<210> SEQ ID NO 2
<211> LENGTH: 4903
<212> TYPE: DNA
<213> ORGANISM: Chlamydomonas reinhardtii

<400> SEQUENCE: 2

```
cagggtttgc ttttgggcac gacttgcatt gtgtacttgt ttgtgacctg aggtcgagga       60
ccttcttcta ggtagtcaaa acagaggaag accgatcctt agcatggccc tgaagatgcg      120
ggtgagccag cgccaggcgc tgggctcgca gaccttcgtc tgccccacg gtgcgtggca      180 tgaacagcgt tttatgtcga cttgggccgg agcgcagcgg actcaaccga ctcatctcgc      240
```

```
aggctcagtg gtgcgcaagg ccgtgagctc caaggcccgc gccgtgtcgc gccaggctca    300
ggtaaatgga tcatgcattc gcacatgcat ttgggcgacg tcactgcgac ttaccgggtc    360
gccttatcgc aggtcgttcg ggctcaggct gtgtcgaccc ccgttgagac caaggtcgcg    420
aacggggtgg ccgcatcctc tgctgcgggc actgggcaga acgacccggc tggcgacatc    480
agcaaggtat gctcgcgctg gcccatttga tgcttccgga ctcgtcgatg tgaccgtccc    540
gccatctcgt tgccgatgca gacggtgctg ggtattattc tgggtggtgg tgccggcacc    600
cgtctgtatc ctctgaccaa gaagcgtgcc aagccggcgg tgcccctggg cgccaactat    660
cgcctgatcg atattcccgt tagcaactgc ctgaacagca atgtcaccaa gatttactgc    720
ctcacccagt tcaactcggc gtcgctgaac cgccacctgt cccaggccta cgtgagtacc    780
ttgtgaatac tgaaactgcg ggctcgggct cgggcgacat agctgtcggc cgaccgcaga    840
atgcgtcgcc atgcggactc ggcgcaacac ctgtcgcgtg tcactcccgc tagggcacag    900
gagcgaacca gccctccagg cggcttaatc catcagggag actgtatgtt cagatggaag    960
ggacacaagg gcggggctgc gaaagctttc aagtacacac gtgtggcatc atatgctcta   1020
ccagcgcaca gcgccaccgc acaccgtacc gcgtccacat ccacctcttg ccatcccacc   1080
cctctcccat cctcccaccc tcccatcctc ccacctcccc atcaacccca tcaacccac   1140 cccaccaccc tccctctct ccgctccccc tctcgcacag aactcgtctg tgggcggcta   1200
caacagccgc ggcttcgtgg aggtgctggc ggccagccag tcgtccgcca acaagagctg   1260
gttccagggc accgccgacg ccgtgcgcca gtacatgtgg ctgttcgagg aggcggtgcg   1320
cgagggcgtg gaggacttcc tcatcctgtc gggtgagtgg gcaggaagag gggtggagag   1380
ggggaaagtt gggggtgggt gcacggaatg ggtgggaagg gggggtttcc tcctgcgcaa   1440
ggcagcgagg cgagaaggtt gaggccgccg taactggggg tggtggagtg ggcgggtgag   1500
gcgcatgttg aatggggcat ggaagactgg tgggtgggtg agtggagagg cgaagtttcg   1560
gagggtgccg gaaagggcat ggcggtgcag ggtgccactg gcacggtgg cctgccgtca   1620 agcgggcgtg ttgggcagcg ggactgcgcg ctgcagcagc cggcacagat acggagcgca   1680
cggcaggacg acacgcgggg cagccggcgg gctggtcggt cggtgtgctg ggggcagcag   1740
cgacgcgctg gtacacggag ggctacgagt gctgcacagc cagcctcggc acacaacagc   1800
caccagtacg gcatgtagca ccacgcgtct ggcttaccag tatcagcgca gtagcggacc   1860
aatgggggcg gcacggaacg cgtgtgtgcg gatgggctgc ggcaccgcca accggacgac   1920
tcccaaacat cacatcctcc ccctcctcc aggcgaccac ctgtaccgca tggactaccg   1980
cgactttgtc cgcaagcacc gcaactcggg cgccgccatc accatcgccg cgctgccctg   2040
cgcggagaag gaggccagcg ccttcggcct gatgaagatc gacgaggagg gccgcgtgat   2100
cgagttcgcg gagaagccca agggcgaggc gctgaccaag atgcgcgtgg acaccggcat   2160
cctgggcgtc gaccccgcca cgtgagtgtg tgcgcgctgg tgttggttga catggtggta   2220
tggtggtggt gtgtgggtgg gtgttgggtg gtgggtggga attggaggtg ctatcatggt   2280
gggtatgttg gggagttcgg aggatgcggt ctgtgggat atggttccag ggctaatggg   2340
tctgggatgg gtcaaggtgg aggggtgcgc ggtgtgcgtg tggcgtggag agcggcagtt   2400
gggtgcggca ccgcagcggc ggcaacgcag cagcataggc ggcgaggacg gcggcggcgc   2460
tccagcgggc agcgagccac ggcggcggca gctcagacca gcaccgccag ggcccagcag   2520
cgcagtgcag ccagcaacag cgctggtgct actgctggtg ctactgctgg gaatgcggct   2580
gttgtgggcg tcgagcagta gtgaccatca ccggcactgc gctgcggcag ccggcctgcc   2640
```

```
atccagcatg gcgccgcggg gctgggtgcg caagcgaaag gcagcagtgg tggacagagc    2700
tgttgaggca cggcgcctga ctgccggtg gtgacgatgt gcggatgctc gcgcccagca    2760
gaagggacca ggacccggct ggtggccgcc gccgccgccg cagcagcagt cgccacgtag    2820
cacgcagcgg ctacagcagc aaccggcgcc cacacccgca ccacaacccc agccaccgca    2880
ccagccaaac acacgcaccc ttccctctct ccccctctcc tcacacggcc cgcactgacc    2940
tgtccctccc cgtctccctc tgctccccct ccgccacctc agccgccgcc caagccta     3000 catcgcctcc atgggcatct acgtcatgtc cgccaaggcg ctgcgcgagc tgctgttgaa    3060
ccgcatgccg ggcgccaacg acttcggaaa cgaggtcatc cccggcgcca aggacgccgg    3120
cttcaaggtg caggccttcg cctttgacgg ctactgggag gacatcggta ccgtggaggc    3180
cttctacaac gccaacctgg cgctgaccga tcccgagaag gcgcagttct cgttctacga    3240
caaggacgcg ccgatctaca ccatgtcgcg cttcctgccg ccctccaagg tgatggactg    3300
cgacgtgaac atgtccatca tcggcgacgg ctgcgtgatc aaggccggct ccaagatcca    3360
caactccatc atcggcatcc gctcgctgat cggctccgac tgcatcatcg acagcgcgat    3420
gatgatgggc tcggactact acgagaccct ggaggagtgc gagtacgtgc ccggctgcct    3480
gcctatgggc gtgggcgatg gctccatcat ccgtcgcgcc attgtggaca gaacgcgcg     3540 cattggtccc aagtgccaga tcatcaacaa ggacggcgtc aaggaggcca accgcgagga    3600
ccagggcttc gtgatcaagg acggcattgt cgtcgtgatc aaggactcgc acatccccgc    3660
cggcaccatc atctaaacgt gatggctcgg gccgggaaga ggcggcgcgg cgcagagccg    3720
gccggcgcgg cggcagccgg cggcgcgcgg cgtgtggcgg agacgttggt gatggagagc    3780
agacggaggt ggcgggacct caggcacatt tcggcagctg ccgcagcgag gagcagggag    3840
agcgagcgtg tgtgggtgca cacgctagcg cgcactcacg acctgcagca gcagcagccg    3900
tggcggagat ggcgggagct gctcgggtac tgttgaagcg aggcgggccc ttggctgcgt    3960
ttttgggttg gaatgttgcg cagtgacggg actctataga gtagggggga ttgagtgtcc    4020
ttggttcggg tgaacgccat ggaccggtgc ggcacggcgt ggcgtggcac tgcgttgctg    4080
cggaagcgca agctgcggcc ttcccgcaac ggtgcagcag ccgcatcgga cgcaacaccc    4140
caggagcggc agtagctgcc agtcgcgtgc ggctgttttg agggagagcg cttttcggg    4200 agcgtgaacg gtcggaccaa gcaccggcgg tggcagcggc aggccttcgg ccccccggcc    4260
cttaaagctg ccggcgccaa ggcacgccgc gaggcgtgtg tgttcccgag gtgcagccgg    4320
gcggtggcgg ctgcagggtg ggtgcgagcc agctggcgtg ccatccagca cggcggcggt    4380
tgttgcggct cggcggtggg gaaggtggag cactgagcgg gcgtgggtcg ggacgcttcg    4440
cggctcacgc ggcggttggc cgttgcgcct gccttccgtg ggatgccgta ggaggggcgg    4500
gtccttactc gctcgcgtcc cacctggggg gttgtagttt cttaatttag cgtgtaccat    4560
gctcaacatt gtttgactcc cccagaccct gcgaacctgc atctgcggag gtagagaggg    4620
ctcttgggtg tgtgcagatt tttggttgtt tggtttgggt gatggtgcaa cagttttgcg    4680
cgtggcgagt gtgtgcgttc tcagatgagg agaattgttt gtgctatgca gagttgaggc    4740
gagaggaaga cttttgggca cgactgcacc gtgcatccat ggagcacagc tgcatagaag    4800
cacgtgggca acgcacggct tgcaccgtcc gatgcatcgt cccctccccc agagatttgg    4860
accgagagaa gaaatccagc acatgtaaac tcgtatgagg gca                     4903
```

<210> SEQ ID NO 3

```
<211> LENGTH: 42
<212> TYPE: DNA
<213> ORGANISM: Artificial Sequence
<220> FEATURE:
<223> OTHER INFORMATION: Chlamydomonas reinhardtii ZEP mutant 1-insert

<400> SEQUENCE: 3
gaaattaata agactcatta tattccggcg aacgcacctg ga                         42

<210> SEQ ID NO 4
<211> LENGTH: 6735
<212> TYPE: DNA
<213> ORGANISM: Artificial Sequence
<220> FEATURE:
<223> OTHER INFORMATION: Chlamydomonas reinhardtii ZEP mutant 1

<400> SEQUENCE: 4
gcgacgcacg gctgggccaa attcgccaac ggcaggagac caaatcgatc gaggcgatct      60
tgcgaagttc tcggacaaat cgatcgcacc catagtgatt taagcattac atttgcccaa    120
ggcgtgagaa gtgcgaggcc cgaacggcta tgacgccaat gcgcagctta cgacatttaa    180
agcaaattat tcatacatca tacagcacgc ttatgtgaag aaagccagga ttttaggctc    240
tcgccccgat caagacgatc tccccattgc gaagttctcg gtttctttcc ggttcgcctg    300
ctccgtatga tttacctttg cgctacaaca gcgacttaaa cgacctacgt cgccttactg    360
tgtgcgcgta cgtgtttgta gctgtgagat agttttgtcc gcagcgtacc cgcaaataga    420
atgctcgcga gcacttacac gccctgtggc gttcgccagg tggcaggccg cacggttgca    480
gtgcccagca gcttggtcgc gccagtggca gtcgctcggt cgctggggtt ggcgccctac    540
gtccctgtat gtgagccttc tgcggcgctt ccggcctgcc agcagcctag cgggcgtcgt    600
catgttcaga ctgctgccac tctccgtgcc gacaaccccca gctcggtcgc gcagctggtg    660
catcagaatg gaaaggggat gaaggttatt atcgccggcg cgggcatcgg cggcctggtg    720
ctagccgttg cacttctgaa gcagggcttc caggttcagg tctttgagcg cgacctgacg    780
gccatccgcg gcgagggcaa gtaccgtgga cccatcgaaa ttaataagac tcattatatt    840
ccggcgaacg cacctggaca ggtgcgttcg ccggaacacc aacgcgcttg tttttgctgt    900
gccgcgacca tgaactaggc cttatcttga ggtgttagca tgtttagcca gcgttggatc    960
tgtgtggcga ggtggggtg agaacccttc ctgtgtacct gctcgggcgt accttgtgcc   1020
ccaccgctga ctggcttact taatgacaaa acgcaggttc aaagcaatgc gctcgctgcg   1080
ctggaggcta tcgatcccga ggtggccgcg gaggtgctgc gcgagggctg catcactggc   1140
gaccgtatca acgggctctg cgacggcctg actggcgagt ggtgagtagg caatccagct   1200
gtgcatccag tcgcgcggtt gcggaggtcg tctcgggaaa cgcgacgtgg cgtccactcg   1260
cccaaggagt ggtctcccgc agcgtggtct cccgcagctc gggtgcaaca ccctgccccc   1320
tgccgcgagc gcgctgcgct tgcttatgtt gcgcagcggt gtgagttaca acagcttctg   1380
ttgaagagct gtcatacgaa gcacggcgcg ctgtggcgct gcagccgtgc tgtggaaact   1440
ccaacacctc caccgccagc ctgcgcacgc acacgcaata cactcgcctc gtgtgccccc   1500
tcctcacaca acggcatgtg acactcagtt ttaactctta ttttgacagc tgagagctac   1560
acgcttgggt gaatggggag gtccttgatg tttcgttgca ctccgtggct ccggagtccg   1620
tgcggaccgt cacccacaaa tgggagcgca cggctttctt gtgctgtctg ccccgttagc   1680
cactaactgc gaatgacctt gacagtttac tttgctattt ttccttccag gtacgtcaag   1740
ttcgacacgt tccacccggc ggtcagcaag ggcctgccgg tgacccgcgt catcagccgc   1800
```

```
ctcacgctgc agcagatcct ggccaaagcc gtggagcggt gagccgtgcg cgcggtgtga    1860
tggctttagc gtcagtgcta gcatgggggt tggtgggtgg taatcgcggc gcccatggcc    1920
gggtagcagc ggccgaaagc tggcgcagag cgcgcgttgg acaagcggtc ctgttgccgg    1980
tatgggcacg agcagggcgc tggtgcgggc aaagggcaga gtggagttgc agagcagcgc    2040
tggcgtcggc tgtgcgctct ccaaatggcc tcgtggcatt ctgacgggac acatcctgga    2100
aaatagtagc gcacccaact gctggtggct cctcgtacaa tcccccaat ttacaatcgc     2160 tcgttctggc tcgcagctac ggcggccccg gcaccatcca gaacggctgc aacgtgaccg    2220
agttcacgga gcgccgcaac gacaccaccg gcaacaacga ggtgagagcg tgctaagaag    2280
agcatgcacg tggagcgtgt aaaattgtgt ggcctgaagc ggcagtgcct gcggcatgga    2340
ctaggtggtt gcagcatgct gcgcgcgtgg gttgccggtc aggaaaccgc cggaccgagc    2400
cgcgcagatt cagtcaggag cggattagga agtttgaaaa acagggttcg gagtgtgcaa    2460
gcgggctcag gagctgtggt gcctttctac accggtcgcc ctaccaggca cccactgaaa    2520
ctgtaaaacc gttgctgcgc cggcgatgcc ctctacttca ctaggtgact gtgcagctgg    2580
aggacgggcg cacgttttgcg gccgacgtgc tggtgggcgc cgacggcatc tggtccaaga    2640
tccgtaagca gctcattggc gagaccaagg ccaactacag cgggtacacc tgctacaccg    2700
gtgagattat tgaccttcaa gttggaagga gggagcgggg ggagcggaat ggaaggaagc    2760
agcgtggacg gggcgcacgg aggggagggg actgcgggtc atagcgccgc cttgcggggc    2820
gtgaggagtg ttgggcggat attcagtttt ctttgcccaa gatcttccca caatccgcgt    2880
gtgtctgacg cgggatgtgg cccctgctgc catggcttcg caggcatctc ggactttacg    2940
ccggcggaca ttgacattgt gggctaccgc gtgttcctgg caacggcca gtactttgtc     3000 agcagcgacg tgggcaacgg caagatgcag tggtgagcgg cggcgggcgg gcgagcgagg    3060 gctgcgggt ctgagggtg tgtaccggc ggaaggagg ggaagggagg ggaagggaag        3120
gcaggatgca ggcgagggca ggatgtgatg gtgggaagag ggcgtggcga gcagcaactg    3180
gaaaggtggt gggtaaaaaa atggtccatg aatatggctc ggtacagttc aaagcatgga    3240
aatggaaccc gccgtctgct gcaccatggg cgtgagcggg gagtacgcga ctcctggaca    3300
gccgtaacaa tgcggatggc ctcaacaagc caggagcggc acgaacccag ctcacgagcg    3360
cacagcgtgc caggacggcg gccggcaagg atgaaatgtt tttcctaata taatgcggga   3420
ctcctgacgc attatatcca ttttgccact gagccaaaga cacatatata cacgtgcgcc    3480
gccgtcctgc gccacagccg cctagcgctc cggccgcgcc cggttccctc ggcgtcatgc    3540
gctggagccc cctcgcaccc tgcaccgcaa agcccatcaa caccacactc gtccccacac    3600
cgcgagtcac cgccactgca ctcgctgtcc ctcaacccgt cacaatctcg ccgacacgcg    3660
ataacgaacc cacgcaggta cggcttccac aaggagccgt ctggcggcac cgaccccgag    3720
ggcagccgca aggcgcgcct gctgcagatc tttggccact ggaacgacaa cgtggtggac    3780
ctgatcaagg ccacgcccga ggaggacgtg ctgcgccgcg acatctttga caggtacgga    3840
aaaaggagaa gcggggtggc tggagggcgg gaaaggggcga aggggcggag aaagaaatga   3900
ctaggggatg gtgttcattt gtgggattga gaggggtccg cggatcccgg cagagggcgc    3960
cagtggcaag gcgtgggagt cgcggggcgg acaatgctgg gccaggggcg cctagtcacc    4020
ccgggacact gtctcagtat gccgccgtcc cggccgcgcc gcacaggccg cccatcttca    4080
cctggagcaa gggccgcgtg gccctgctgg gcgacagcgc gcacgccatg cagcccaacc    4140
```

```
tgggccaggg cggctgcatg gccattgagg acgcctacga gctggccatc gacctcagcc    4200
gcgccgtgtc cgacaaggcc ggaaacgcgg cggcggtgga cgtggagggc gtgctgcgca    4260
gctaccagga cagccgcatt ttgcgcgtca gcgccattca cggcatggcg ggtgagagct    4320
gcaaccagcg tagtcgggct gggctgctgt gggcagggtc gggttgggtt gggcgcacgt    4380
gggcggcgag tgtatgtgca gtgtgacgtg cacactatca taatacttta tgctcaccgc    4440
accgcgccgc gccgcaccac gcgccacagg catggctgcc ttcatggcca gcacctacaa    4500
gtgctacctg ggcgagggct ggagcaagtg ggttgagggg ctgcgcatcc cgcaccccgg    4560
ccgcgtggtg gggcggctgg tgatgctgct caccatgccc agcgtgctgg agtgggtgct    4620
gggcggcaac accgaccacg tggcgccgca ccgcaccagc tactgctcgc tgggcgacaa    4680
gcccaaggtg agcggctgcc gggctggggg ggggtggagg gagaggagga ggattgcggg    4740
gagacgaggg agggcaaggc aggcgctgcc ttcgtggatg caccgccccg tcgttagcag    4800
gacctcagga actcgtcccc aaaaccacaa cagaaccccc aatatcgcct cttccttcac    4860
tgcttgtcac gcctggtccg ccgaccgcag gcttttcccg agagccgctt ccccgagttc    4920
atgaacaacg acgcctccat catccgctcc tcccacgccg actggctgct ggtggcggag    4980
cgcgacgccc ccacggccgc cgccgccaac gtgaacgccg ccaccggcag cagcgccgcc    5040
gcggccgccg ccgccgacgt gaacagcagc tgccagtgca agggcatcta catggcggac    5100
tcggcggccc tggtgggccg ctgcggcgcc acctcgcgcc ccgcgctggc cgtggacgac    5160
gtgcacgtcg ccgagagtca cgcgcaggtc tggcgcggcc tcgccggcct ccccccctcc    5220
tcgtcgtccg cctccaccgc cgccgcctct gcgtccgccg cctcctctgc cgccagcggc    5280
accgccagca ccctgggcag ctcggagggc tactggctcc gcgacctggg cagcggccgc    5340
ggcacctggg tcaacggcaa gcgcctgccc gacggcgcca cggtgcagct gtggcccggc    5400
gacgcggtgg agttcggccg gcaccccagc cacgaggtgt tcaaggtgaa gatgcagcac    5460
gtgacgctgc gcagcgacga gctcagcggc caggcctaca ccacgctcat ggtgggcaag    5520
atccggaaca acgactacgt catgcccgag tcgcggccgg acggcggcag ccagcagccg    5580
ggccgcctgg tgacggctta gcggcgccg tgcgtaaggg ccggcttacg ggggcggcag    5640
tgtcgctgtg gagggatggt ctggggtggg aggaatggga ggagagcggc gggagcccga    5700
ggagcggagc gctggaggct tgcggagcgg cagcttggga agagctgcgg agagaggaag    5760
gagcgcaggg cgcttggagc acgcgccaga ttacgatcac ggcagcgcga ggcgcgcgtc    5820
tgacttcgaa gtggtaagga agatttcatg tatgattgcg tcgagggaca ccgcaagttt    5880
tacgcgcggc ggagggagcc ttggggcata caacagtacg agcgggcgtt ggtgagaagg    5940
tggtcactcc gtatgagaag atggttactc cgtaccttcg tgagaagctg ctgcgcacaa    6000
gttacgaacc tatctgtgtg gagagcccgg tagtatatca ggggcgaggg tcatgaacgc    6060
gagtggcgag tctgtgagcg ccaatttgtt atgcggcata atttcgcatc ggggtattac    6120
gtctacaaaa tgttgagctg gcttagcgca ggaggcaaca cctcaggcag aatgtacgaa    6180
tgtgtgcaga agggcagagt caaggcagag gcggagaagt tgtcagggct gtgtgtggtt    6240
tggtcagggc gtggctagat ggatatgaga cccgccgccg tctccagatt gtggcggagg    6300
tggaactctc ggcccccgcg ccagtccccg cggccagcgc atcccgccat gcgggttgtt    6360
ggctggtgca tcgcgcgggg tgtgctatga gtgtggaaac actatgtcgc gtgtcgtgct    6420
gaggtctgtt gagaggtttc gtcgtttgtg catgtcctgt cccggttgga gtttgagcga    6480
ggtggttcaa agttttttgga tcgcgtggga gagactgaaa cggtttggtg agaatggttg    6540
```

```
agacagaggt tgggcttgga aactggagga gaggagcagc gtaactcgag gacgatgcag    6600
tagatgcacc acaacagttg tggtgggcgc ctggagtaac acgcgtgcca ccaacacgca    6660
attacagaga tccgtcatac aggagggatc atatgcgatt taattttggt tttgcatttg    6720
taagacgttt tcaca                                                     6735

<210> SEQ ID NO 5
<211> LENGTH: 44
<212> TYPE: DNA
<213> ORGANISM: Artificial Sequence
<220> FEATURE:
<223> OTHER INFORMATION: Chlamydomonas reinhardtii ZEP mutant 2-insert

<400> SEQUENCE: 5
tagctctaaa acatccaggt gcgttcgccg gactatagtg agta                      44

<210> SEQ ID NO 6
<211> LENGTH: 6737
<212> TYPE: DNA
<213> ORGANISM: Artificial Sequence
<220> FEATURE:
<223> OTHER INFORMATION: Chlamydomonas reinhardtii ZEP mutant 2

<400> SEQUENCE: 6
gcgacgcacg gctgggccaa attcgccaac ggcaggagac caaatcgatc gaggcgatct      60
tgcgaagttc tcggacaaat cgatcgcacc catagtgatt taagcattac atttgcccaa    120
ggcgtgagaa gtgcgaggcc cgaacggcta tgacgccaat gcgcagctta cgacatttaa    180
agcaaattat tcatacatca tacagcacgc ttatgtgaag aaagccagga ttttaggctc    240
tcgccccgat caagacgatc tccccattgc gaagttctcg gtttctttcc ggttcgcctg    300
ctccgtatga tttacctttg cgctacaaca gcgacttaaa cgacctacgt cgccttactg    360
tgtgcgcgta cgtgtttgta gctgtgagat agttttgtcc gcagcgtacc cgcaaatgaa    420
atgctcgcga gcacttacac gccctgtggc gttcgccagg tggcaggccg cacggttgca    480
gtgcccagca gcttggtcgc gccagtggca gtcgctcggt cgctgggggtt ggcgccctac    540 gtccctgtat gtgagccttc tgcggcgctt ccggcctgcc agcagcctag cgggcgtcgt    600
catgttcaga ctgctgccac tctccgtgcc gacaacccca gctcggtcgc gcagctggtg    660
catcagaatg gaaaggggat gaaggttatt atcgccggcg cgggcatcgg cggcctggtg    720
ctagccgttg cacttctgaa gcagggcttc caggttcagg tctttgagcg cgacctgacg    780
gccatccgcg gcgagggcaa gtaccgtgga cccatcagc tctaaaacat ccaggtgcgt    840
tcgccggact atagtgagta caggtgcgtt cgccggaaca ccaacgcgct tgtttttgct    900
gtgccgcgac catgaactag gccttatctt gaggtgttag catgtttagc cagcgttgga    960
tctgtgtggc gaggttgggg tgagaaccct tcctgtgtac ctgctcgggc gtaccttgtg   1020
ccccaccgct gactggctta cttaatgaca aaacgcaggt tcaaagcaat gcgctcgctg   1080
cgctggaggc tatcgatccc gaggtggccg cggaggtgct gcgcgagggc tgcatcactg   1140
gcgaccgtat caacgggctc tgcgacggcc tgactggcga gtggtgagta ggcaatccag   1200
ctgtgcatcc agtcgcgcgg ttgcggaggt cgtctcggga aacgcgacgt ggcgtccact   1260
cgcccaagga gtggtctccc gcagcgtggt ctcccgcagc tcgggtgcaa caccctgccc   1320
cctgccgcga gcgcgctgcg cttgcttatg ttgcgcagcg gtgtgagtta caacagcttc   1380
tgttgaagag ctgtcatacg aagcacggcg cgctgtggcg ctgcagccgt gctgtggaaa   1440
```

-continued

```
ctccaacacc tccaccgcca gcctgcgcac gcacacgcaa tacactcgcc tcgtgtgccc      1500
cctcctcaca caacggcatg tgacactcag ttttaactct tattttgaca gctgagagct      1560
acacgcttgg gtgaatgggg aggtccttga tgtttcgttg cactccgtgg ctccggagtc      1620
cgtgcggacc gtcacccaca aatgggagcg cacggctttc ttgtgctgtc tgccccgtta      1680
gccactaact gcgaatgacc ttgacagttt actttgctat ttttccttcc aggtacgtca      1740
agttcgacac gttccacccg gcggtcagca agggcctgcc ggtgacccgc gtcatcagcc      1800
gcctcacgct gcagcagatc ctggccaaag ccgtggagcg gtgagccgtg cgcgcggtgt      1860
gatggcttta gcgtcagtgc tagcatgggg gttggtgggt ggtaatcgcg gcgcccatgg      1920
ccgggtagca gcggccgaaa gctggcgcag agcgcgcgtt ggacaagcgg tcctgttgcc      1980
ggtatgggca cgagcagggc gctggtgcgg gcaaagggca gagtggagtt gcagagcagc      2040
gctggcgtcg gctgtgcgct ctccaaatgg cctcgtggca ttctgacggg acacatcctg      2100
gaaaatagta gcgcacccaa ctgctggtgg ctcctcgtac aatcccccca atttacaatc      2160
gctcgttctg gctcgcagct acggcggccc cggcaccatc cagaacggct gcaacgtgac      2220
cgagttcacg gagcgccgca acgacaccac cggcaacaac gaggtgagag cgtgctaaga      2280
agagcatgca cgtggagcgt gtaaaattgt gtggcctgaa gcggcagtgc ctgcggcatg      2340
gactaggtgg ttgcagcatg ctgcgcgcgt gggttgccgg tcaggaaacc gccggaccga      2400
gccgcgcaga ttcagtcagg agcggattag gaagtttgaa aaacagggtt cggagtgtgc      2460
aagcgggctc aggagctgtg gtgcctttct acaccggtcg ccctaccagg cacccactga      2520
aactgtaaaa ccgttgctgc gccggcgatg ccctctactt cactaggtga ctgtgcagct      2580
ggaggacggg cgcacgtttg cggccgacgt gctggtgggc gccgacggca tctggtccaa      2640
gatccgtaag cagctcattg gcgagaccaa ggccaactac agcgggtaca cctgctacac      2700
cggtgagatt attgaccttc aagttggaag gagggagcgg ggggagcgga atggaaggaa      2760
gcagcgtgga cggggcgcac ggaggggagg ggactgcggg tcatagcgcc gccttgcggg      2820
gcgtgaggag tgttgggcgg atattcagtt ttctttgccc aagatcttcc cacaatccgc      2880
gtgtgtctga cgcgggatgt ggcccctgct gccatggctt cgcaggcatc tcggacttta      2940
cgccggcgga cattgacatt gtgggctacc gcgtgttcct gggcaacggc cagtactttg      3000
tcagcagcga cgtgggcaac ggcaagatgc agtggtgagc ggcggcgggc gggcgagcga      3060
gggctgcggg gtctggaggg tgtgtaccgg gcggaaggga ggggaaggga ggggaaggga      3120
aggcaggatg caggcgaggg caggatgtga tggtgggaag agggcgtggc gagcagcaac      3180
tggaaaggtg gtgggtaaaa aaatggtcca tgaatatggc tcggtacagt tcaaagcatg      3240
gaaatggaac ccgccgtctg ctgcaccatg ggcgtgagcg gggagtacgc gactcctgga      3300
cagccgtaac aatgcggatg cctcaacaa gccaggagcg gcacgaaccc agctcacgag       3360
cgcacagcgt gccaggacgg cggccggcaa ggatgaaatg ttttcctaa tataaatgcg        3420 gactcctgac gcattatatc cattttgcca ctgagccaaa gacacatata tacacgtgcg      3480
ccgccgtcct gcgccacagc cgcctagcgc tccggccgcg cccggttccc tcggcgtcat      3540
gcgctggagc ccctcgcac cctgcaccgc aaagcccatc aacaccacac tcgtcccac        3600 accgcgagtc accgccactg cactcgctgt ccctcaaccc gtcacaatct cgccgacacg      3660
cgataacgaa cccacgcagg tacggcttcc acaaggagcc gtctggcggc accgaccccg      3720
agggcagcca caaggcgcgc ctgctgcaga tctttggcca ctggaacgac aacgtggtgg      3780
acctgatcaa ggccacgccc gaggaggacg tgctgcgccg cgacatcttt gacaggtacg      3840
```

```
gaaaaaggga gagcggggtg gctggagggc gggaaagggc gaaggggcgg agaaagaaat    3900
gactagggga tggtgttcat ttgtgggatt gagaggggtc cgcggatccc ggcagagggc    3960
gccagtggca aggcgtggga gtcgcggggc ggacaatgct gggccagggg cgcctagtca    4020
cccggggaca ctgtctcagt atgccgccgt cccggccgcg ccgcacaggc cgcccatctt    4080
cacctggagc aagggccgcg tggccctgct gggcgacagc gcgcacgcca tgcagcccaa    4140
cctgggccag ggcggctgca tggccattga ggacgcctac gagctggcca tcgacctcag    4200
ccgcgccgtg tccgacaagg ccggaaacgc ggcggcggtg gacgtggagg gcgtgctgcg    4260
cagctaccag gacagccgca ttttgcgcgt cagcgccatt cacggcatgg cgggtgagag    4320
ctgcaaccag cgtagtcggg ctgggctgct gtgggcaggg tcgggttggg ttgggcgcac    4380
gtgggcggcg agtgtatgtg cagtgtgacg tgcacactat cataatactt tatgctcacc    4440
gcaccgcgcc gcgccgcacc acgcgccaca ggcatggctg ccttcatggc cagcacctac    4500
aagtgctacc tgggcgaggg ctggagcaag tgggttgagg ggctgcgcat cccgcacccc    4560
ggccgcgtgg tggggcggct ggtgatgctg ctcaccatgc ccagcgtgct ggagtgggtg    4620
ctgggcggca acaccgacca cgtggcgccg caccgcacca gctactgctc gctgggcgac    4680
aagcccaagg tgagcggctg ccgggctggg gggggtgga gggagaggag gaggattgcg    4740
gggagacgag ggagggcaag gcaggcgctg ccttcgtgga tgcaccgccc cgtcgttagc    4800
aggacctcag gaactcgtcc ccaaaaccac aacagaaccc ccaatatcgc ctcttccttc    4860
actgcttgtc acgcctggtc cgccgaccgc aggctttccc cgagagccgc ttcccccgagt    4920 tcatgaacaa cgacgcctcc atcatccgct cctcccacgc cgactggctg ctggtggcgg    4980
agcgcgacgc cgccacggcc gccgccgcca acgtgaacgc cgccaccggc agcagcgccg    5040
ccgcggccgc cgccgccgac gtgaacagca gctgccagtg caagggcatc tacatggcgg    5100
actcggcggc cctggtgggc cgctgcgcg ccacctcgcg ccccgcgctg gccgtggacg    5160
acgtgcacgt cgccgagagt cacgcgcagg tctggcgcgg cctcgccggc ctcccccct    5220 cctcgtcgtc cgcctccacc gccgccgcct ctgcgtccgc cgcctcctct gccgccagcg    5280
gcaccgccag cacctgggc agctcggagg gctactggct ccgcgacctg ggcagcggcc    5340
gcggcacctg ggtcaacggc aagcgcctgc ccgacggcgc cacggtgcag ctgtggcccg    5400
gcgacgcggt ggagttcggc cggcaccca gccacgaggt gttcaaggtg aagatgcagc    5460
acgtgacgct gcgcagcgac gagctcagcg gccaggccta caccacgctc atggtgggca    5520
agatccggaa caacgactac gtcatgcccg agtcgcggcc ggacggcggc agccagcagc    5580
cgggccgcct ggtgacggct taagcggcgc cgtgcgtaag ggccggctta cggggcggc    5640 agtgtcgctg tggagggatg gtctgggtg gaggaatgg gaggagagcg gcgggagccc    5700
gaggagcgga gcgctggagg cttgcggagc ggcagcttgg gaagagctgc ggagagagga    5760
aggagcgcag ggcgcttgga gcacgcgcca gattacgatc acggcagcgc gaggcgcgcg    5820
tctgacttcg aagtggtaag gaagatttca tgtatgattg cgtcgaggga caccgcaagt    5880
tttacgcgcg gcgagggag ccttgggca tacaacagta cgagcgggcg ttggtgagaa    5940
ggtggtcact ccgtatgaga agatggttac tccgtaccttt cgtgagaagc tgctgcgcac    6000
aagttacgaa cctatctgtg tggagagccc ggtagtatat caggggcgag ggtcatgaac    6060
gcgagtggcg agtctgtgag cgccaatttg ttatgcggca taatttcgca tcggggtatt    6120
acgtctacaa aatgttgagc tggcttagcg caggaggcaa caccctcaggc agaatgtacg    6180
```

-continued

| | |
|---|---|
| aatgtgtgca gaagggcaga gtcaaggcag aggcggagaa gttgtcaggg ctgtgtgtgg | 6240 |
| tttggtcagg gcgtggctag atggatatga gacccgccgc cgtctccaga ttgtggcgga | 6300 |
| ggtggaactc tcggcccccg cgccagtccc cgcggccagc gcatcccgcc atgcgggttg | 6360 |
| ttggctggtg catcgcgcgg ggtgtgctat gagtgtggaa acactatgtc gcgtgtcgtg | 6420 |
| ctgaggtctg ttgagaggtt tcgtcgtttg tgcatgtcct gtcccggttg gagtttgagc | 6480 |
| gaggtggttc aaagtttttg gatcgcgtgg gagagactga aacggtttgg tgagaatggt | 6540 |
| tgagacagag gttgggcttg gaaactggag gagaggagca gcgtaactcg aggacgatgc | 6600 |
| agtagatgca ccacaacagt tgtggtgggc gcctggagta acacgcgtgc caccaacacg | 6660 |
| caattacaga gatccgtcat acaggaggga tcatatgcga tttaattttg gttttgcatt | 6720 |
| tgtaagacgt tttcaca | 6737 |

<210> SEQ ID NO 7
<211> LENGTH: 6694
<212> TYPE: DNA
<213> ORGANISM: Artificial Sequence
<220> FEATURE:
<223> OTHER INFORMATION: Chlamydomonas reinhardtii ZEP mutant 3

<400> SEQUENCE: 7

| | |
|---|---|
| gcgacgcacg gctgggccaa attcgccaac ggcaggagac caaatcgatc gaggcgatct | 60 |
| tgcgaagttc tcggacaaat cgatcgcacc catagtgatt taagcattac atttgcccaa | 120 |
| ggcgtgagaa gtgcgaggcc cgaacggcta tgacgccaat gcgcagctta cgacatttaa | 180 |
| agcaaattat tcatacatca tacagcacgc ttatgtgaag aaagccagga ttttaggctc | 240 |
| tcgccccgat caagacgatc tccccattgc gaagttctcg gtttctttcc ggttcgcctg | 300 |
| ctccgtatga tttacctttg cgctacaaca gcgacttaaa cgacctacgt cgccttactg | 360 |
| tgtgcgcgta cgtgtttgta gctgtgagat agttttgtcc gcagcgtacc cgcaaataga | 420 |
| atgctcgcga gcacttacac gccctgtggc gttcgccagg tggcaggccg cacgttgca | 480 |
| gtgcccagca gcttggtcgc gccagtggca gtcgctcggt cgctggggtt ggcgccctac | 540 |
| gtccctgtat gtgagccttc tcggcgcgtt ccggcctgcc agcagcctag cgggcgtcgt | 600 |
| catgttcaga ctgctgccac tctccgtgcc gacaaccccca gctcggtcgc gcagctggtg | 660 |
| catcagaatg gaaaggggat gaaggttatt atcgccggcg cgggcatcgg cggcctggtg | 720 |
| ctagccgttg cacttctgaa gcagggcttc caggttcagg tctttgagcg cgacctgacg | 780 |
| gccatccgcg gcgagggcaa gtaccgtgga cccatcacag gtgcgttcgc cggaacacca | 840 |
| acgcgcttgt ttttgctgtg ccgcgaccat gaactaggcc ttatcttgag gtgttagcat | 900 |
| gtttagccag cgttggatct gtgtggcgag gttggggtga gaacccttcc tgtgtacctg | 960 |
| ctcgggcgta ccttgtgccc caccgctgac tggcttactt aatgacaaaa cgcaggttca | 1020 |
| aagcaatgcg ctcgctgcgc tggaggctat cgatcccgag gtggccgcgg aggtgctgcg | 1080 |
| cgagggctgc atcactggcg accgtatcaa cgggctctgc gacggcctga ctggcgagtg | 1140 |
| gtgagtaggc aatccagctg tgcatccagt cgcgcggttg cggaggtcgt ctcgggaaac | 1200 |
| gcgacgtggc gtccactcgc ccaaggagtg gtctcccgca gcgtggtctc ccgcagctcg | 1260 |
| ggtgcaacac cctgccccct gccgcgagcg cgctgcgctt gcttatgttg cgcagcggtg | 1320 |
| tgagttacaa cagcttctgt tgaagagctg tcatacgaag cacggcgcgc tgtggcgctg | 1380 |
| cagccgtgct gtggaaactc caacacctcc accgccagcc tgcgcacgca cacgcaatac | 1440 |
| actcgcctcg tgtgcccccct cctcacacaa cggcatgtga cactcagttt taactcttat | 1500 |

```
tttgacagct gagagctaca cgcttgggtg aatggggagg tccttgatgt ttcgttgcac   1560
tccgtggctc cggagtccgt gcggaccgtc acccacaaat gggagcgcac ggctttcttg   1620
tgctgtctgc cccgttagcc actaactgcg aatgaccttg acagtttact ttgctatttt   1680
tccttccagg tacgtcaagt tcgacacgtt ccacccggcg gtcagcaagg gcctgccggt   1740
gacccgcgtc atcagccgcc tcacgctgca gcagatcctg gccaaagccg tggagcggtg   1800
agccgtgcgc gcggtgtgat ggctttagcg tcagtgctag catgggggtt ggtgggtggt   1860
aatcgcggcg cccatggccg ggtagcagcg gccgaaagct ggcgcagagc gcgcgttgga   1920
caagcggtcc tgttgccggt atgggcacga gcagggcgct ggtgcgggca aagggcagag   1980
tggagttgca gagcagcgct ggcgtcggct gtgcgctctc caaatggcct cgtggcattc   2040
tgacgggaca catcctggaa aatagtagcg cacccaactg ctggtggctc ctcgtacaat   2100 cccccccaatt tacaatcgct cgttctggct cgcagctacg gcggccccgg caccatccag   2160
aacggctgca acgtgaccga gttcacggag cgccgcaacg acaccaccgg caacaacgag   2220
gtgagagcgt gctaagaaga gcatgcacgt ggagcgtgta aaattgtgtg gcctgaagcg   2280
gcagtgcctg cggcatggac taggtggttg cagcatgctg cgcgcgtggg ttgccggtca   2340
ggaaaccgcc ggaccgagcc gcgcagattc agtcaggagc ggattaggaa gtttgaaaaa   2400
cagggttcgg agtgtgcaag cgggctcagg agctgtggtg cctttctaca ccggtcgccc   2460
taccaggcac ccactgaaac tgtaaaaccg ttgctgcgcc ggcgatgccc tctacttcac   2520
taggtgactg tgcagctgga ggacgggcgc acgtttgcgg ccgacgtgct ggtgggcgcc   2580
gacggcatct ggtccaagat ccgtaagcag ctcattggcg agaccaaggc caactacagc   2640
gggtacacct gctacaccgg tgagattatt gaccttcaag ttggaaggag ggagcggggg   2700
gagcggaatg gaaggaagca gcgtggacgg ggcgcacgga ggggagggga ctgcgggtca   2760
tagcgccgcc ttgcggggcg tgaggagtgt tgggcggata ttcagttttc tttgcccaag   2820
atcttcccac aatccgcgtg tgtctgacgc gggatgtggc ccctgctgcc atggcttcgc   2880
aggcatctcg gactttacgc cggcggacat tgacattgtg ggctaccgcg tgttcctggg   2940
caacggccag tactttgtca gcagcgacgt gggcaacggc aagatgcagt ggtgagcggc   3000
ggcgggcggg cgagcgaggg ctgcggggtc tggagggtgt gtaccgggcg aagggaggg   3060 gaagggaggg gaagggaagg caggatgcag gcgagggcag gatgtgatgg tgggaagagg   3120
gcgtggcgag cagcaactgg aaaggtggtg ggtaaaaaaa tggtccatga atatggctcg   3180
gtacagttca aagcatggaa atggaacccg ccgtctgctg caccatgggc gtgagcgggg   3240
agtacgcgac tcctggacag ccgtaacaat gcggatggcc tcaacaagcc aggagcggca   3300
cgaacccagc tcacgagcgc acagcgtgcc aggacggcgg ccggcaagga tgaaatgttt   3360
ttcctaatat aaatgcggac tcctgacgca ttatatccat tttgccactg agccaaagac   3420
acatatatac acgtgcgccg ccgtcctgcg ccacagccgc ctagcgctcc ggccgcgccc   3480
ggttccctcg gcgtcatgcg ctggagcccc ctcgcaccct gcaccgcaaa gcccatcaac   3540
accacactcg tccccacacc gcgagtcacc gccactgcac tcgctgtccc tcaacccgtc   3600
acaatctcgc cgacacgcga taacgaaccc acgcaggtac ggcttccaca aggagccgtc   3660
tggcggcacc gaccccgagg gcagccgcaa ggcgcgcctg ctgcagatct ttggccactg   3720
gaacgacaac gtggtggacc tgatcaaggc cacgcccgag gaggacgtgc tgcgccgcga   3780
catctttgac aggtacggaa aaagggagag cggggtggct ggagggcggg aaagggcgaa   3840
```

```
ggggcggaga aagaaatgac tagggatgg tgttcatttg tgggattgag aggggtccgc    3900
ggatcccggc agagggcgcc agtggcaagg cgtgggagtc gcggggcgga caatgctggg    3960 ccagggcgc ctagtcaccc cgggacactg tctcagtatg ccgccgtccc ggccgcgccg    4020
cacaggccgc ccatcttcac ctggagcaag gccgcgtgg ccctgctggg cgacagcgcg    4080
cacgccatgc agcccaacct gggccagggc ggctgcatgg ccattgagga cgcctacgag    4140
ctggccatcg acctcagccg cgccgtgtcc gacaaggccg gaaacgcggc ggcggtggac    4200
gtggagggcg tgctgcgcag ctaccaggac agccgcattt gcgcgtcag cgccattcac    4260 ggcatggcgg gtgagagctg caaccagcgt agtcgggctg ggctgctgtg ggcagggtcg    4320
ggttgggttg ggcgcacgtg ggcggcgagt gtatgtgcag tgtgacgtgc acactatcat    4380
aatactttat gctcaccgca ccgcgccgcg ccgcaccacg cgccacaggc atggctgcct    4440
tcatggccag cacctacaag tgctacctgg gcagggctg gagcaagtgg gttgagggc    4500 tgcgcatccc gcaccccggc cgcgtggtgg ggcggctggt gatgctgctc accatgccca    4560
gcgtgctgga gtgggtgctg ggcggcaaca ccgaccacgt ggcgccgcac cgcaccagct    4620
actgctcgct gggcgacaag cccaaggtga gcggctgccg ggctggggg ggtgtgaggg    4680 agaggaggag gattgcgggg agacgaggga gggcaaggca ggcgctgcct tcgtggatgc    4740
accgccccgt cgttagcagg acctcaggaa ctcgtcccca aaaccacaac agaaccccca    4800
atatcgcctc ttccttcact gcttgtcacg cctggtccgc cgaccgcagg cttccccga    4860 gagccgcttc cccgagttca tgaacaacga cgcctccatc atccgctcct cccacgccga    4920
ctggctgctg gtggcggagc gcgacgccgc cacggccgcc gccgcaacg tgaacgccgc    4980 caccggcagc agcgccgccg cggccgccgc cgccgacgtg aacagcagct gccagtgcaa    5040
gggcatctac atggcggact cggcggccct ggtgggccgc tgcggcgcca cctcgcgccc    5100
cgcgctggcc gtggacgacg tgcacgtcgc cgagagtcac gcgcaggtct ggcgcggcct    5160
cgccggcctc ccccccctcct cgtcgtccgc ctccaccgcc gccgcctctg cgtccgccgc    5220
ctcctctgcc gccagcggca ccgccagcac cctgggcagc tcggagggct actggctccg    5280
cgacctgggc agcggccgcg cacctgggt caacggcaag cgcctgcccg acggcgccac    5340
ggtgcagctg tggcccggcg acgcggtgga gttcggccgg caccccagcc acgaggtgtt    5400
caaggtgaag atgcagcacg tgacgctgcg cagcgacgag ctcagcggcc aggcctacac    5460
cacgctcatg gtgggcaaga tccggaacaa cgactacgtc atgcccgagt cgcggccgga    5520
cggcggcagc agcagccgg gccgcctggt gacggcttaa gcggcgccgt gcgtaagggc    5580
cggcttacgg gggcggcagt gtcgctgtgg agggatggtc tggggtggga ggaatgggag    5640
gagagcggcg ggagcccgag gagcggagcg ctggaggctt gcggagcggc agcttgggaa    5700
gagctgcgga gagaggaagg agcgcagggc gcttggagca cgcgccagat tacgatcacg    5760
gcagcgcgag gcgcgcgtct gacttcgaag tggtaaggaa gatttcatgt atgattgcgt    5820
cgagggacac cgcaagtttt acgcgcggcg gagggagcct tggggcatac aacagtacga    5880
gcgggcgttg gtgagaaggt ggtcactccg tatgagaaga tggttactcc gtaccttcgt    5940
gagaagctgc tgcgcacaag ttacgaacct atctgtgtgg agagcccggt agtatatcag    6000
gggcgagggt catgaacgcg agtggcgagt ctgtgagcgc caatttgtta tgcggcataa    6060
tttcgcatcg gggtattacg tctacaaaat gttgagctgg cttagcgcag gaggcaacac    6120
ctcaggcaga atgtacgaat gtgtgcagaa gggcagagtc aaggcagagg cggagaagtt    6180
gtcagggctg tgtgtggttt ggtcagggcg tggctagatg gatatgagac ccgccgccgt    6240
```

```
ctccagattg tggcggaggt ggaactctcg gccccgcgc cagtcccgc ggccagcgca    6300 tcccgccatg cgggttgttg gctggtgcat cgcgcgggg gtgctatgag tgtggaaaca    6360
ctatgtcgcg tgtcgtgctg aggtctgttg agaggtttcg tcgtttgtgc atgtcctgtc    6420
ccggttggag tttgagcgag gtggttcaaa gttttggat cgcgtgggag agactgaaac    6480
ggtttggtga aatggttga cagagggtt gggcttggaa actggaggag aggagcagcg    6540
taactcgagg acgatgcagt agatgcacca caacagttgt ggtgggcgcc tggagtaaca    6600
cgcgtgccac caacacgcaa ttacagagat ccgtcataca ggagggatca tatgcgattt    6660
aattttggtt ttgcatttgt aagacgtttt caca                               6694
```

<210> SEQ ID NO 8
<211> LENGTH: 4904
<212> TYPE: DNA
<213> ORGANISM: Artificial Sequence
<220> FEATURE:
<223> OTHER INFORMATION: Chlamydomonas reinhardtii AGP mutant 1

<400> SEQUENCE: 8

```
cagggtttgc ttttgggcac gacttgcatt gtgtacttgt ttgtgacctg aggtcgagga     60
ccttcttcta ggtagtcaaa acagaggaag accgatcctt agcatggccc tgaagaatgc    120
gggtgagcca cgccaggcg ctgggctcgc agaccttcgt ctgccccac ggtgcgtggc     180 atgaacagcg ttttatgtcg acttgggccg gagcgcagcg gactcaaccg actcatctcg    240
caggctcagt ggtgcgcaag gccgtgagct ccaaggcccg cgccgtgtcg cgccaggctc    300
aggtaaatgg atcatgcatt cgcacatgca tttgggcgac gtcactgcga cttaccgggt    360
cgccttatcg caggtcgttc gggctcaggc tgtgtcgacc cccgttgaga ccaaggtcgc    420
gaacggggtg gccgcatcct ctgctgcggg cactgggcag aacgacccgg ctggcgacat    480
cagcaaggta tgctcgcgct ggcccatttg atgcttccgg actcgtcgat gtgaccgtcc    540
cgccatctcg ttgccgatgc agacggtgct gggtattatt ctgggtggtg gtgccggcac    600
ccgtctgtat cctctgacca agaagcgtgc caagccggcg gtgcccctgg cgccaacta    660 tcgcctgatc gatattcccg ttagcaactg cctgaacagc aatgtcacca agatttactg    720
cctcacccag ttcaactcgg cgtcgctgaa ccgccacctg tcccaggcct acgtgagtac    780
cttgtgaata ctgaaactgc gggctcgggc tcgggcgaca tagctgtcgg ccgaccgcag    840
aatgcgtcgc catgcggact cggcgcaaca cctgtcgcgt gtcactcccg ctagggcaca    900
ggagcgaacc agccctccag gcggcttaat ccatcaggga gactgtatgt tcagatggaa    960
gggacacaag ggcggggctg cgaaagcttt caagtacaca cgtgtggcat catatgctct   1020
accagcgcac agcgccaccg cacaccgtac cgcgtccaca tccacctctt gccatcccac   1080
ccctctccca tcctcccacc ctcccatcct cccaccctcc catcaacccc atcaaccca    1140 ccccaccacc ctcccctctc tccgctcccc ctctcgcaca gaactcgtct gtgggcggct   1200
acaacagccg cggcttcgtg gaggtgctgg cggccagcca gtcgtccgcc aacaagagct   1260
ggttccaggg caccgccgac gccgtgcgcc agtacatgtg gctgttcgag gaggcggtgc   1320
gcgagggcgt ggaggacttc ctcatcctgt cgggtgagtg gcaggaagga ggggtggaga   1380 ggggaaagt tggggtgggg tgcacggaat gggtgggaag gggggtttc ctcctgcgca    1440 aggcagcgag gcgagaaggt tgaggccgcc gtaactgggg gtggtggagt gggcgggtga   1500
ggcgcatgtt gaatggggca tggaagactg gtgggtgggt gagtggagag gcgaagtttc   1560
```

```
ggagggtgcc ggaaagggca tggcggtgca gggtgccact gggcacggtg gcctgccgtc    1620
aagcgggcgt gttgggcagc gggactgcgc gctgcagcag ccggcacaga tacgagcgc     1680 acggcaggac gacacgcggg gcagccggcg ggctggtcgg tcggtgtgct gggggcagca    1740
gcgacgcgct ggtacacgga gggctacgag tgctgcacag ccagcctcgg cacacaacag    1800
ccaccagtac ggcatgtagc accacgcgtc tggcttacca gtatcagcgc agtagcggac    1860
caatgggggc ggcacggaac gcgtgtgtgc ggatgggctg cggcaccgcc aaccggacga    1920
ctcccaaaca tcacatcctc cccctcctc caggcgacca cctgtaccgc atggactacc     1980
gcgactttgt ccgcaagcac cgcaactcgg gcgccgccat caccatcgcc gcgctgccct    2040
gcgcggagaa ggaggccagc gccttcggcc tgatgaagat cgacgaggag ggccgcgtga    2100
tcgagttcgc ggagaagccc aagggcgagg cgctgaccaa gatgcgcgtg acaccggca    2160 tcctgggcgt cgaccccgcc acgtgagtgt gtgcgcgctg gtgttggttg acatggtggt    2220
atggtggtgg tgtgtgggtg ggtgttgggt ggtgggtggg aattggaggt gctatcatgg    2280
tgggtatgtt ggggagttcg gaggatgcgg tctgtgggga tatggttcca gggctaatgg    2340
gtctgggatg ggtcaaggtg gaggggtgcg cggtgtgcgt gtggcgtgga gagcggcagt    2400
tgggtgcggc accgcagcgg cggcaacgca gcagcatagg cggcgaggac ggcggcggcg    2460
ctccagcggg cagcgagcca cggcggcggc agctcagacc agcaccgcca gggcccagca    2520
gcgcagtgca gccagcaaca gcgctggtgc tactgctggt gctactgctg ggaatgcggc    2580
tgttgtgggc gtcgagcagt agtgaccatc accggcactg cgctgcggca gccggcctgc    2640
catccagcat ggcgccgcgg ggctgggtgc gcaagcgaaa ggcagcagtg gtggacagag    2700
ctgttgaggc acggcgcctg actgcccggt ggtgacgatg tgcggatgct cgcgcccagc    2760
agaagggacc aggacccggc tggtggccgc cgccgccgcc gcagcagcag tcgccacgta    2820
gcacgcagcg gctacagcag caaccggcgc ccacacccgc accacaaccc cagccaccgc    2880
accagccaaa cacacgcacc cttccctctc tcccccctctc ctcacacggc ccgcactgac    2940
ctgtccctcc ccgtctccct ctgctccccc tccgccacct cagcgccgcc gccaagccct    3000
acatcgcctc catgggcatc tacgtcatgt ccgccaaggc gctgcgcgag ctgctgttga    3060
accgcatgcc gggcgccaac gacttcggaa acgaggtcat ccccggcgcc aaggacgccg    3120
gcttcaaggt gcaggccttc gcctttgacg gctactggga ggacatcggt accgtggagg    3180
ccttctacaa cgccaacctg gcgctgaccg atcccgagaa ggcgcagttc tcgttctacg    3240
acaaggacgc gccgatctac accatgtcgc gcttcctgcc gccctccaag gtgatggact    3300
gcgacgtgaa catgtccatc atcggcgacg gctgcgtgat caaggccggc tccaagatcc    3360
acaactccat catcggcatc cgctcgctga tcggctccga ctgcatcatc gacagcgcga    3420
tgatgatggg ctcggactac tacgagaccc tggaggagtg cgagtacgtg cccggctgcc    3480
tgcctatggg cgtgggcgat ggctccatca tccgtcgcgc cattgtggac aagaacgcgc    3540
gcattggtcc caagtgccag atcatcaaca aggacgcgt caaggaggcc aaccgcgagg    3600
accagggctt cgtgatcaag gacggcattg tcgtcgtgat caaggactcg cacatccccg    3660
ccggcaccat catctaaacg tgatggctcg gccggaag aggcggcgcg gcgcagagcc       3720
ggccggcgcg gcggcagccg gcggcgcgcg gcgtgtggcg gagacgttgg tgatggagag    3780
cagacggagg tggcgggacc tcaggcacat ttcggcagct gccgcagcga ggagcaggga    3840
gagcgagcgt gtgtgggtgc acacgctagc gcgcactcac gacctgcagc agcagcagcc    3900
gtggcggaga tggcgggagc tgctcgggta ctgttgaagc gaggcgggcc cttggctgcg    3960
```

```
tttttgggtt ggaatgttgc gcagtgacgg gactctatag agtagggggg attgagtgtc    4020
cttggttcgg gtgaacgcca tggaccggtg cggcacggcg tggcgtggca ctgcgttgct    4080
gcggaagcgc aagctgcggc cttcccgcaa cggtgcagca ccgcatcgg acgcaacacc     4140 ccaggagcgg cagtagctgc cagtcgcgtg cggctgtttt gagggagagc gcttttt cgg   4200 gagcgtgaac ggtcggacca agcaccggcg gtggcagcgg caggccttcg gccccccggc   4260
ccttaaagct gccggcgcca aggcacgccg cgaggcgtgt gtgttcccga ggtgcagccg   4320
ggcggtggcg gctgcagggt gggtgcgagc cagctggcgt gccatccagc acggcggcgg   4380
ttgttgcggc tcggcggtgg ggaaggtgga gcactgagcg ggcgtgggtc gggacgcttc    4440
gcggctcacg cggcggttgg ccgttgcggc tgccttccgt gggatgccgt aggaggggcg    4500
ggtccttact cgctcgcgtc ccacctgggg ggttgtagtt tcttaattta gcgtgtacca    4560
tgctcaacat tgtttgactc ccccagaccc tgcgaacctg catctgcgga ggtagagagg    4620
gctcttgggt gtgtgcagat ttttggttgt ttggtttggg tgatggtgca acagttttgc   4680
gcgtggcgag tgtgtgcgtt ctcagatgag gagaattgtt tgtgctatgc agagttgagg   4740
cgagaggaag acttttgggc acgactgcac cgtgcatcca tggagcacag ctgcatagaa   4800
gcacgtgggc aacgcacggc ttgcaccgtc cgatgcatcg tccccctccc cagagatttg   4860
gaccgagaga agaaatccag cacatgtaaa ctcgtatgag ggca                     4904
```

<210> SEQ ID NO 9
<211> LENGTH: 4902
<212> TYPE: DNA
<213> ORGANISM: Artificial Sequence
<220> FEATURE:
<223> OTHER INFORMATION: Chlamydomonas reinhardtii AGP mutant 2

<400> SEQUENCE: 9

```
cagggtttgc ttttgggcac gacttgcatt gtgtacttgt ttgtgacctg aggtcgagga     60
ccttcttcta ggtagtcaaa acagaggaag accgatcctt agcatggccc tgaattgcgg    120
gtgagccagc gccaggcgct gggctcgcag accttcgtct gccccacgg tgcgtggcat     180 gaacagcgtt ttatgtcgac ttgggccgga gcgcagcgga ctcaaccgac tcatctcgca    240
ggctcagtgg tgcgcaaggc cgtgagctcc aaggcccgcg ccgtgtcgcg ccaggctcag   300
gtaaatggat catgcattcg cacatgcatt tgggcgacgt cactgcgact taccgggtcg    360
ccttatcgca ggtcgttcgg gctcaggctg tgtcgacccc cgttgagacc aaggtcgcga    420
acggggtggc gcatcctct gctgcgggca ctgggcagaa cgaccccggct ggcgacatca    480 gcaaggtatg ctcgcgctgg cccatttgat gcttccggac tcgtcgatgt gaccgtcccg    540
ccatctcgtt gccgatgcag acggtgctgg gtattattct gggtggtggt gccggcaccc    600
gtctgtatcc tctgaccaag aagcgtgcca agccggcggt gcccctgggc gccaactatc    660
gcctgatcga tattcccgtt agcaactgcc tgaacagcaa tgtcaccaag atttactgcc    720
tcacccagtt caactcggcg tcgctgaacc gccacctgtc ccaggcctac gtgagtacct    780
tgtgaatact gaaactgcgg gctcgggctc gggcgacata gctgtcggcc gaccgcagaa    840
tgcgtcgcca tgcggactcg gcgcaacacc tgtcgcgtgt cactcccgct agggcacagg    900
agcgaaccag ccctccaggc ggcttaatcc atcagggaga ctgtatgttc agatggaagg    960
gacacaaggg cggggctgcg aaagctttca agtacacacg tgtggcatca tatgctctac   1020
cagcgcacag cgccaccgca caccgtaccg cgtccacatc cacctcttgc catcccaccc   1080
```

```
ctctcccatc ctcccaccct cccatcctcc caccctccca tcaaccccat caaccccacc    1140
ccaccaccct cccctctctc cgctcccct  ctcgcacaga actcgtctgt gggcggctac    1200
aacagccgcg gcttcgtgga ggtgctggcg gccagccagt cgtccgccaa caagagctgg    1260
ttccagggca ccgccgacgc cgtgcgccag tacatgtggc tgttcgagga ggcggtgcgc    1320
gagggcgtgg aggacttcct catcctgtcg ggtgagtggg caggaagagg ggtggagagg    1380
gggaaagttg ggggtgggtg cacggaatgg gtgggaaggg ggggtttcct cctgcgcaag    1440
gcagcgaggc gagaaggttg aggccgccgt aactgggggt ggtggagtgg gcgggtgagg    1500
cgcatgttga atggggcatg gaagactggt gggtgggtga gtggagaggc gaagtttcgg    1560
agggtgccgg aaagggcatg gcggtgcagg gtgccactgg gcacggtggc ctgccgtcaa    1620
gcgggcgtgt tgggcagcgg gactgcgcgc tgcagcagcc ggcacagata cggagcgcac    1680
ggcaggacga cacgcggggc agccggcggg ctggtcggtc ggtgtgctgg gggcagcagc    1740
gacgcgctgg tacacggagg gctacgagtg ctgcacagcc agcctcggca cacaacagcc    1800
accagtacgg catgtagcac cacgcgtctg gcttaccagt atcagcgcag tagcggacca    1860 atggggggcgg cacggaacgc gtgtgtgcgg atgggctgcg gcaccgccaa ccggacgact    1920
cccaaacatc acatcctccc ccctcctcca ggcgaccacc tgtaccgcat ggactaccgc    1980
gactttgtcc gcaagcaccg caactcgggc gccgccatca ccatcgccgc gctgccctgc    2040
gcggagaagg aggccagcgc cttcggcctg atgaagatcg acgaggaggg ccgcgtgatc    2100
gagttcgcgg agaagcccaa gggcgaggcg ctgaccaaga tgcgcgtgga caccggcatc    2160
ctgggcgtcg accccgccac gtgagtgtgt gcgcgctggt gttggttgac atggtggtat    2220
ggtggtggtg tgtgggtggg tgttgggtgg tgggtgggaa ttggaggtgc tatcatggtg    2280
ggtatgttgg ggagttcgga ggatgcggtc tgtggggata tggttccagg gctaatgggt    2340
ctgggatggg tcaaggtgga ggggtgcgcg gtgtgcgtgt ggcgtggaga gcggcagttg    2400
ggtgcggcac cgcagcggcg gcaacgcagc agcataggcg gcgaggacgg cggcggcgct    2460
ccagcgggca gcgagccacg gcggcggcag ctcagaccag caccgccagg gcccagcagc    2520
gcagtgcagc cagcaacagc gctggtgcta ctgctggtgc tactgctggg aatgcggctg    2580
ttgtgggcgt cgagcagtag tgaccatcac cggcactgcg ctgcggcagc cggcctgcca    2640
tccagcatgg cgccgcgggg ctgggtgcgc aagcgaaagg cagcagtggt ggacagagct    2700
gttgaggcac ggcgcctgac tgcccggtgg tgacgatgtg cggatgctcg cgcccagcag    2760
aagggaccag gacccggctg gtggccgccg ccgccgccgc agcagcagtc gccacgtagc    2820
acgcagcggc tacagcagca accggcgccc acaccgcac  cacaaccca  gccaccgcac    2880 cagccaaaca cacgcaccct tccctctctc ccctctcct  cacacggccc gcactgacct    2940
gtccctcccc gtctccctct gctcccctc  cgccacctca gcgccgccgc caagccctac    3000
atcgcctcca tgggcatcta cgtcatgtcc gccaaggcgc tgcgcgagct gctgttgaac    3060
cgcatgccgg gcgccaacga cttcggaaac gaggtcatcc ccggcgccaa ggacgccggc    3120
ttcaaggtgc aggccttcgc ctttgacggc tactgggagg acatcggtac cgtggaggcc    3180
ttctacaacg ccaacctggc gctgaccgat cccgagaagg cgcagttctc gttctacgac    3240
aaggacgcgc cgatctacac catgtcgcgc ttcctgccgc cctccaaggt gatggactgc    3300
gacgtgaaca tgtccatcat cggcgacggc tgcgtgatca aggccggctc caagatccac    3360
aactccatca tcggcatccg ctcgctgatc ggctccgact gcatcatcga cagcgcgatg    3420
atgatgggct cggactacta cgagaccctg gaggagtgcg agtacgtgcc cggctgcctg    3480
```

```
cctatgggcg tgggcgatgg ctccatcatc cgtcgcgcca ttgtggacaa gaacgcgcgc    3540
attggtccca agtgccagat catcaacaag gacggcgtca aggaggccaa ccgcgaggac    3600
cagggcttcg tgatcaagga cggcattgtc gtcgtgatca aggactcgca catccccgcc    3660
ggcaccatca tctaaacgtg atggctcggg ccggaagag cgcggcggc gcagagccgg      3720 ccggcgcggc ggcagccggc ggcgcgcggc gtgtggcgga gacgttggtg atggagagca    3780
gacggaggtg gcgggacctc aggcacattt cggcagctgc cgcagcgagg agcagggaga    3840
gcgagcgtgt gtgggtgcac acgctagcgc gcactcacga cctgcagcag cagcagccgt    3900
ggcggagatg gcgggagctg ctcgggtact gttgaagcga ggcgggccct tggctgcgtt    3960
tttgggttgg aatgttgcgc agtgacggga ctctatagag taggggggat tgagtgtcct    4020
tggttcgggt gaacgccatg gaccggtgcg gcacggcgtg gcgtggcact gcgttgctgc    4080
ggaagcgcaa gctgcggcct tcccgcaacg gtgcagcagc cgcatcggac gcaacacccc    4140
aggagcggca gtagctgcca gtcgcgtgcg gctgttttga gggagagcgc tttttcggga    4200
gcgtgaacgg tcggaccaag caccggcggt ggcagcggca ggccttcggc cccccggccc    4260
ttaaagctgc cggcgccaag gcacgccgcg aggcgtgtgt gttcccgagg tgcagccggg    4320
cggtggcggc tgcagggtgg gtgcgagcca gctggcgtgc catccagcac ggcggcggtt    4380
gttgcggctc ggcggtgggg aaggtggagc actgagcggg cgtgggtcgg gacgcttcgc    4440
ggctcacgcg gcggttggcc gttgcggctg ccttccgtgg gatgccgtag gaggggcggg    4500
tccttactcg ctcgcgtccc acctgggggg ttgtagtttc ttaatttagc gtgtaccatg    4560
ctcaacattg tttgactccc ccagaccctg cgaacctgca tctgcggagg tagagagggc    4620
tcttgggtgt gtgcagattt ttggttgttt ggtttgggtg atggtgcaac agttttgcgc    4680
gtggcgagtg tgtgcgttct cagatgagga gaattgtttg tgctatgcag agttgaggcg    4740
agaggaagac ttttgggcac gactgcaccg tgcatccatg gagcacagct gcatagaagc    4800
acgtgggcaa cgcacggctt gcaccgtccg atgcatcgtc ccctccccca gagatttgga    4860
ccgagagaag aaatccagca catgtaaact cgtatgaggg ca                      4902
```

<210> SEQ ID NO 10
<211> LENGTH: 23
<212> TYPE: DNA
<213> ORGANISM: Artificial Sequence
<220> FEATURE:
<223> OTHER INFORMATION: RGEN1 Target

<400> SEQUENCE: 10
caccagctgc gcgaccgagc tgg                                            23

<210> SEQ ID NO 11
<211> LENGTH: 23
<212> TYPE: DNA
<213> ORGANISM: Artificial Sequence
<220> FEATURE:
<223> OTHER INFORMATION: RGEN2 Target

<400> SEQUENCE: 11
gccgttgcac ttctgaagca ggg                                            23

<210> SEQ ID NO 12
<211> LENGTH: 23
<212> TYPE: DNA
<213> ORGANISM: Artificial Sequence
<220> FEATURE:

<223> OTHER INFORMATION: RGEN3 Target

<400> SEQUENCE: 12
tccggcgaac gcacctggat ggg       23

<210> SEQ ID NO 13
<211> LENGTH: 23
<212> TYPE: DNA
<213> ORGANISM: Artificial Sequence
<220> FEATURE:
<223> OTHER INFORMATION: RGEN4 Target

<400> SEQUENCE: 13
tggtgggcgc cgacggcatc tgg       23

<210> SEQ ID NO 14
<211> LENGTH: 23
<212> TYPE: DNA
<213> ORGANISM: Artificial Sequence
<220> FEATURE:
<223> OTHER INFORMATION: RGEN5 Target

<400> SEQUENCE: 14
ccatggcttc gcaggcatct cgg       23

<210> SEQ ID NO 15
<211> LENGTH: 76
<212> TYPE: DNA
<213> ORGANISM: Artificial Sequence
<220> FEATURE:
<223> OTHER INFORMATION: sgRNA for RGEN RNP

<400> SEQUENCE: 15
gttttagagc tagaaatagc aagttaaaat aaggctagtc cgttatcaac ttgaaaaagt       60
ggcaccgagt cggtgc       76

<210> SEQ ID NO 16
<211> LENGTH: 1406
<212> TYPE: PRT
<213> ORGANISM: Artificial Sequence
<220> FEATURE:
<223> OTHER INFORMATION: Cas 9 protein

<400> SEQUENCE: 16

```
Met Gly Ser Ser His His His His His His Val Tyr Pro Tyr Asp Val
1               5                   10                  15

Pro Asp Tyr Ala Glu Leu Pro Pro Lys Lys Arg Lys Val Gly Ile
            20                  25                  30

Arg Ile Pro Gly Glu Lys Pro Asp Lys Lys Tyr Ser Ile Gly Leu Asp
        35                  40                  45

Ile Gly Thr Asn Ser Val Gly Trp Ala Val Ile Thr Asp Glu Tyr Lys
    50                  55                  60

Val Pro Ser Lys Lys Phe Lys Val Leu Gly Asn Thr Asp Arg His Ser
65                  70                  75                  80

Ile Lys Lys Asn Leu Ile Gly Ala Leu Leu Phe Asp Ser Gly Glu Thr
                85                  90                  95

Ala Glu Ala Thr Arg Leu Lys Arg Thr Ala Arg Arg Tyr Thr Arg
            100                 105                 110

Arg Lys Asn Arg Ile Cys Tyr Leu Gln Glu Ile Phe Ser Asn Glu Met
        115                 120                 125

Ala Lys Val Asp Asp Ser Phe Phe His Arg Leu Glu Glu Ser Phe Leu
```

```
                130                 135                 140
Val Glu Glu Asp Lys Lys His Glu Arg His Pro Ile Phe Gly Asn Ile
145                 150                 155                 160

Val Asp Glu Val Ala Tyr His Glu Lys Tyr Pro Thr Ile Tyr His Leu
                165                 170                 175

Arg Lys Lys Leu Val Asp Ser Thr Asp Lys Ala Asp Leu Arg Leu Ile
                180                 185                 190

Tyr Leu Ala Leu Ala His Met Ile Lys Phe Arg Gly His Phe Leu Ile
                195                 200                 205

Glu Gly Asp Leu Asn Pro Asp Asn Ser Asp Val Asp Lys Leu Phe Ile
210                 215                 220

Gln Leu Val Gln Thr Tyr Asn Gln Leu Phe Glu Glu Asn Pro Ile Asn
225                 230                 235                 240

Ala Ser Gly Val Asp Ala Lys Ala Ile Leu Ser Ala Arg Leu Ser Lys
                245                 250                 255

Ser Arg Arg Leu Glu Asn Leu Ile Ala Gln Leu Pro Gly Glu Lys Lys
                260                 265                 270

Asn Gly Leu Phe Gly Asn Leu Ile Ala Leu Ser Leu Gly Leu Thr Pro
                275                 280                 285

Asn Phe Lys Ser Asn Phe Asp Leu Ala Glu Asp Ala Lys Leu Gln Leu
                290                 295                 300

Ser Lys Asp Thr Tyr Asp Asp Leu Asp Asn Leu Leu Ala Gln Ile
305                 310                 315                 320

Gly Asp Gln Tyr Ala Asp Leu Phe Leu Ala Ala Lys Asn Leu Ser Asp
                325                 330                 335

Ala Ile Leu Leu Ser Asp Ile Leu Arg Val Asn Thr Glu Ile Thr Lys
                340                 345                 350

Ala Pro Leu Ser Ala Ser Met Ile Lys Arg Tyr Asp Glu His His Gln
                355                 360                 365

Asp Leu Thr Leu Leu Lys Ala Leu Val Arg Gln Gln Leu Pro Glu Lys
                370                 375                 380

Tyr Lys Glu Ile Phe Phe Asp Gln Ser Lys Asn Gly Tyr Ala Gly Tyr
385                 390                 395                 400

Ile Asp Gly Gly Ala Ser Gln Glu Glu Phe Tyr Lys Phe Ile Lys Pro
                405                 410                 415

Ile Leu Glu Lys Met Asp Gly Thr Glu Glu Leu Leu Val Lys Leu Asn
                420                 425                 430

Arg Glu Asp Leu Leu Arg Lys Gln Arg Thr Phe Asp Asn Gly Ser Ile
                435                 440                 445

Pro His Gln Ile His Leu Gly Glu Leu His Ala Ile Leu Arg Arg Gln
                450                 455                 460

Glu Asp Phe Tyr Pro Phe Leu Lys Asp Asn Arg Glu Lys Ile Glu Lys
465                 470                 475                 480

Ile Leu Thr Phe Arg Ile Pro Tyr Tyr Val Gly Pro Leu Ala Arg Gly
                485                 490                 495

Asn Ser Arg Phe Ala Trp Met Thr Arg Lys Ser Glu Glu Thr Ile Thr
                500                 505                 510

Pro Trp Asn Phe Glu Glu Val Val Asp Lys Gly Ala Ser Ala Gln Ser
                515                 520                 525

Phe Ile Glu Arg Met Thr Asn Phe Asp Lys Asn Leu Pro Asn Glu Lys
                530                 535                 540

Val Leu Pro Lys His Ser Leu Leu Tyr Glu Tyr Phe Thr Val Tyr Asn
545                 550                 555                 560
```

```
Glu Leu Thr Lys Val Lys Tyr Val Thr Glu Gly Met Arg Lys Pro Ala
                565                 570                 575
Phe Leu Ser Gly Glu Gln Lys Lys Ala Ile Val Asp Leu Leu Phe Lys
            580                 585                 590
Thr Asn Arg Lys Val Thr Val Lys Gln Leu Lys Glu Asp Tyr Phe Lys
        595                 600                 605
Lys Ile Glu Cys Phe Asp Ser Val Glu Ile Ser Gly Val Glu Asp Arg
    610                 615                 620
Phe Asn Ala Ser Leu Gly Thr Tyr His Asp Leu Leu Lys Ile Ile Lys
625                 630                 635                 640
Asp Lys Asp Phe Leu Asp Asn Glu Glu Asn Glu Asp Ile Leu Glu Asp
                645                 650                 655
Ile Val Leu Thr Leu Thr Leu Phe Glu Asp Arg Glu Met Ile Glu Glu
            660                 665                 670
Arg Leu Lys Thr Tyr Ala His Leu Phe Asp Asp Lys Val Met Lys Gln
        675                 680                 685
Leu Lys Arg Arg Arg Tyr Thr Gly Trp Gly Arg Leu Ser Arg Lys Leu
    690                 695                 700
Ile Asn Gly Ile Arg Asp Lys Gln Ser Gly Lys Thr Ile Leu Asp Phe
705                 710                 715                 720
Leu Lys Ser Asp Gly Phe Ala Asn Arg Asn Phe Met Gln Leu Ile His
                725                 730                 735
Asp Asp Ser Leu Thr Phe Lys Glu Asp Ile Gln Lys Ala Gln Val Ser
            740                 745                 750
Gly Gln Gly Asp Ser Leu His Glu His Ile Ala Asn Leu Ala Gly Ser
        755                 760                 765
Pro Ala Ile Lys Lys Gly Ile Leu Gln Thr Val Lys Val Val Asp Glu
    770                 775                 780
Leu Val Lys Val Met Gly Arg His Lys Pro Glu Asn Ile Val Ile Glu
785                 790                 795                 800
Met Ala Arg Glu Asn Gln Thr Thr Gln Lys Gly Gln Lys Asn Ser Arg
                805                 810                 815
Glu Arg Met Lys Arg Ile Glu Glu Gly Ile Lys Glu Leu Gly Ser Gln
            820                 825                 830
Ile Leu Lys Glu His Pro Val Glu Asn Thr Gln Leu Gln Asn Glu Lys
        835                 840                 845
Leu Tyr Leu Tyr Tyr Leu Gln Asn Gly Arg Asp Met Tyr Val Asp Gln
    850                 855                 860
Glu Leu Asp Ile Asn Arg Leu Ser Asp Tyr Asp Val Asp His Ile Val
865                 870                 875                 880
Pro Gln Ser Phe Leu Lys Asp Asp Ser Ile Asp Asn Lys Val Leu Thr
                885                 890                 895
Arg Ser Asp Lys Asn Arg Gly Lys Ser Asp Asn Val Pro Ser Glu Glu
            900                 905                 910
Val Val Lys Lys Met Lys Asn Tyr Trp Arg Gln Leu Leu Asn Ala Lys
        915                 920                 925
Leu Ile Thr Gln Arg Lys Phe Asp Asn Leu Thr Lys Ala Glu Arg Gly
    930                 935                 940
Gly Leu Ser Glu Leu Asp Lys Ala Gly Phe Ile Lys Arg Gln Leu Val
945                 950                 955                 960
Glu Thr Arg Gln Ile Thr Lys His Val Ala Gln Ile Leu Asp Ser Arg
                965                 970                 975
```

```
Met Asn Thr Lys Tyr Asp Glu Asn Asp Lys Leu Ile Arg Glu Val Lys
                980                 985                 990

Val Ile Thr Leu Lys Ser Lys Leu  Val Ser Asp Phe Arg  Lys Asp Phe
        995                 1000                1005

Gln Phe Tyr Lys Val Arg Glu  Ile Asn Asn Tyr His  His Ala His
        1010                1015                1020

Asp Ala Tyr Leu Asn Ala Val  Val Gly Thr Ala Leu  Ile Lys Lys
        1025                1030                1035

Tyr Pro Lys Leu Glu Ser Glu  Phe Val Tyr Gly Asp  Tyr Lys Val
        1040                1045                1050

Tyr Asp Val Arg Lys Met Ile  Ala Lys Ser Glu Gln  Glu Ile Gly
        1055                1060                1065

Lys Ala Thr Ala Lys Tyr Phe  Phe Tyr Ser Asn Ile  Met Asn Phe
        1070                1075                1080

Phe Lys Thr Glu Ile Thr Leu  Ala Asn Gly Glu Ile  Arg Lys Arg
        1085                1090                1095

Pro Leu Ile Glu Thr Asn Gly  Glu Thr Gly Glu Ile  Val Trp Asp
        1100                1105                1110

Lys Gly Arg Asp Phe Ala Thr  Val Arg Lys Val Leu  Ser Met Pro
        1115                1120                1125

Gln Val Asn Ile Val Lys Lys  Thr Glu Val Gln Thr  Gly Gly Phe
        1130                1135                1140

Ser Lys Glu Ser Ile Leu Pro  Lys Arg Asn Ser Asp  Lys Leu Ile
        1145                1150                1155

Ala Arg Lys Lys Asp Trp Asp  Pro Lys Lys Tyr Gly  Gly Phe Asp
        1160                1165                1170

Ser Pro Thr Val Ala Tyr Ser  Val Leu Val Val Ala  Lys Val Glu
        1175                1180                1185

Lys Gly Lys Ser Lys Lys Leu  Lys Ser Val Lys Glu  Leu Leu Gly
        1190                1195                1200

Ile Thr Ile Met Glu Arg Ser  Ser Phe Glu Lys Asn  Pro Ile Asp
        1205                1210                1215

Phe Leu Glu Ala Lys Gly Tyr  Lys Glu Val Lys Lys  Asp Leu Ile
        1220                1225                1230

Ile Lys Leu Pro Lys Tyr Ser  Leu Phe Glu Leu Glu  Asn Gly Arg
        1235                1240                1245

Lys Arg Met Leu Ala Ser Ala  Gly Glu Leu Gln Lys  Gly Asn Glu
        1250                1255                1260

Leu Ala Leu Pro Ser Lys Tyr  Val Asn Phe Leu Tyr  Leu Ala Ser
        1265                1270                1275

His Tyr Glu Lys Leu Lys Gly  Ser Pro Glu Asp Asn  Glu Gln Lys
        1280                1285                1290

Gln Leu Phe Val Glu Gln His  Lys His Tyr Leu Asp  Glu Ile Ile
        1295                1300                1305

Glu Gln Ile Ser Glu Phe Ser  Lys Arg Val Ile Leu  Ala Asp Ala
        1310                1315                1320

Asn Leu Asp Lys Val Leu Ser  Ala Tyr Asn Lys His  Arg Asp Lys
        1325                1330                1335

Pro Ile Arg Glu Gln Ala Glu  Asn Ile Ile His Leu  Phe Thr Leu
        1340                1345                1350

Thr Asn Leu Gly Ala Pro Ala  Ala Phe Lys Tyr Phe  Asp Thr Thr
        1355                1360                1365

Ile Asp Arg Lys Arg Tyr Thr  Ser Thr Lys Glu Val  Leu Asp Ala
```

-continued

```
                1370                1375                1380

Thr Leu Ile His Gln Ser Ile Thr Gly Leu Tyr Glu Thr Arg Ile
        1385                1390                1395

Asp Leu Ser Gln Leu Gly Gly Asp
        1400                1405

<210> SEQ ID NO 17
<211> LENGTH: 96
<212> TYPE: RNA
<213> ORGANISM: Artificial Sequence
<220> FEATURE:
<223> OTHER INFORMATION: sgRNA 1 of ZEP

<400> SEQUENCE: 17
uccggcgaac gcaccuggau guuuuagagc uagaaauagc aaguuaaaau aaggcuaguc      60
cguuaucaac uugaaaaagu ggcaccgagu cggugc                              96

<210> SEQ ID NO 18
<211> LENGTH: 83
<212> TYPE: DNA
<213> ORGANISM: Artificial Sequence
<220> FEATURE:
<223> OTHER INFORMATION: control

<400> SEQUENCE: 18
gccatccgcg gcgagggcaa gtaccgtgga cccatccagg tgcgttcgcc ggaacaccaa      60
cgcgcttgtt tttgctgtgc cgc                                            83

<210> SEQ ID NO 19
<211> LENGTH: 85
<212> TYPE: DNA
<213> ORGANISM: Artificial Sequence
<220> FEATURE:
<223> OTHER INFORMATION: ZEP-RGENE3 2 insert

<400> SEQUENCE: 19
gccatccgcg gcgagggcaa gtaccgtgga cccatctcca ggtgcgttcg ccggaacacc      60
aacgcgcttg tttttgctgt gccgc                                          85

<210> SEQ ID NO 20
<211> LENGTH: 82
<212> TYPE: DNA
<213> ORGANISM: Artificial Sequence
<220> FEATURE:
<223> OTHER INFORMATION: ZEP-RGENE3 1 delete

<400> SEQUENCE: 20
gccatccgcg gcgagggcaa gtaccgtgga cccatcaggt gcgttcgccg gaacaccaac      60
gcgcttgttt ttgctgtgcc gc                                             82

<210> SEQ ID NO 21
<211> LENGTH: 79
<212> TYPE: DNA
<213> ORGANISM: Artificial Sequence
<220> FEATURE:
<223> OTHER INFORMATION: ZEP-RGENE3 4 delete

<400> SEQUENCE: 21
gccatccgcg gcgagggcaa gtaccgtgga cccaggtgcg ttcgccggaa caccaacgcg      60
cttgtttttg ctgtgccgc                                                 79
```

```
<210> SEQ ID NO 22
<211> LENGTH: 89
<212> TYPE: DNA
<213> ORGANISM: Artificial Sequence
<220> FEATURE:
<223> OTHER INFORMATION: ZEP-RGENE3 6 insert

<400> SEQUENCE: 22
gccatccgcg gcgagggcaa gtaccgtgga cccatcaaca tccaggtgcg ttcgccggaa      60
caccaacgcg cttgtttttg ctgtgccgc                                        89

<210> SEQ ID NO 23
<211> LENGTH: 84
<212> TYPE: DNA
<213> ORGANISM: Artificial Sequence
<220> FEATURE:
<223> OTHER INFORMATION: ZEP-RGENE3 1 insert

<400> SEQUENCE: 23
gccatccgcg gcgagggcaa gtaccgtgga cccatctcag gtgcgttcgc cggaacacca      60
acgcgcttgt ttttgctgtg ccgc                                             84

<210> SEQ ID NO 24
<211> LENGTH: 23
<212> TYPE: DNA
<213> ORGANISM: Artificial Sequence
<220> FEATURE:
<223> OTHER INFORMATION: AGP4_sg1 RGEN Target

<400> SEQUENCE: 24
tagcatggcc ctgaagatgc ggg                                              23

<210> SEQ ID NO 25
<211> LENGTH: 23
<212> TYPE: DNA
<213> ORGANISM: Artificial Sequence
<220> FEATURE:
<223> OTHER INFORMATION: AGP4_sg2 RGEN Target

<400> SEQUENCE: 25
cagaccttcg tctgcccccca cgg                                             23

<210> SEQ ID NO 26
<211> LENGTH: 23
<212> TYPE: DNA
<213> ORGANISM: Artificial Sequence
<220> FEATURE:
<223> OTHER INFORMATION: AGP4_sg3 RGEN Target

<400> SEQUENCE: 26
gactcatctc gcaggctcag tgg                                              23

<210> SEQ ID NO 27
<211> LENGTH: 23
<212> TYPE: DNA
<213> ORGANISM: Artificial Sequence
<220> FEATURE:
<223> OTHER INFORMATION: AGP4_sg4 RGEN Target

<400> SEQUENCE: 27
gtcgaccccc gttgagacca agg                                              23

<210> SEQ ID NO 28
<211> LENGTH: 96
<212> TYPE: RNA
```

```
<213> ORGANISM: Artificial Sequence
<220> FEATURE:
<223> OTHER INFORMATION: sgRNA of AGP

<400> SEQUENCE: 28
gcaucuucag ggccaugcua guuuuagagc uagaaauagc aaguuaaaau aaggcuaguc    60
cguuaucaac uugaaaaagu ggcaccgagu cggugc                             96
```